(12) United States Patent  
Pollack et al.

(10) Patent No.: US 12,089,893 B2
(45) Date of Patent: Sep. 17, 2024

(54) DEVICES AND METHODS FOR TARGETED DELIVERY OF A SUBSTANCE

(71) Applicant: SANULUS MEDICAL, LLC, Chicago, IL (US)

(72) Inventors: John S. Pollack, Naperville, IL (US); William R. Voss, Hinsdale, IL (US)

(73) Assignee: Sanulus Medical, LLC, Dallas, TX (US)

( * ) Notice: Subject to any disclaimer, the term of this patent is extended or adjusted under 35 U.S.C. 154(b) by 0 days.

(21) Appl. No.: 17/866,111

(22) Filed: Jul. 15, 2022

(65) Prior Publication Data

US 2022/0346876 A1 Nov. 3, 2022

Related U.S. Application Data

(63) Continuation-in-part of application No. 17/739,585, filed on May 9, 2022, now Pat. No. 11,559,294, and
(Continued)

(51) Int. Cl.
*A61B 17/00* (2006.01)
*A61B 18/20* (2006.01)
*A61F 9/007* (2006.01)

(52) U.S. Cl.
CPC ........ *A61B 18/20* (2013.01); *A61B 17/00491* (2013.01); *A61F 9/00727* (2013.01);
(Continued)

(58) Field of Classification Search
CPC .............. A61F 9/00709; A61F 9/00727; A61F 9/00736; A61F 9/00754; A61F 9/0008; A61F 9/00008
See application file for complete search history.

(56) References Cited

U.S. PATENT DOCUMENTS

| 2,599,888 A | 6/1952 | Beezlet et al. |
| 2,828,579 A | 4/1958 | Schwerbel et al. |

(Continued)

FOREIGN PATENT DOCUMENTS

| FR | 2505150 | 11/1982 |
| JP | 4569971 | 10/2010 |

(Continued)

OTHER PUBLICATIONS

Alcon, "The Advanced ULTRAVIT Beveled High Speed Probe," NRMD, 2017, 2, 1 page.
(Continued)

*Primary Examiner* — Elizabeth Houston
*Assistant Examiner* — Lindsey Bachman
(74) *Attorney, Agent, or Firm* — Fish & Richardson P.C.

(57) ABSTRACT

Devices, systems and methods for applying a bioadhesive substance to an internal surface of the eye, such as the retina, can include an outer sleeve having a proximal end, a distal end, a passageway extending along a length of the elongate body and an opening at the distal end of the elongate body, an applicator tip including an elongate body having a proximal end and a distal end, an applicator portion coupled with the distal end of the elongate body, and a substance supply lumen extending along a length of the device through which a bioadhesive substance can pass so that the bioadhesive substance can be applied to at least the applicator portion of the applicator tip. Some embodiments of the device can also have a source of the bioadhesive substance in fluid communication with at least the substance supply lumen.

42 Claims, 35 Drawing Sheets

Related U.S. Application Data a continuation-in-part of application No. 17/368,551, filed on Jul. 6, 2021, now abandoned, and a continuation-in-part of application No. 16/516,112, filed on Jul. 18, 2019.

(60) Provisional application No. 63/050,695, filed on Jul. 10, 2020, provisional application No. 63/049,044, filed on Jul. 7, 2020, provisional application No. 62/796,338, filed on Jan. 24, 2019, provisional application No. 62/700,768, filed on Jul. 19, 2018.

(52) U.S. Cl.
CPC ............... *A61B 2017/00336* (2013.01); *A61B 2017/00951* (2013.01)

(56) References Cited

U.S. PATENT DOCUMENTS

| | | |
|---|---|---|
| 3,834,066 A | 9/1974 | Vargas |
| 4,752,383 A | 6/1988 | McKay et al. |
| 4,762,004 A | 8/1988 | Lalin et al. |
| 4,795,436 A | 1/1989 | Robinson |
| 4,874,368 A | 10/1989 | Miller et al. |
| 4,907,961 A | 3/1990 | Anderson |
| 5,019,037 A | 5/1991 | Wang et al. |
| 5,324,305 A | 6/1994 | Kanner |
| 5,334,163 A | 8/1994 | Sinnett |
| 5,368,563 A | 11/1994 | Lonneman et al. |
| 5,527,356 A | 6/1996 | Peyman et al. |
| 5,547,473 A | 8/1996 | Peyman |
| 5,844,087 A | 12/1998 | Zimmerman et al. |
| 5,858,345 A | 1/1999 | Charles et al. |
| 6,296,150 B1 | 10/2001 | Farris |
| 6,328,229 B1 | 12/2001 | Duronio et al. |
| 6,475,508 B1 | 11/2002 | Schwartz et al. |
| 6,478,775 B1 | 11/2002 | Galt |
| 6,488,695 B1 | 12/2002 | Hickingbotham |
| 6,547,467 B2 | 4/2003 | Quintero |
| 6,589,269 B2 | 6/2003 | Zhu et al. |
| 7,044,937 B1 | 5/2006 | Kirwan et al. |
| 7,220,224 B1 | 5/2007 | Peyman |
| 7,338,477 B2* | 3/2008 | Meyer .................. A61F 9/0017 604/289 |
| 7,867,222 B1 | 1/2011 | Tilton, Jr. et al. |
| 7,985,197 B2 | 7/2011 | Maeda et al. |
| 8,323,262 B2 | 12/2012 | D'Alessio et al. |
| 8,470,029 B2 | 6/2013 | Walter et al. |
| 8,790,366 B2 | 7/2014 | Cordova et al. |
| 8,950,629 B2 | 2/2015 | Kapec |
| 9,186,315 B2 | 11/2015 | Singer |
| 9,554,939 B1 | 1/2017 | Breazeale |
| 9,623,144 B2 | 4/2017 | Askari et al. |
| 9,694,299 B1 | 7/2017 | Kouso |
| 9,861,942 B1 | 1/2018 | Paul et al. |
| 9,937,300 B2 | 4/2018 | Beckstein et al. |
| 10,052,350 B2 | 8/2018 | Niu et al. |
| 10,500,090 B2 | 12/2019 | Gunn et al. |
| 11,166,844 B2 | 11/2021 | Charles et al. |
| 2001/0016709 A1 | 8/2001 | Tovey |
| 2003/0044219 A1 | 3/2003 | Quintero |
| 2003/0225380 A1 | 12/2003 | Redl |
| 2004/0039253 A1 | 2/2004 | Peyman |
| 2007/0092550 A1 | 4/2007 | Lui |
| 2007/0191781 A1 | 8/2007 | Richards |
| 2007/0208422 A1* | 9/2007 | Walter .................... A61F 9/007 623/5.11 |
| 2008/0121657 A1 | 5/2008 | Voegele |
| 2008/0294093 A1* | 11/2008 | Maeda ................ A61B 17/3468 606/1 |
| 2010/0114158 A1 | 5/2010 | Hattan et al. |
| 2010/0168779 A1 | 7/2010 | Redl |
| 2010/0228122 A1 | 9/2010 | Keenan et al. |
| 2010/0261652 A1 | 10/2010 | Wang et al. |
| 2012/0035335 A1 | 2/2012 | Ladet et al. |
| 2012/0271272 A1 | 10/2012 | Hammack et al. |
| 2013/0190808 A1 | 7/2013 | Tegels et al. |
| 2013/0022590 A1 | 8/2013 | Zysler et al. |
| 2013/0261538 A1 | 10/2013 | Miyazaki et al. |
| 2014/0206940 A1 | 7/2014 | Hufford |
| 2014/0330204 A1 | 11/2014 | Huculak et al. |
| 2015/0165181 A1* | 6/2015 | Honda .................. A61M 31/00 604/307 |
| 2015/0257928 A1* | 9/2015 | Iseli ...................... A61F 9/0017 604/93.01 |
| 2015/0283364 A1* | 10/2015 | Tanaka .................. A61M 35/00 604/290 |
| 2016/0220725 A1 | 8/2016 | Whalen, III et al. |
| 2016/0271290 A1 | 9/2016 | Humayun et al. |
| 2017/0100128 A1* | 4/2017 | Soens ............... A61B 17/12181 |
| 2017/0165109 A1 | 6/2017 | Gunn et al. |
| 2017/0172793 A1* | 6/2017 | Gunn ...................... A61F 9/007 |
| 2017/0333253 A1 | 11/2017 | Heeren et al. |
| 2018/0036452 A1 | 2/2018 | Askari et al. |
| 2018/0360743 A1 | 12/2018 | Bartynski et al. |
| 2019/0254705 A1* | 8/2019 | Humayun .............. A61B 17/02 |
| 2020/0022691 A1 | 1/2020 | Pollack et al. |
| 2020/0375844 A1* | 12/2020 | Maschio ................ A61B 17/00 |
| 2021/0121326 A1* | 4/2021 | Kahook .............. A61F 9/00736 |
| 2022/0008250 A1 | 1/2022 | Pollack et al. |
| 2022/0257227 A1 | 8/2022 | Pollack et al. |

FOREIGN PATENT DOCUMENTS

| | | |
|---|---|---|
| JP | 2015530202 | 10/2015 |
| WO | WO2012149468 | 11/2012 |
| WO | WO 2014056895 | 4/2014 |
| WO | WO2017060913 | 4/2017 |
| WO | WO2017103818 | 6/2017 |
| WO | WO2018232384 | 12/2018 |

OTHER PUBLICATIONS

Annabi et al., "Engineering a high elastic human protein-based sealant for surgical applications," Sci, Transl. Med., Oct. 2017, 9, 12 pages.

Barliya et al., "Transcleral approach for closing retinal tears using DuraSeal™ hydrogel sealant," Feb. 2018, 66(2):238-243.

Bayat et al., "A reversible thermoresponsive sealant for temporary closure of ocular trauma," Science Translational Medicine, Dec. 2017, 9(419), 47 pages.

Brownell, "Sticky when wet: strong adhesive for wound healing," Wyss Institute, Jul. 27, 2017, 10 pages.

Gilbert, "Adhesives in retinal detachment surgery," Br. J. Ophthalmol., 1991, 75:309-310.

Hofman et al., "Bioinspired Underwater Adhesives by Using the Supramolecular Toolbox," Adv. Mater., 2018, 30(19):1-38.

International Search Report and Written Opinion in International Appln. No. PCT/US20201/070831, dated Oct. 27, 2021, 15 pages.

International Search Report and Written Opinion in PCT/US2019/042481, dated Nov. 12, 2019, 17 pages.

Khalil et al., "Ciprofloxacin-loaded Bioadhesive Hydrogels for Ocular Applications," Biomaterials Science, 2020, 16 pages.

Kolasinski, "Bubbles: A review of their relationship to the formation of thin films and porous material," Mesoporous Biomaterials, 2014:49-60.

Mamor, "Control of Subretinal Fluid: Experimental and Clinical Studies, " Eye, 1990, 4: 340-344.

MedOne.com [online], "DualBore Cannulas," Available 2016, retrieved from URL<https://medone.com/dual-bore-cannulas/>, 2 pages.

North et al., "High Strength Underwater Bonding with Polymer Mimics of Mussel Adhesive Proteins," ACS, Feb. 2017, 7866-7872.

PCT International Preliminary Report on Patentability in International Appln. No. PCT/US2019/042481, dated Feb. 1, 2021, 9 pages.

Perdue.edu [online], "New 'biomimetic' glue shows high-strength bonding under water," Mar. 2017, retrieved on Apr. 29, 2022,

(56) References Cited

OTHER PUBLICATIONS retrieved from URL <https://www.purdue.edu/newsroom/releases/2017/Q1/new-biomimetic-glue-shows-high-strength-bonding-underwater.html>, 6 pages.

Sani et al., "Sutureless repair of corneal injuries using naturally derived bioadhesive hydorgels," Sci. Adv., Mar. 20, 2019, 5:1-14.

Sarfare et al., "Biocompatibility of a Synthetic Biopolymer for the treatment of Rhegmatogenous Retinal Detachment," J Clin Exp Ophthalmol., 2015 6(5):1-8.

Sciencedaily.com [online], "New insights into underwater adhesives," Jan. 16, 2018, retrieved on Apr. 29, 2022, retrieved from URL <https://www.sciencedaily.com/releases/2018/01/180116123801.htm>, 4 pages.

Tamiya et al., "Role of epithelial—mesenchymal transition in proliferative vitreoretinopathy," Experimental Eye Research, 2016, 142: 26-31.

Teruya et al., "Patching retinal breaks with Seprafilm in experimental rhegmatogenous retinal detachment of rabbit eyes," Eye, Jan. 2009, 2256-2259.

Trikha et al., "Small Gauge Pars Plana Vitrectomy," Vitrectomy, Apr. 2012, Chapter 4, p. 63.

Tyagi et al., "Glue-assisted retinopexy for rhegmatogenous retinal detachments (GuARD): A novel surgical technique for closing retinal breaks," Indian J. Ophthamol., May 2019, 67(5):677-680.

Wang et al., "Intraocular Application of Fibrin Glue as an Adjunct to Pars Plana Vitrectomy for Rhegmatogenous Retinal Detachment," Retina, the Journal of Retinal and Vitreous Diseases, 2019, 1-7.

Wang et al., "Intraocular Application of Fibrin Glue as an Adjunct to Pars Plana Vitrectomy for Rhegmatogenous Retinal Detachment," Retina, the Journal of Retinal and Vitreous Diseases, 2020, 40(4):718-724.

Machine Translation of JP4569971, Espacenet, 12 pages.

Machine Translation of JP4569971, Japanese Platform for Patent Information, 29 pages.

International Search Report and Written Opinion in International Appln. No. PCT/US2023/070121, mailed on Oct. 31, 2023, 15 pages.

Office Action in Japanese Application No. 2023-501166, dated Dec. 12, 2023, 7 pages (with English Translation).

European Extended Search Report in European Application No. EP 23157070.6, dated Jul. 4, 2023, 7 pages.

Katzin, "Aqueous Fibrin Fixation of Corneal Transplants in the Rabbit," Archives of Ophthalmology, Apr. 1946, 35(4):415-420.

\* cited by examiner

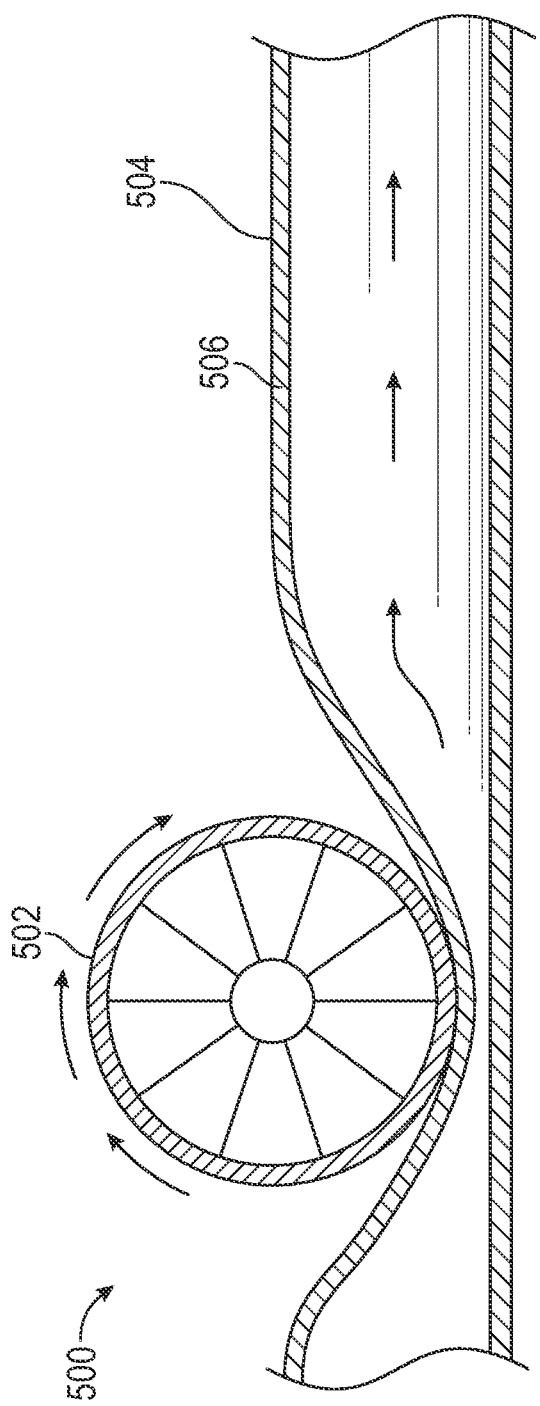
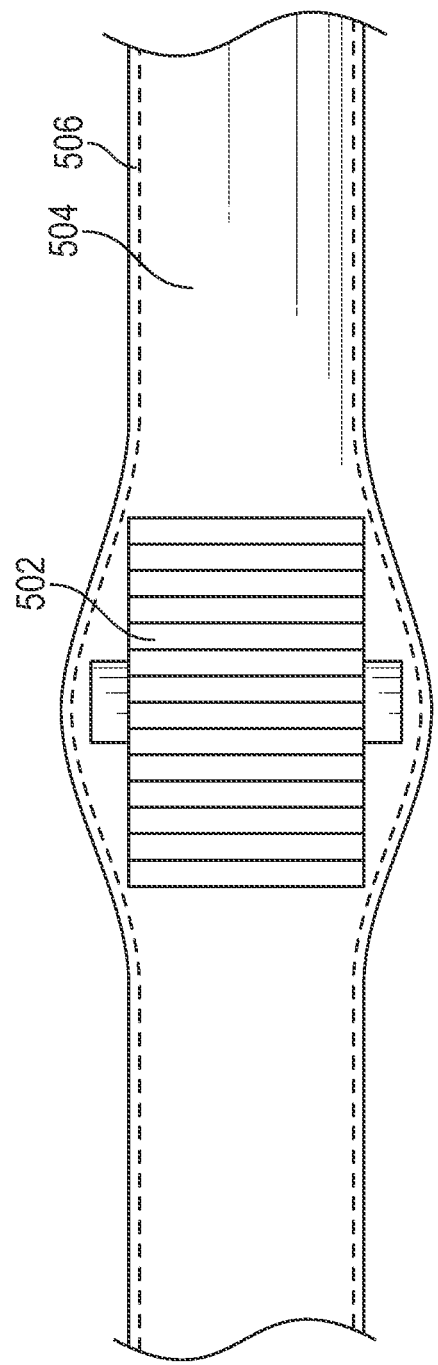
FIG. 16A
FIG. 16B

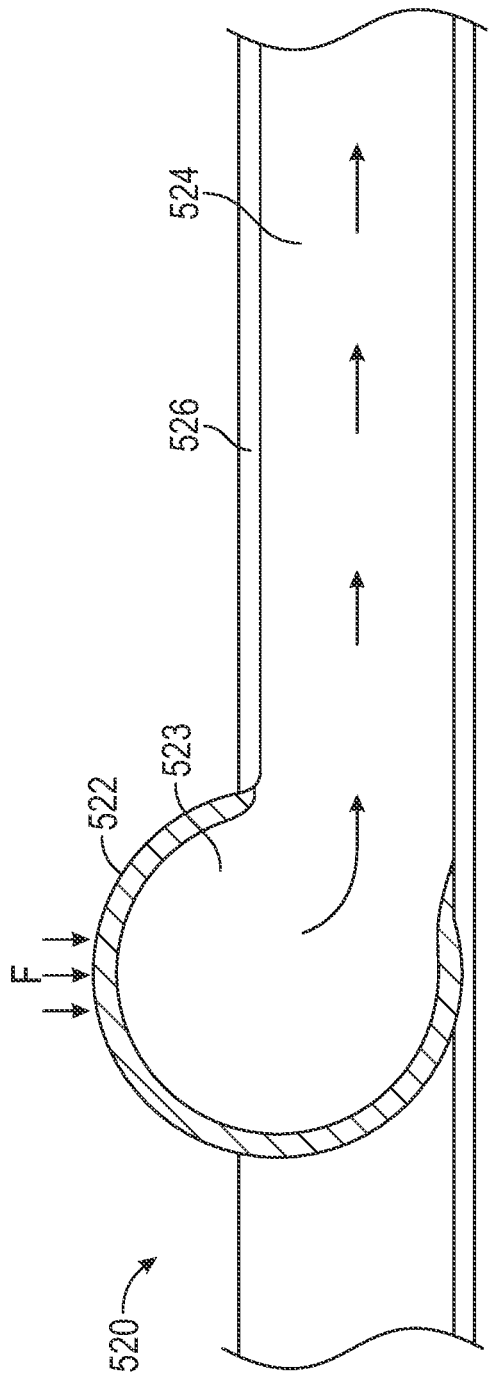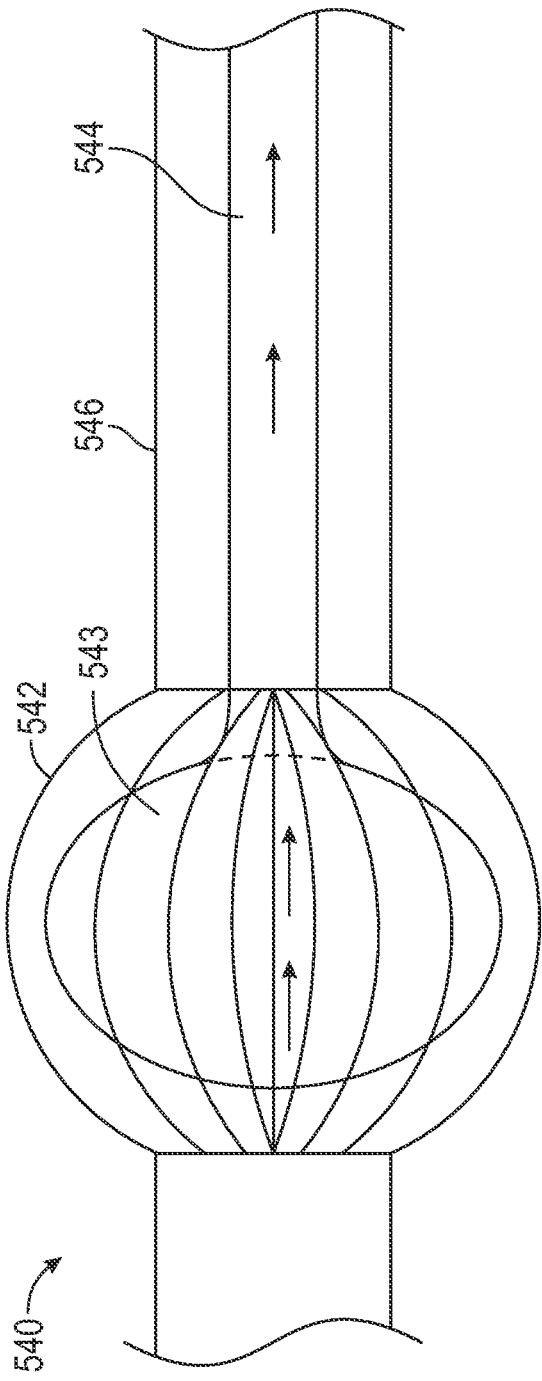

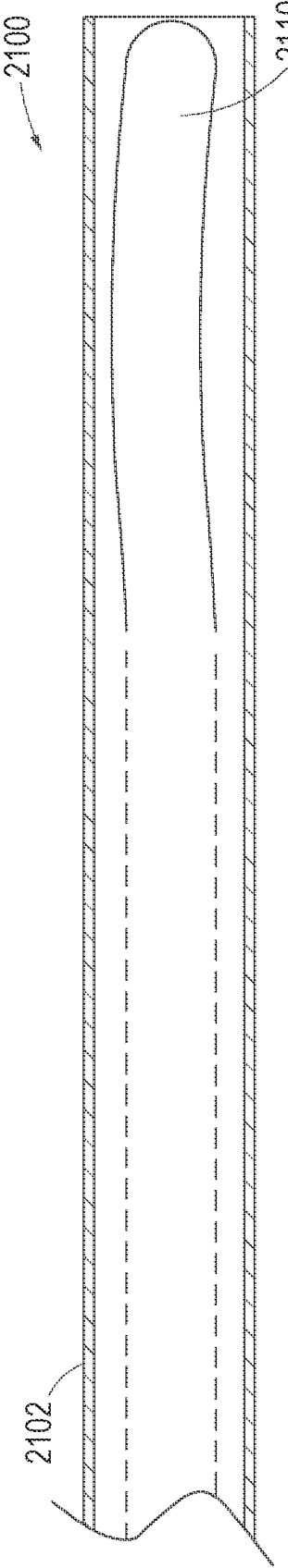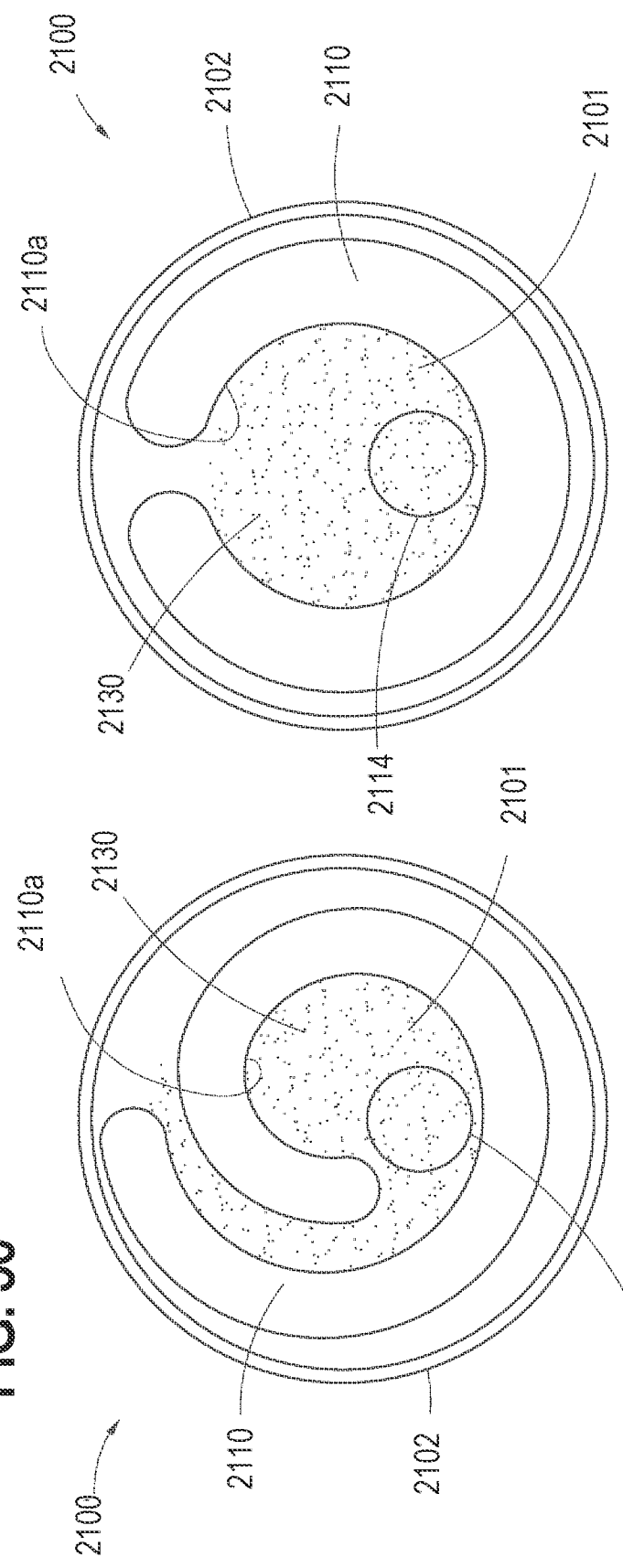

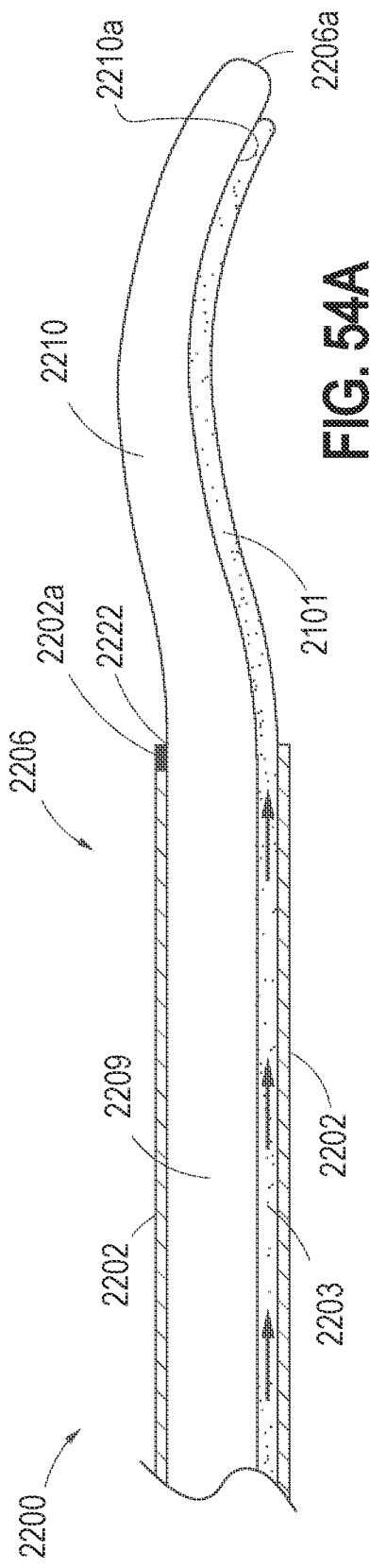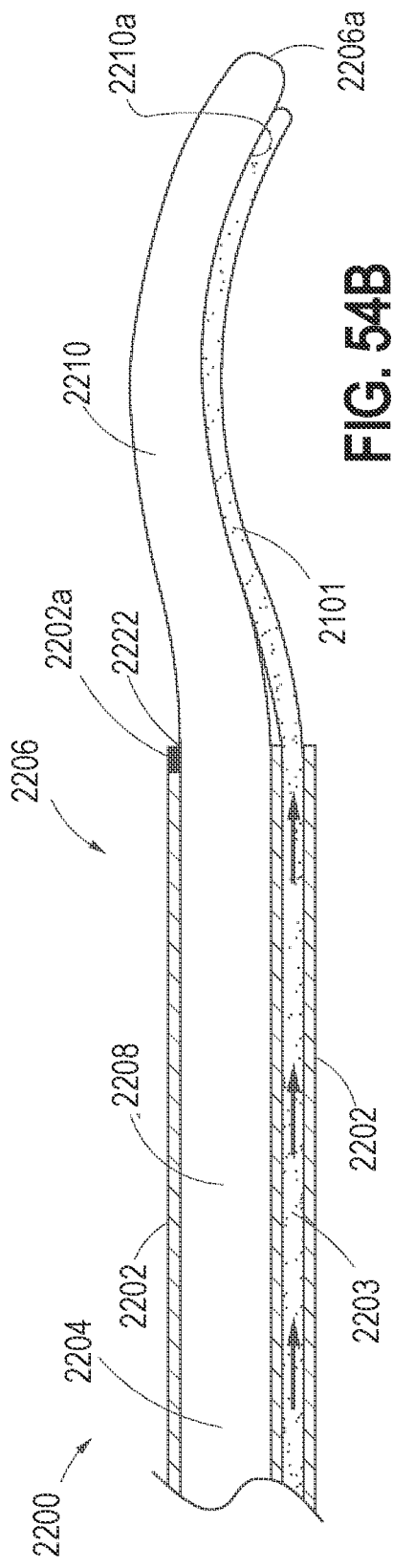

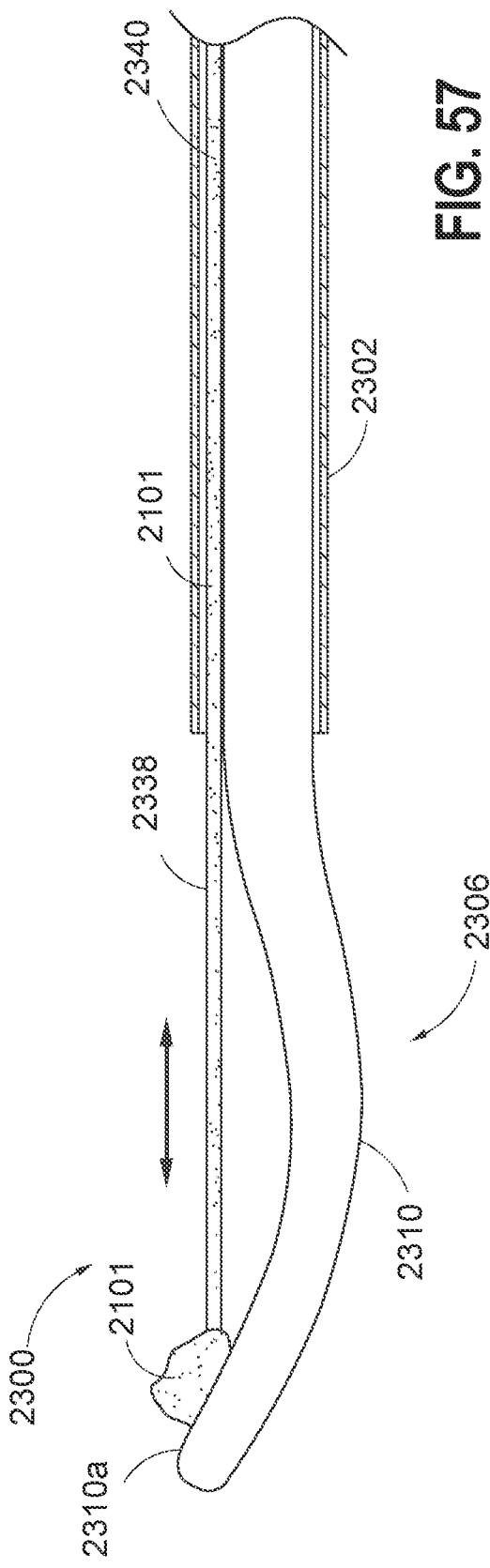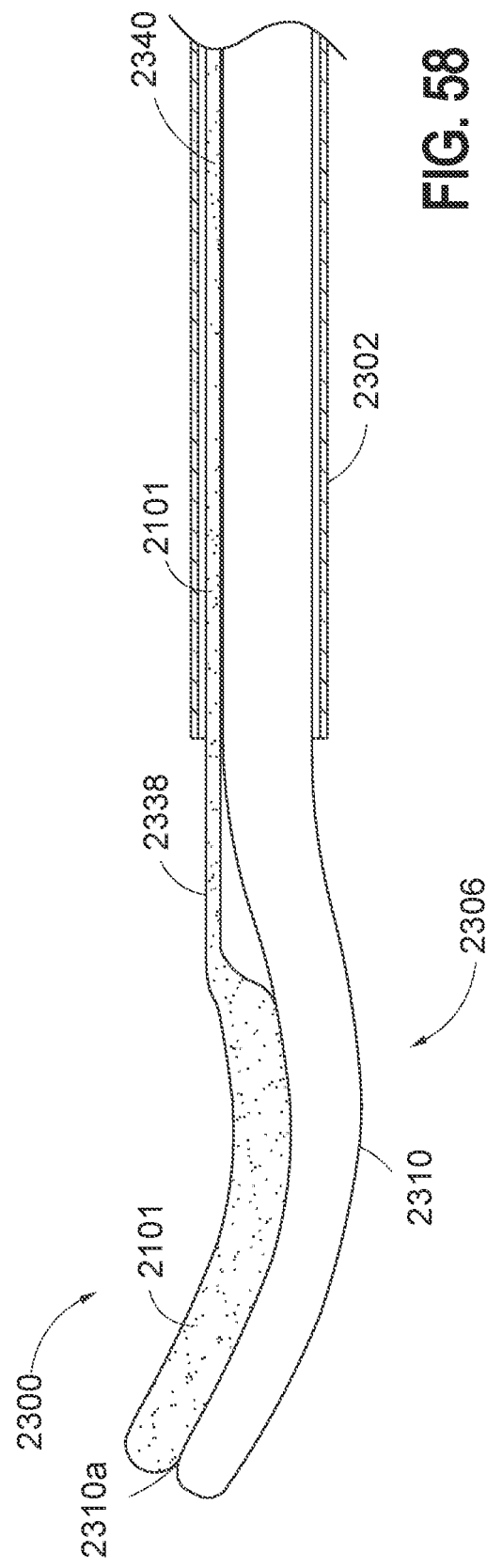

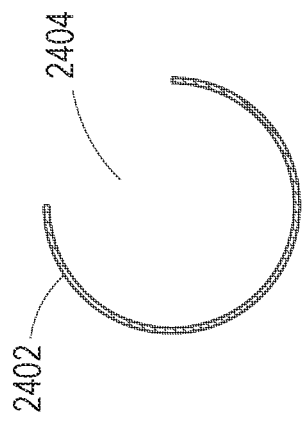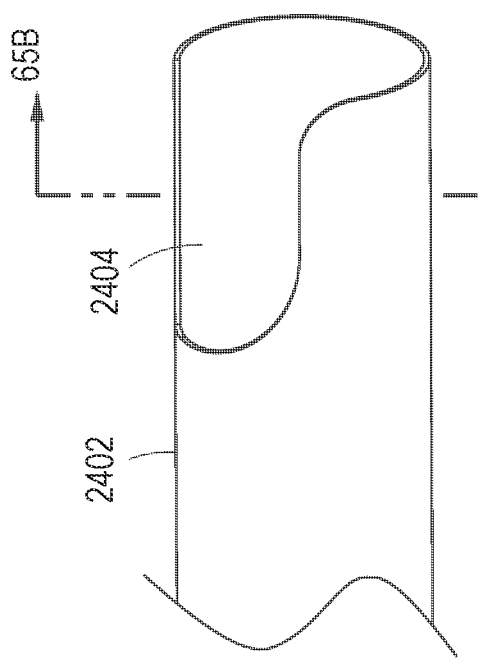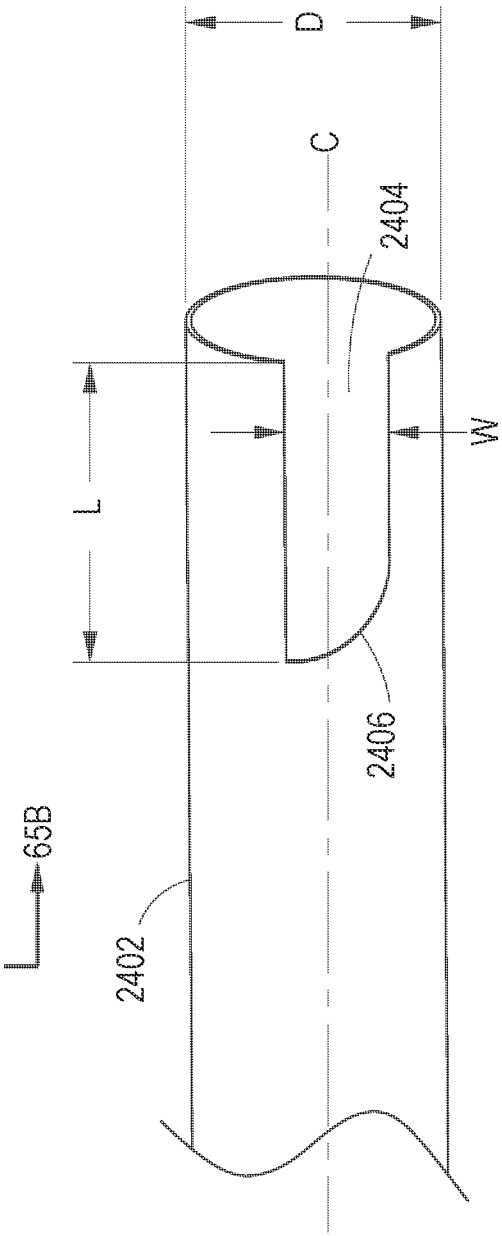
FIG. 65A
FIG. 65B
FIG. 65C

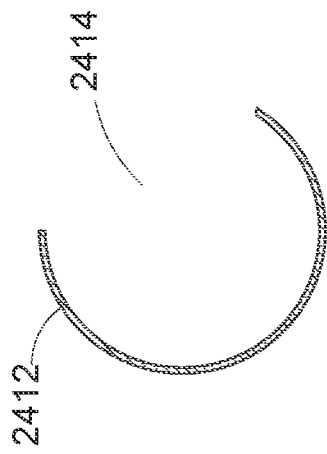
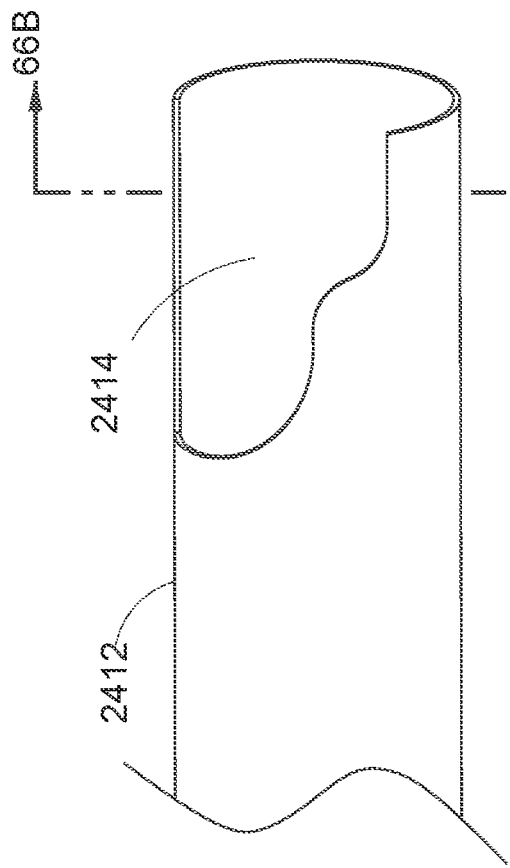
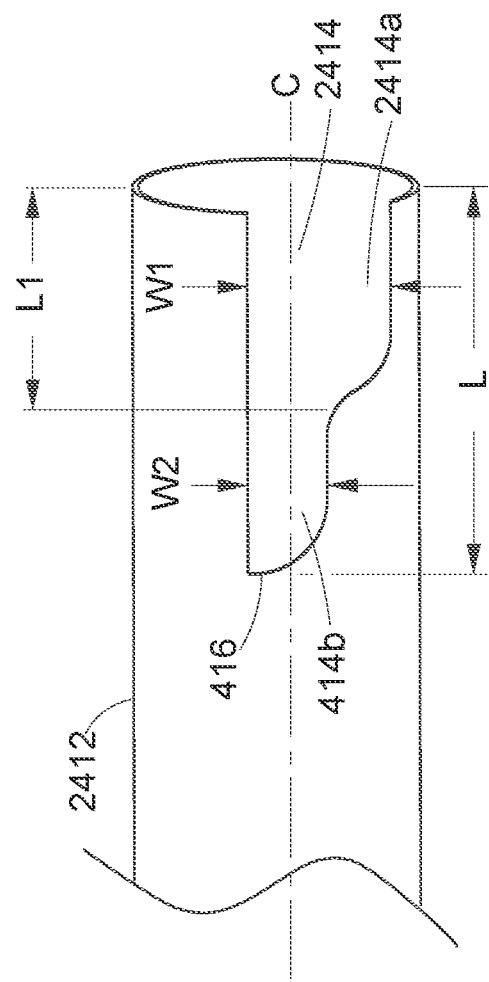

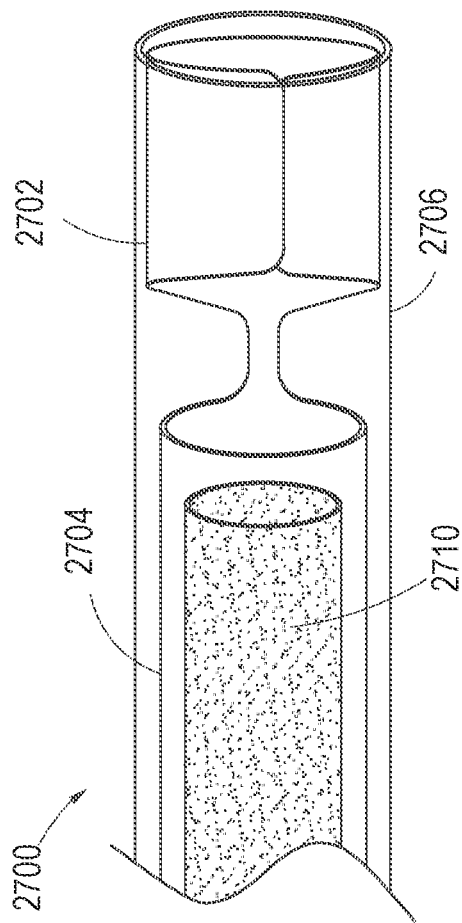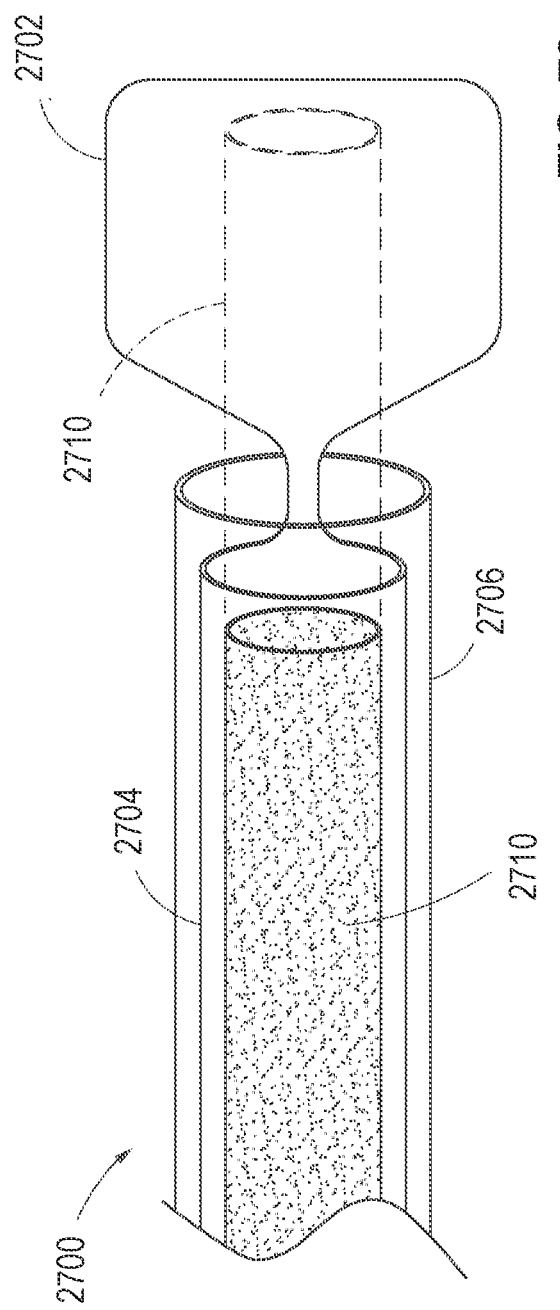

DEVICES AND METHODS FOR TARGETED DELIVERY OF A SUBSTANCE

CROSS-REFERENCE TO RELATED APPLICATIONS

This application claims priority as a continuation-in-part to U.S. Non Provisional patent application Ser. No. 16/516,112, filed Jul. 18, 2019; U.S. Non-Provisional patent application Ser. No. 17/739,585, filed May 9, 2022; U.S. Non-Provisional patent application Ser. No. 17/368,551, filed Jul. 6, 2021; U.S. Provisional Patent Application Ser. No. 63/049,044, filed on Jul. 7, 2020; U.S. Provisional Patent Application Ser. No. 63/050,695, filed on Jul. 10, 2020; U.S. Provisional Patent Application Ser. No. 62/796,338, filed on Jan. 24, 2019; and U.S. Provisional Patent Application Ser. No. 62/700,768, filed on Jul. 19, 2018. The contents of each of these priority applications are hereby incorporated by reference herein in their entirety as if fully set forth herein for all purposes.

BACKGROUND

Existing methods for fixing macular holes and retinal detachments, associated with retinal discontinuities such as tears and holes, include perfluorocarbon, laser, cryotherapy, gas bubble injection, and the use of silicone oil. The use of perfluorocarbon for displacement of fluid out of the subretinal space may result in inadvertent migration of perfluorocarbon liquid into the subretinal space which can result in vision loss if it is located in the central macula. Incomplete removal of perfluorocarbon liquid from the vitreous cavity may result in associated visual phenomena that patients may find annoying. Use of laser and cryotherapy results in permanent retinal scar tissue formation and may contribute to epiretinal membrane and epiretinal scar tissue formation. Use of gas bubble injection results in limitations on activities of the patient and can cause complications such as elevated intraocular pressure and cataracts. Likewise, silicone oil can be problematic because it sometimes causes complications such as elevation of intraocular pressure, requires a second surgery for removal, and frequently leaves behind residual oil bubbles after attempted removal that patients may find visually distracting.

Existing methods for fixing leaking eye wall discontinuities such as incisions, sclerotomies, and lacerations include sutures and commercially available bioadhesives. Sometimes sutured discontinuities continue to leak. Sutures cause ocular irritation, pain, tearing, and sometimes local tissue reactions that included edema and inflammation of the episclera and conjunctiva.

One difficulty with some bioadhesives is that they may induce toxicity. Another difficulty is that bioadhesive can be difficult to apply to non-dependent ocular surfaces, both inside and outside the eye, due to the effect of gravity on the bioadhesive as it leaves the tip of the bioadhesive delivery device and other factors. For example, in an eye with a retinal tear that is located on the lateral or superior aspect of the eye, gravity may make it difficult to apply the bioadhesive to the retinal tear since gravity may cause dripping or drooping of the bioadhesive as soon as the adhesive is expelled from the applicator device, preventing the accurate application of the adhesive over the retinal discontinuity. The same problem occurs when attempting to apply liquid or viscous materials to lateral and inferior outer eye surfaces. Another difficulty with bioadhesives is that they can be difficult to apply to large discontinuities of retina and other ocular surfaces, as well as tissue discontinuities that have an irregularly shaped margin or margins that are at different elevations from one another. Challenges in applying bioadhesives to retinal discontinuities can be even more difficult if attempted using a transcleral, subretinal approach.

SUMMARY

Arrangements disclosed herein include devices, systems, and methods for applying a substance such as, optionally, a bioadhesive, to a surface of an object. The tissue can be a biological or a non-biological (e.g., non-living) tissue and can include medical scaffolding, patches, covers, grafts, or other objects used in medical and non-medical applications. The object can be a tissue such that the devices and methods disclosed herein apply the substance to the tissue surface. The tissue can be a damaged tissue of any of the types or applications disclosed herein, including without limitation retinal tissue or other ocular tissue. As used herein, any features, components or other details that are described relative to a component, a device, a system, method, or any arrangements thereof are meant to apply to any of the other similar or suitable components, devices, systems, methods, and arrangements thereof disclosed herein.

As will be described, the devices, systems, and methods disclosed herein are configured to apply a substance, which can optionally be a bioadhesive, to the target tissue as a bubble, thin membrane, or other similar shape or arrangement. Some nonlimiting examples of applications of any of the devices and methods disclosed herein include applying a bio-substance such as a bioadhesive to an ocular tissue such as for example a retinal tear, retinal hole, retinal detachment, etc., applying bioadhesive to the sclera, conjunctiva, and cornea, applying a bio-substance such as a bioadhesive to gastrointestinal tissue, colon tissue, etc. for sealing perforations or tears therein, air filled ocular cavities or spaces, or otherwise. However, the arrangements of the devices and methods disclosed herein are not limited to the delivery of therapeutic substances or ocular, medical, or biological applications. Any of the devices and methods disclosed herein can be used for the delivery of any desired or suitable substance or material in any desired application-biological, non-biological, mechanical, or otherwise.

Any arrangements of the device for applying a substance to a tissue can optionally include a handle portion, an elongate body comprising a proximal end, a distal end, and an intermediate region extending therebetween, an exit port at a distal end, at least one fluid passageway (also referred to herein as a first passageway) in fluid communication with the exit port. The fluid passageway can extend from the handle toward the intermediate region or beyond to the distal end. The elongate body can also include a tubing member or cannula which can have a proximal portion, a distal tip, and a body portion extending therebetween.

In any arrangements, the system can comprise, can be comprised of, or consist of a unitary device wherein all of the components of the system are connected (e.g., fluidically coupled) to one another. Additionally, in any arrangements, the system can comprise, can be comprised of, or consists of a non-unitary device wherein one or more components of the system can be detached or detachable from another component of the system or be provided completely separately from other components. Some arrangements of the device can be modular, interchangeable components.

A variety of materials can be used to make the system and/or device. The handpiece or cannula, or a component thereof, can comprise plastic, metal, polyvinyl chloride, glass, acrylic, carbon fibers and/or wood.

The distal tip and/or the end surface of the distal tip in any arrangements disclosed herein can have a retention ridge, lip or rim comprising a flat surface configured to hold and maintain the bubble substance. The end surface of any devices disclosed herein can have an inward member circumferentially facing inward toward a center of the distal tip, or circumferentially extending into the cannula exit port. The inward member can be configured to retain the bioadhesive substance and aid in formation of the bioadhesive bubble or of the spherical film of bioadhesive substance. The distal tip can have multiple end surfaces. In some arrangements, the distal tip can have no more than one end surface. The distal tip can be blunt or rounded, or can have a blunt or a rounded end.

The distal tip of any arrangements can optionally have a circumferential edge, and four or more, or from two to eight, or from four to six flaps extending inwardly across the cannula exit port. One or more of the flaps can have a beveled edge. A variety of materials can be used to produce the flaps, including without limitation rubber, silicone, plastic, or an elastic substance.

Some arrangements of the system further comprise a substance supply channel within the device or that can be advanced into the device to aid in the production of a bioadhesive bubble. The substance supply channel may be within or exterior to the expansion fluid passageway of the device (sometimes referred to herein as a handpiece) and/or the fluid passageway of the cannula. The substance supply channel can have an elongate body comprising a proximal end and a distal end comprising a substance supply tip and/or exit port. The substance supply channel can be internal to or surrounded by at least a portion of the expansion fluid passageway of the cannula body, and/or a fluid passageway of the cannula base or tip. The cannula can have an outer wall and an inner wall, the inner wall which can optionally provide a boundary to a substance supply channel, and a space between the inner wall and the outer wall comprising the expansion fluid passageway of the device, the fluid passageway of the cannula body, or a fluid passageway of the cannula base or tip. The substance supply tip can have a surface that is beveled as compared to a longitudinal axis of the substance supply channel body and the substance supply exit port. The end surface of the substance supply tip can have a 1-15°, 15-30°, 30-45°, 45-60°, 60-75°, 75-89°, 91-105°, 105-120°, 120-135°, 135-150°, 150-165° or 165-179° angle, or an angle in a range comprising more than one of the aforementioned angle ranges, compared to the longitudinal axis of the substance supply channel body. The substance supply channel can have a substance supply tip that can have one, from one to ten or more or from four to eight, or any number therebetween, or more substance supply tip exit ports. The substance supply channel can have a proximal end that extends into the fluid passageway of the cannula, and wherein the gas flows around the substance supply channel when the gas is blown through the fluid passageway of the cannula.

Some arrangements of the system further comprise circumferential or non-circumferential intermittent support structures connecting the outer wall and the inner wall, for example two or more, from four to eight, or from six to ten or more, or any number therebetween, or more circumferential and/or non-circumferential intermittent support structures. These support structures can be used to provide a connection between an inner tube, chamber or wall and an outer tube, chamber or wall of the system.

The substance supply channel can surround at least a portion of the expansion fluid passageway of the device, the fluid passageway of the cannula body, or a fluid passageway of the cannula base or tip. The cannula can have an outer wall and an inner wall, and a space between the inner wall and the outer wall, the space between the inner wall and the outer wall which can comprise the substance supply channel, and the inner wall comprising the expansion fluid passageway of the handpiece, the fluid passageway of the cannula body, or a fluid passageway of the cannula base or tip.

The substance supply channel can be a tube within the expansion fluid passageway of the device, the fluid passageway of the cannula body, and/or a fluid passageway of the cannula base or tip. The substance supply channel tube can extend within the cannula and be advanceable up to the distal tip of the device. The substance supply channel tube can have a distal end that reaches near the cannula exit port.

The substance supply channel, elongate body of the substance supply channel, substance supply tip and/or substance supply exit port can have any suitable size. The substance supply channel, elongate body of the substance supply channel, substance supply tip and/or substance supply exit port can have any suitable length.

Some arrangements of the system further comprise a second substance supply channel. For example, multiple internal supply chambers can be separated by support structures connecting an outer wall and an inner wall. The substance supply channel and the second substance supply channel each can be configured to provide a separate substance, for example a polyethylene glycol solution and a trilysine amine solution. The substance supply channel and the second substance supply channel each can have separate substances; for example one chamber may comprise one bioadhesive substance, and the other chamber may comprise an activator substance. Other substances may also be provided for in the one or more chambers. For example, in one arrangement, a first chamber may contain the bioadhesive, a second chamber a curing agent, and a third chamber a medicament (e.g., anti-inflammatory, antibiotic, etc.) it is contemplated that the struts or support structures can separate two or more chambers. For example a series of non-continuous struts can provide support by connecting an outer wall to an inner wall, or by connecting an outer wall of distal tip to an outer wall of a fluid passageway or substance supply channel within the distal tip.

Any arrangements of the system can have a substance dispenser. The substance dispenser can have a base with a well or a series of wells. The base can be made of plastic, metal or glass. The well or the series of wells can each hold a substance such as the bioadhesive substance.

Any suitable substances may be used. The bioadhesive substance can optionally include ReSure™ sealant, a polyethylene glycol hydrogel, a polymeric gel, a double layer hydrogel, cyanoacrylate, fibrin glue, a polyethylene glycol solution, or a trilysine amine solution. The bioadhesive substance can include a resin. In any arrangements, the substance bubble or the approximately spherical film of substance enclosing the expansion fluid can have any suitable diameter or size. The diameter can change, expand, and/or decrease within, between, or among any of the aforementioned ranges.

Some arrangements relate to a handheld device for applying a bioadhesive bubble to a retina, comprising: an elongate body comprising a first end and a second end, the first end comprising a handle, the second end comprising a cannula comprising an exit port, at least one expansion fluid passageway extending from the first end towards the second end; a distal tip at the second end, and configured to generate a bioadhesive bubble from a bioadhesive when a gas or liquid flows through the expansion fluid passageway, maintain the bubble on the distal tip when the gas stops flowing through the expansion fluid passageway, and release the bubble when the bubble is brushed against a retina or when the gas flows again through the expansion fluid passageway, or when it can be released by heating or cooling the tip of the cannula or using a second instrument to disengage bubble from distal tip.

Some arrangements relate to a handheld device for applying a bioadhesive bubble to a retina, configured to generate a bioadhesive bubble from a bioadhesive when a gas or liquid flows through the internal fluid passageway, maintain the bubble on the distal tip when the gas stops flowing through the internal fluid passageway, and release the bubble when the bubble is brushed against a retina or when the gas flows again through the internal fluid passageway, or when heating or cooling the tip of the cannula or using a second instrument to disengage the bubble from the distal tip.

Some arrangements relate to a kit comprising a system or device described herein. Some arrangements of the kit further comprise a second system or device, and wherein the systems or devices are each disposable after a single or limited number of uses. Some arrangements of the kit further comprise an adhesive biomaterial, a substance dispenser, and/or a tip plug or protective cover.

Some arrangements relate to a use of a system, device or kit for applying the bioadhesive bubble to an eye or retina such as for repair of the eye or retina. Some arrangements relate to a method of repairing a retinal tear, comprising: generating, with a system, device or kit, a bioadhesive bubble comprising an approximately spherical film of bioadhesive substance enclosing an expansion fluid, and applying the bioadhesive bubble to the eye or retina from the system, device or kit.

Some arrangements relate to a system for applying a bioadhesive bubble to a retina, or other biologic tissue. The system can have a handpiece and/or a cannula. The handpiece can have an elongate body comprising a proximal end, a distal end, and an intermediate region extending therebetween, wherein at least a proximal portion of the intermediate region can have a handle, the distal end comprising an exit port, and/or at least one expansion fluid passageway in fluid communication with the exit port and extending proximally towards the intermediate region. The cannula can include a cannula base, a distal tip, and/or a cannula body extending therebetween. The cannula body can include a fluid passageway configured to fluidically communicate with the exit port and receive an expansion fluid passed through the expansion fluid passage and exit port the distal tip can have a flat, non-beveled surface comprising a cannula exit port at the distal end of the distal tip, the surface configured to support a bioadhesive bubble generated when expansion fluid flows through the expansion fluid passageway to the at cannula exit port at the distal end of the distal tip and through a bioadhesive substance contained within the handpiece or cannula, thereby generating an approximately spherical film of bioadhesive substance enclosing the expansion fluid. There can be no bevel at the distal tip or within the cannula exit port.

In a first aspect, a device for applying a bubble of a substance to a tissue surface, the device comprising a cannula having a proximal end portion, a distal end portion, and an intermediate portion extending therebetween, a distal tip at the distal end portion of the cannula, the distal tip having a bubble support surface and an exit port extending through the bubble support surface, an expansion fluid passageway extending through at least the intermediate portion and the distal portion of the cannula, the expansion fluid passageway being in fluid communication with the exit port, a source of an expansion fluid, and an actuator coupled with the source of the expansion fluid and configured to selectively advance the expansion fluid through the expansion fluid passageway and the exit port upon actuation of the actuator. In an operable state, the distal tip can be configured to support a layer of the substance on the bubble support surface so that the layer of the substance completely covers the distal port. Additionally, when the device is in the operable state, the device can be configured such that the advancement of the expansion fluid from the fluid source through the exit port causes at least one bubble of the substance to form from the layer of the substance on the bubble support surface of the distal tip. Additionally, the device can be configured such that at least a portion of the bubble can be transferred from the distal tip to the tissue surface so as to treat a defect on the tissue surface. This can be achieved, in any arrangements disclosed herein, by moving the cannula, the distal tip, applicator portion, the loop, or device or component so that the bubble, the substance, the loop, the applicator portion, or otherwise over the tissue surface and/or the defect in the tissue surface so that the substance is spread about the tissue surface and/or defect to the desired amount, which can be performed in multiple steps.

The device for applying a bubble of a substance to a tissue surface can optionally include one or more of the following features, in any combination: (a) wherein the substance can be a bioadhesive; (b) wherein the bubble surface comprises a retention ridge, lip and/or rim configured to support the bubble; (c) having a concave curved depression formed in the bubble support surface; (d) wherein the device can be configured to support a plurality of bubbles on the bubble support surface; (e) having a handle portion at a proximal end of the device, the handle portion configured to support at least the actuator and the source of expansion fluid; (f) wherein the device can be configured to form a bubble that comprises a spherically shaped film of the substance at least partially enclosing the expansion fluid advanced through the exit port; (g) wherein the device can be configured to form a bubble that comprises a spherically shaped film of the substance that only partially encloses the expansion fluid advanced through the exit port; (h) wherein the actuator comprises a compressible bladder configured to expel the expansion fluid from the source of the expansion fluid within the bladder through the expansion fluid passageway and the exit port; (i) wherein the expansion fluid actuator comprises a roller wheel moveable along a compressible bladder configured to expel the expansion fluid from the source of the expansion fluid within the bladder through the expansion fluid passageway and the exit port; (j) wherein the expansion fluid actuator comprises a syringe; (k) further having a substance supply channel configured to supply the substance to the distal tip of the device; (l) wherein the substance supply channel can be in fluid communication with a substance supply source; (m) wherein the substance supply channel can be integrated within the cannula; (n) wherein the substance supply channel comprises an elongate body having a proximal end and a distal end having distal tip with at least one opening therein, the elongate body being advanceable through the expansion fluid passageway to the distal tip at the distal end portion of the cannula; (o) wherein the substance supply channel can be internal to or surrounded by at least a portion of the expansion fluid passageway of the cannula; (p) wherein the cannula comprises an outer wall and an inner wall, the inner wall having the substance supply channel, and a space between the inner wall and the outer wall having the expansion fluid passageway of the device; (q) further having a second substance supply channel; (r) wherein the substance supply channel and the second substance supply channel each comprises a separate bioadhesive substance and/or activator; (s) wherein the bubble support surface can be beveled; (t) further having a substance dispenser; and (u) further having a cautery component configured to increase the temperature of at least the distal tip of the device.

In another aspect, a system for treating a defect on a tissue surface, having a first device for generating a bubble of a substance for treating a defect on the tissue surface, the first device having a first sleeve having a proximal end portion, a distal end portion, and an intermediate portion extending therebetween, a distal tip at the distal end portion of the first sleeve, the distal tip having an exit port extending through the distal tip, a fluid passageway extending through at least the intermediate portion and the distal portion of the first sleeve, the fluid passageway being in fluid communication with the exit port, and a supply of the substance.

The system for treating a defect on a tissue surface can optionally include one or more of the following features, in any combination: (a) wherein the device is configured to support a layer of the substance over the exit port in the distal tip when the first device is in an operable state; (b) wherein, when the first device is in the operable state, the first device can be configured such that passing a fluid through the exit port causes at least one bubble of the substance to form from the layer of the substance on the bubble support surface of the distal tip, the bubble having a spherically shaped film surface; (c) further having a second device for applying the bioadhesive substance to a retina, the second device having a second sleeve having a proximal end, a distal end, and a passageway extending along a length of the sleeve from the proximal end to the distal end of the sleeve, and an applicator having an elongate body and an applicator tip coupled with a distal end of the elongate body movable within the second sleeve, wherein the applicator portion can be self-expandable upon exit from the distal end of the second sleeve from a first collapsed state to a second expanded state, wherein the applicator tip has a larger width in the second expanded state; (d) wherein the system can be configured such that the at least one bubble can be transferred from the first device to the applicator tip of the second device and from the applicator tip of the second device to the tissue surface having the defect; and (e) further having a patch removably supported on a surface of the applicator tip, the patch being supported so that the at least one bubble can be transferred from the first device to the patch supported by the applicator tip of the second device and so that the patch can be transferred from the applicator tip of the second device to the tissue surface having the defect.

In another aspect, a method of repairing a defect in a retinal tissue, comprising advancing a substance supply device having a cannula and a distal tip toward the defect, providing a layer of a bioadhesive substance over an exit port in the distal tip of the device so that the layer of bioadhesive substance completely covers the exit port, forming a bubble of the bioadhesive substance on a support surface of the distal tip by advancing an expansion fluid through the exit port and the layer of bioadhesive substance, wherein the bubble can be at least partially attached to the support surface of the distal tip and has an approximately spherically shaped film that extends away from the support surface of the distal tip, and transferring the bubble to the retinal tissue so as to at least partially cover the defect in the retinal tissue.

The method of repairing a defect in a retinal tissue can optionally include one or more of the following features, in any combination: (a) transferring a plurality of bubbles of the bioadhesive substance to the defect and/or the retinal tissue adjacent to the defect; and (b) transferring the bubble to the retinal tissue so as to at least partially cover the defect in the retinal tissue comprises transferring at least one bubble of the bioadhesive substance to a first surface of the patch and positioning the patch over the defect so that the first surface of the patch having the bioadhesive substance thereon can be in contact with at least the retinal tissue adjacent to the defect.

In another aspect, a handheld device for applying a bioadhesive bubble to a retina, having a proximal end having a handle, a distal end having a distal tip, and an internal air fluid passageway from the proximal end to the distal end. The handheld device for applying a bioadhesive bubble to a retina can optionally include one or more of the following features, in any combination: (a) wherein the device can be configured to generate a bioadhesive bubble from a bioadhesive when a gas flows through the internal air fluid passageway; (b) wherein the device can be configured to maintain the bubble on the distal tip when the gas stops flowing through the internal air fluid passageway; and (c) wherein the device can be configured to release the bubble to the tissue of the retina when at least the bubble can be advanced into contact contacted against a tissue of the retina.

In another aspect, a handheld device for applying a bioadhesive substance to a retina, having a tubular body having a first end and a second end, an exit port at the second end, and a first passageway extending from the first end to the exit port, an elongate body having a loop at a distal end thereof, the elongate body being advanceable and retractable within the first passageway so that the loop can be extended out of the exit port and into contact with a tissue surface of the retina, and a source of a bioadhesive substance configured to be applied to the loop, wherein the device can be configured such that the bioadhesive substance can be applied to the loop and the bioadhesive substance can be transferred from the loop to the tissue surface of the retina by contacting the tissue surface of the retina with the bioadhesive substance that is on the loop.

In another aspect, a use of a system, device, or method of any of the foregoing aspects.

There is a need in the art for non-problematic, easy-to-use devices and methods for applying therapeutic substances to ocular or other biological tissue. Disclosed herein are systems, devices, and methods for applying a substance to a surface, such as for example and without limitation, for applying a bio substance to a tissue surface. Some nonlimiting examples of applications of any of the devices and methods disclosed herein include applying a bio-substance such as a bioadhesive to an ocular tissue such as for a retinal tear, hole, or detachment, and applying bioadhesive to the sclera, conjunctiva, and cornea, applying a bio-substance such as a bioadhesive to gastrointestinal tissue, colon tissue, etc. for sealing perforations or tears therein. However, the embodiments of the devices and methods disclosed herein are not limited to the delivery of therapeutic substances or ocular, medical, or biological applications. The devices and methods disclosed herein can be used for the delivery of any desired or suitable material in any desired application—biological, non-biological, mechanical, or otherwise.

Embodiments of devices and systems for applying a bioadhesive substance to a retina include an outer sleeve having a proximal end, a distal end, a passageway extending along a length of the elongate body, and an opening at the distal end of the elongate body, an applicator tip including an elongate body having a proximal end and a distal end, an applicator portion coupled with the distal end of the elongate body, and a substance supply lumen extending along a length of the device through which a bioadhesive substance can pass so that the bioadhesive substance can be applied to at least the applicator portion of the applicator tip. Some embodiments of the device can also have a source of the bioadhesive substance in fluid communication with at least the substance supply lumen.

Any embodiments of the devices, systems, and methods disclosed herein can include, in additional embodiments, one or more of the following features, components, and/or details, in any combination with any of the other features, components, and/or details of any other embodiments disclosed herein: wherein the applicator tip is configured to move between a first position wherein the applicator portion is contained within the outer sleeve and a second position wherein the applicator tip is positioned past the opening at the distal end of the outer sleeve; wherein the applicator portion can have a first width when the applicator portion is in the first position and a second width when the applicator portion is the second position, the second width being substantially greater than the first width; wherein the substance supply lumen is a passageway extending through at least the elongate body of the applicator tip; wherein the substance supply lumen can include a separate cannula positioned within the outer sleeve and extendable and retractable relative to the outer sleeve; wherein the substance supply lumen can be axially fixed relative to the outer sleeve and can have an opening that is adjacent to an end portion of the outer sleeve such that the bioadhesive substance can be exuded onto the applicator portion along at least a portion of a length of the applicator portion as the applicator portion is advanced distally; wherein the device includes a handle coupled with a proximal end of the outer sleeve; wherein the applicator portion can be biased such that a first side portion rolls toward a second side portion of the applicator portion when the applicator tip is withdrawn in the proximal direction into the outer sleeve; wherein the elongate body of the applicator tip extends through the outer sleeve to at least a proximal end of the device; wherein the elongate body of the applicator tip can be integrally formed with the applicator portion; wherein the applicator portion can be nonremovably coupled with the elongate body of the applicator tip; wherein the applicator portion can be configured to be removed from the patient's body with the device; wherein the applicator portion can be configured to be moved to the first position before the device is removed from the patient's body; wherein the applicator portion can be biased to collapse within the passageway of the outer sleeve when the applicator portion is withdrawn in the proximal direction into the outer sleeve; wherein the applicator portion can be biased such that a first side portion folds toward a second side portion of the applicator portion when the applicator tip is withdrawn in the proximal direction into the outer sleeve; wherein the applicator portion can be biased such that a first side portion collapses toward a second side portion of the applicator portion when the applicator tip is withdrawn in the proximal direction into the outer sleeve; and/or wherein the passageway through at least the elongate body of the applicator tip is in communication with an opening at a proximal end of the applicator portion.

Any embodiments of the devices, systems, and methods disclosed herein can include, in additional embodiments, one or more of the following features, components, and/or details, in any combination with any of the other features, components, and/or details of any other embodiments disclosed herein: wherein the passageway through at least the elongate body of the applicator tip is in communication with a plurality of openings passing through a first surface of the applicator portion; wherein the applicator portion can have an asymmetric shape such that a first side portion on one side of an axial centerline of the applicator portion can have a different shape than a second side portion on an opposite side portion of the applicator portion, the first and second sides being divided an axial centerline of the applicator portion; wherein the applicator portion can have an asymmetric shape having a first side portion on one side of an axial centerline of the applicator portion that can have a first length that can be longer than a second length of a second side portion on a second side of the axial centerline of the applicator portion; wherein the first side portion can have a first transition portion that has a first length in the axial direction and the second side portion has a second transition portion that has a second length in the axial direction, and wherein the first length of the first transition portion can be less than the second length of the second transition portion; wherein the applicator portion can have an asymmetric width; wherein the applicator portion can have an asymmetric thickness in a widthwise direction, such that a thickness profile of the applicator portion on a first side of the applicator portion can be different than a thickness profile of the application portion on a second side of the applicator portion; wherein the first side portion can be more flexible than the second side portion of the applicator portion; and/or wherein the applicator portion can be configured such that a first side portion contracts before a second side portion contracts when the applicator portion is withdrawn into the outer sleeve; wherein the applicator portion can have an asymmetric width and an asymmetric thickness.

Any embodiments of the devices, systems, and methods disclosed herein can include, in additional embodiments, one or more of the following features, components, and/or details, in any combination with any of the other features, components, and/or details of any other embodiments disclosed herein: wherein the outer sleeve can have a notch in the distal end thereof; wherein the outer sleeve can have a notch in the distal end thereof configured to facilitate contraction or reduction in size of the applicator portion as the applicator portion is being retracted into the distal end of the outer sleeve; wherein the notch can be generally in the shape of a "v" or can have a tapered shape that narrows in the proximal direction; and/or wherein the notch can be generally in the shape of a "u" or can have a uniform width and a rounded end portion at a proximal end of the notch.

Disclosed herein are embodiments of devices and systems for applying a substance to a tissue surface including a cannula comprising a proximal end, a distal end, and a passageway extending along a length of the cannula and an applicator tip. In some embodiments, the applicator tip can include an elongate body having a proximal end and a distal end, an applicator portion coupled with the distal end of the elongate body, a passageway through at least the elongate body of the applicator tip, a handle coupled with a proximal end of the cannula, and a source of the substance in fluid communication with at least the passageway extending along a length of the elongate body of the applicator tip.

Any embodiments of the devices, systems, and methods disclosed herein can include, in additional embodiments, one or more of the following features, components, and/or details, in any combination with any of the other features, components, and/or details of any other embodiments disclosed herein: wherein the applicator tip can be configured to move along a length of the passageway of the cannula between a first position wherein the applicator portion is contained within the cannula and a second position wherein the applicator tip extends past the distal end of the cannula; wherein the applicator portion can have a first width when the applicator portion is in the first position and a second width when the applicator portion is the second position, the second width being substantially greater than the first width; wherein the applicator portion can be biased to collapse within the passageway of the cannula when the applicator tip is withdrawn in the proximal direction into the cannula; wherein the substance can be a bioadhesive; wherein the tissue can include an eye tissue; wherein the applicator portion can be biased such that a first side portion rolls toward a second side portion of the applicator portion when the applicator tip is withdrawn in the proximal direction into the cannula; wherein the applicator portion can be biased such that a first side portion folds toward a second side portion of the applicator portion when the applicator tip is withdrawn in the proximal direction into the cannula; wherein the applicator portion can be biased such that a first side portion collapses toward a second side portion of the applicator portion when the applicator tip is withdrawn in the proximal direction into the cannula; wherein the passageway through at least the elongate body of the applicator tip is in communication with an opening at a proximal end of the applicator portion; and/or wherein the passageway through at least the elongate body of the applicator tip can be in communication with a plurality of openings passing through a first surface of the applicator portion.

Disclosed herein are embodiments of methods of repairing a defect in a retinal tissue, that can include advancing a device for applying a bioadhesive substance toward the defect, covering at least a portion of an applicator tip of the device with the bioadhesive substance, advancing the applicator tip past a distal end of an outer sleeve of the device, and transferring the bioadhesive substance from the applicator tip of the device to the defect. In some embodiments, the method can also include rolling or collapsing the applicator tip to a smaller size by withdrawing the applicator tip into the outer sleeve.

BRIEF DESCRIPTION OF THE DRAWINGS

FIG. 16A is a section view a non-limiting example of a device for providing an expansion fluid, the device comprising a roller wheel and a compressible bladder.

FIG. 16B is a top view of the device for providing an expansion fluid shown in FIG. 16A.

FIG. 17 is a section view of a non-limiting example of a device for providing an expansion fluid comprising a compressible bladder.

FIG. 18 is a top view of another non-limiting example of a device for providing an expansion fluid comprising a compressible bladder.

FIG. 50 depicts a side view of the embodiment of the device shown in FIG. 48, showing the device in a first or withdrawn state.

FIG. 51 depicts an end view of the embodiment of the device shown in FIG. 48, showing the device in the first or withdrawn state.

FIG. 52 depicts an end view of another embodiment of the device, showing the device in the first or withdrawn state.

FIG. 54A depicts a section view of another embodiment of a device for application of a substance to a surface of an object, showing the device in the second or deployed state.

FIG. 54B depicts a section view of another embodiment of a device for application of a substance to a surface of an object, showing the device in the second or deployed state.

FIG. 57 depicts a side view of another embodiment of a device for application of a substance to a surface of an object, showing the device in a second or extended state.

FIG. 58 depicts a side view of the embodiment of a device shown in FIG. 57, also showing the device in a second or extended state.

FIG. 65A is a perspective view of an end portion of an embodiment of a cannula that can be used with any embodiments of the devices disclosed herein.

FIG. 65B is a section view of the embodiment of the cannula shown in FIG. 65A, taken through line 65B-65B of FIG. 65A.

FIG. 65C is a top view of the embodiment of the cannula shown in FIG. 65A.

FIG. 66A is a perspective view of an end portion of another embodiment of a cannula that can be used with any embodiments of the devices disclosed herein.

FIG. 66B is a section view of the embodiment of the cannula shown in FIG. 66A, taken through line 66B-66B of FIG. 66A.

FIG. 66C is a top view of the embodiment of the cannula shown in FIG. 66A.

FIG. 77 is a perspective view of an end portion of another embodiment of a delivery device, showing an applicator in a retracted and collapsed state and a substance delivery cannula in a retracted state.

FIG. 78 is a perspective view of the end portion of the embodiment of a delivery device shown in FIG. 77, showing the applicator portion in a partially advanced position and expanded state.

DETAILED DESCRIPTION

Figure 1:
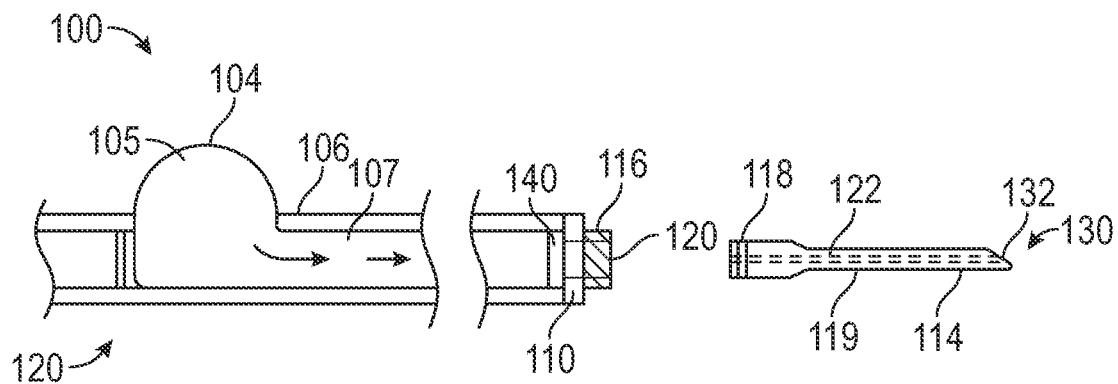
FIG. 1 is a side view of a non-limiting example of a device for providing a sub stance.

In the following detailed description, reference can be made to the accompanying drawings, which form a part hereof. In the drawings, similar symbols typically identify similar components, unless context dictates otherwise. The illustrative arrangements described in the detailed description, drawings, and claims are not meant to be limiting. Other arrangements may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

The arrangements disclosed herein comprise devices, systems, and methods for applying a substance to a surface, including tissue surfaces. In any arrangements disclosed herein, the substance can be a therapeutic substance which can be applied to a tissue. The tissue in any arrangements can be an ocular tissue. Examples of substances that can be used with any of the devices, systems, and methods disclosed herein include, without limitation, adhesives, bioadhesives, gels, hydrogels, thick liquids or semi-liquid treatment substances, double layer hydrogels, nonsolids and the like. As used herein, any use of the term substance is intended to include any of the types and examples of substances disclosed anywhere in this disclosure.

Any arrangements of the systems, devices, and methods disclosed herein can be configured to generate thin membranes of the substance for delivery to a biological tissue, including without limitation, an ocular tissue such as for a retinal tear or detachment, or intraocular, intra-abnominal, intracranial, epidermal bioadhesive delivery. However, the arrangements of the devices, systems, and methods disclosed herein are not limited to the delivery of substances to ocular, medical, or biological applications. The devices, systems, and methods disclosed herein can be used for the delivery of any desired or suitable substance in any desired or suitable application, biological, non-biological, mechanical, or otherwise.

Some arrangements include creating a bubble out of an adhesive, for example, blowing a bubble. The bubble can include a thin film that can be applied to a surface such as a retina, that can be either attached or detached from the back of the eye. In any arrangements, the bubble can be applied to the surface of the retina in an air-filled eye, or applied to the surface of the retina in a fluid-filled eye. Benefits of applying the bioadhesive in this way include an improved ability of the adhesive to conform to and stick to the eye and retina, and decreased or improved drying, curing, or activation time of the adhesive.

Arrangements of the devices and methods disclosed herein are configured to permit the creation of a bubble or plurality of bubbles in a controlled fashion, so that the release of the bubble or bubbles from the delivery device can be controlled so as to be not released until a time that is desired. Additionally, the devices and methods disclosed herein optionally are configured to permit the reformation of a bubble, or the new formation of a bubble, after the film has been removed and dissipated by the formation of bubble or bubbles during the preceding operation of the device, to make it ready for the next operation. The devices disclosed herein can optionally be configured to be used in any orientation, including but not limited to horizontal, vertical, inverted, or otherwise so as to enable use with any desired tissue, including eye tissue, walls or roof of mouth, nose, vagina, or other tissue.

As used herein, the term bubble can mean a complete, spherical membrane or body of the substance, a spherically shaped or curved shape or film of the surface, including without limitation a half sphere shape of the substance, a single bubble or a plurality of bubbles, either separate or connected together such as in a foam. All uses of the term bubble herein are meant to include any one or all of these examples of a bubble set forth herein or elsewhere within the description.

For example and without limitation, any of the devices disclosed herein can be configured to form a bubble, which means that the device can be configured to form a spherical membrane or body of the substance, a spherically shaped or curved shape or film of the surface, including without limitation a partial sphere or half sphere shape of the substance, a complete sphere of the substance, a single bubble or a plurality of bubbles, either separate or connected together such as in a foam.

In any arrangements disclosed herein, the bubble or the approximately spherical film of bioadhesive substance can have a diameter ranging from approximately 0.1 mm to approximately 15 mm or more (up to at least 100 mm), or from approximately 0.5 mm to approximately 5 mm, or from approximately 1 mm to approximately 3 mm, or from and to any values within these ranges.

Some arrangements relate to a system and/or a device for generating a bioadhesive bubble and/or applying a bioadhesive bubble to a surface. The surface can be a biological surface such as a retina. The system or device can optionally include an elongate body having a handle portion and a distal port. The elongate body can have a proximal end, a distal end, and an intermediate region extending therebetween. At least a proximal portion of the elongate body can include a handle portion. The distal end of the elongate body can have an exit port. In any arrangements, the elongate body, which can be a cannula as described in more detail below, can include at least one expansion fluid passageway or, optionally multiple (e.g., 2, 3, 4 or more) expansion fluid passageways extending partially or completely therethrough. The expansion fluid passageway(s) can be in fluid communication with the exit port and extend proximally toward the intermediate region of the elongate body.

In any arrangements, the fluid passageway can be configured to enable a supply of a fluid, which can be a gas or other expansion media, through the body of the device toward the exit port. The fluid passageway can be in fluid communication with the exit port. In any arrangements, a fluid such as a gas or other expansion media can be advanced through fluid passageway to exert a positive pressure on the substance to cause the substance to expand or form a curved or spherically shaped film or one or more bubbles from the substance.

The expansion media can, for example, inflate or otherwise expand a film or membrane of the substance (optionally, a bioadhesive substance) prior to application of the bioadhesive to a target tissue or tissue region. In some arrangements, the surgeon can activate the source of the expansion media (which can be a gas) and provide the expansion fluid through the expansion passage. The expansion fluid can be passed through the device and out through the opening at the distal end of the device through a substance to produce a bubble and/or spread a film of the substance on a desired surface.

FIG. 1 illustrates a non-limiting example of an application device 100 that can be used to provide a substance (including, for example and without limitation, a bioadhesive) to a target tissue. The device 100 can include a handle 102 comprising an expansion fluid source 104, which can optionally include an air bladder, that can be coupled with a body member 106 having a fluid passageway 107 extending therethrough. It shall be appreciated that other expansion fluid sources can be used, such as an air/gas supply line rather than an air bladder or any of the other types of expansion fluid sources disclosed herein or used in the industry, now or as later developed.

The expansion fluid source 104 can be filled with an expansion fluid 105 that can be used to generate the bubbles. The expansion fluid source 104 can be in fluid communication with the fluid passageway 107 so that the expansion fluid can be selectively released or communicated from the expansion fluid source 104 through the fluid passageway 107. The body member 106 can optionally be formed from a flexible, rigid, semi-rigid or other suitable material or component.

In any arrangements disclosed herein, the expansion fluid can include a gas such as air, sulfur hexafluoride (SF6), perfluoropropane (C3F8), and/or nitrogen or other inert gas, or any combination thereof. The expansion fluid can include a liquid such as water, a heavy liquid such as perfluoro-n-octane, a buffer, a solvent and/or an oil such as silicone oil. The expansion fluid enters and/or fills a bubble of bioadhesive substance, and/or causes the bubble to expand as the expansion fluid enters and/or fills the bubble. The expansion fluid can include 5-50%, 10-15%, 10-20%, 10-30%, 5-25%, 5-15%, 15-25%, 15-20%, 20-25%, 20%, about 20%, 12%, about 12%, 14%, about 14%, 12-14%, or 11-15% SF6. the expansion fluid can include 5-50%, 10-15%, 10-20%, 10-30%, 5-25%, 5-15%, 15-25%, 15-20%, 20-25%, 20%, about 20%, 12%, about 12%, 14%, about 14%, 12-14%, or 11-15% C3F8. For example, the expansion fluid may comprise 20% SF6, 12% C3F8, and 68% air, or the expansion fluid may comprise 20% SF6, 14% C3F8, and 66% air. The expansion fluid can also include a liquid such as water, a heavy solvent or liquid such as perfluoro-n-octane, an oil, or an oil-water mixture.

A connector 110 can be coupled with an end portion of body member 106 to enable the selective connection and disconnection of an end piece 114, which can be or include cannula. The connector 110 can include a connector portion 116 that can, optionally be threaded that is configured to reversibly couple with a proximal end portion 118 of the cannula 114. In any arrangements, the connector portion 116 can have an opening 120 or passageway therethrough that can be threaded and configured to threadedly engage with the proximal portion 118 of the cannula 114. In some arrangements, the opening 120 can have internal threads configured to engage with external threads on the proximal portion 118 of the cannula 114. Optionally, the connector 110 can have external threads thereon that are configured to engage internal threads on the inside of the proximal portion 118 of the cannula 114.

The connector 110 can optionally comprise a Luer lock connector, configured to reversibly connect with the cannula 114. The cannula 114 can have a generally uniform or consistent cross-sectional size along a length of the cannula 114. In some arrangements, as illustrated, the proximal portion of the cannula 114 can have an increased cross-sectional size or diameter as compared to an intermediate and distal portion of the cannula 114. The cannula 114 can have a passageway 122 therethrough that can be in fluid communication with the opening or passageway 120 in the connector 110 and the passageway 107 through the body member 106. The cannula 114 can have an end portion 130 (also referred to herein as a distal tip) having an opening 132 therethrough that is in fluid communication with the passageway 122 that extends through the cannula 114.

Additionally, the device 100 can optionally have one or more valves 140 such as a one-way valve or other flow restrictor at any location along a length of the passageway 107. The valve 140 can prevent the escape or inadvertent discharge of the expansion fluid 105 within the passageway 107 or expansion fluid source 104 and/or can be configured to prevent backflow into the source 104. One or more such valves can also be located in the cannula 114.

Note that the components shown in FIG. 1, and in some other figures are not be drawn to scale. For example, in other arrangements, the cannula 114 can be longer or shorter than what is shown in FIG. 1, or can have a larger or smaller cross-sectional size as compared to the example illustrated in FIG. 1.

In any arrangements, the connector 110 can be configured to engage with any of a variety of different cannulas 114. The variety of different cannulas 114 can have a range of different cross-sectional sizes and/or shapes, a variety of different lengths, and a variety of other different features and characteristics. With reference to the device 100 illustrated in FIG. 1, the distal tip 130 of the cannula 114 can be smaller or larger than as shown in FIG. 1 relative to one or more of the other components, including the connector 110 and the body member 106.

The cannula 114 can include a proximal portion or base 118, a distal tip 130, and a body 119 extending therebetween. As described, the cannula 114 can have an expansion fluid passageway 122 extending through the cannula body. The fluid passageway 122 can be configured to fluidically communicate with the exit port 130 and communicate an expansion fluid 105 through the expansion fluid passage 122 and exit port 132.

As the expansion fluid flows through the substance located in or on the distal tip 130 of the cannula 114, a bubble or curved film or membrane of the substance partially or completely enveloping or enclosing the expansion fluid can be generated. In some arrangements, the curved film or membrane of the substance can completely envelop the expansion fluid and can have a spherical shape. The surface(s) at the distal tip 130 of the cannula 114 (which can be, but is not required to be angled or beveled) can allow for a substance (which can be in the form of a bubble) to be removed from the cannula 114 and deposited on a target tissue (e.g., a retinal tear) with precision and with reduced risk of further tissue trauma. Additionally, any of the devices disclosed herein, including device 100, can be configured to maintain the bubble on the distal tip when the gas stops flowing through the expansion fluid passageway, and/or release the bubble when the bubble can be brushed against a retina or when the gas flows again through the expansion fluid passageway.

The distal tip can have at least one surface (referred to herein as the support surface or end surface) 131 configured to support a substance for the generation of a film of the substance and, subsequently, a bubble of the substance. The end surface 131 or surfaces, if multiple as in some arrangements, can optionally be beveled relative to a longitudinal axis of the cannula body and/or at least one cannula exit port. The at least one end surface 131 can be configured to support a film of the substance (which can be a bioadhesive in any embodiments disclosed herein). The film of the substance can be manipulated by a fluid advancing through the fluid passageway 122 to change from a first shape or configuration to a second shape or configuration having a spherical or curved shape, or being in the form of one or more bubbles of the substance. For example, in some arrangements, second state of the film can be formed when expansion fluid is selectively advanced through the fluid passageway 122 to the at least one cannula exit port 132 and/or through a substance contained within the handpiece or cannula, thereby generating an approximately spherical or curved film of the substance. In arrangements where the substance is in the form of a bubble in the second state, the bubble can enclose completely around a volume of the expansion fluid.

Figure 2:
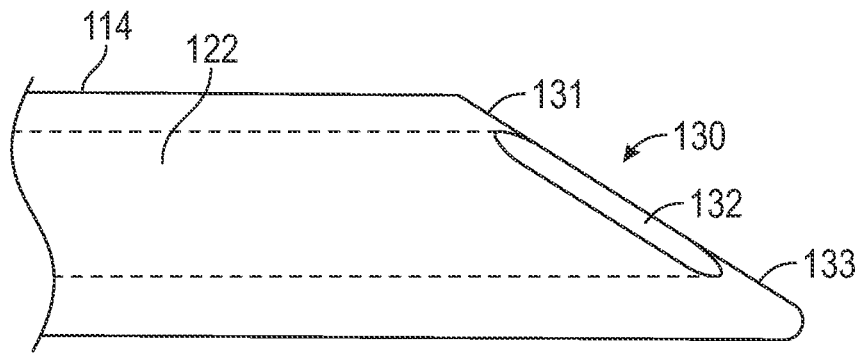
FIG. 2 is a side view of a distal portion of the device illustrated in FIG. 1.
Figure 3:
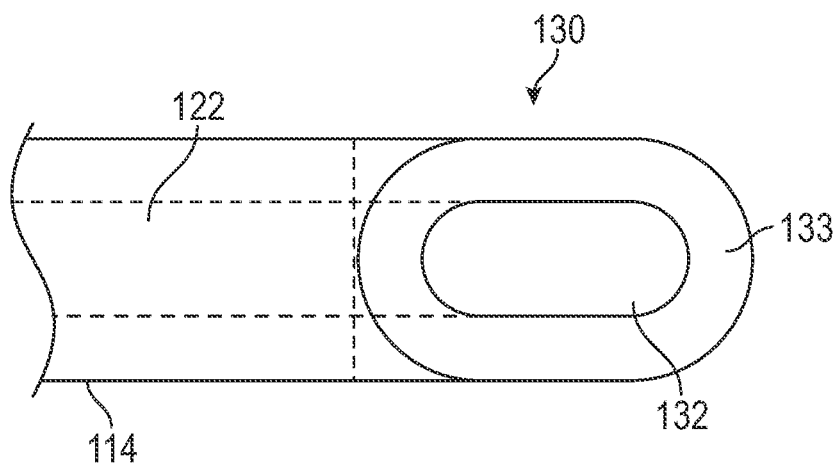
FIG. 3 is a top view of the distal portion of the device illustrated in FIG. 1.

The end surface 131 can be generally planar, as shown in FIG. 2. For example, FIG. 2 shows a side view and FIG. 3 shows a top view of a distal tip 130 comprising a flat beveled bubble port. The distal tip shown can also have a substance retention rim 133. The exit port 132 can be on the same plane as the end surface 131, and can be at an angle that is approximately 30 degrees, or approximately 40 degrees, or from approximately 30 degrees or less to approximately 45 degrees or more relative to a longitudinal axis extending through the cannula 114. As shown in FIGS. 2 and 3, the entire rim of the cannula exit port 132 can be in approximately the same plane as the end surface 131. The substance retention rim 133 of the end surface 131 can be configured to provide support for a bubble as the bubble forms, enlarges, and sits on the substance retention rim 133. The substance retention rim 133 can be configured to keep the substance from coming off the distal tip 130 when the device is being navigated toward a target tissue surface or an eye.

Figure 4A:
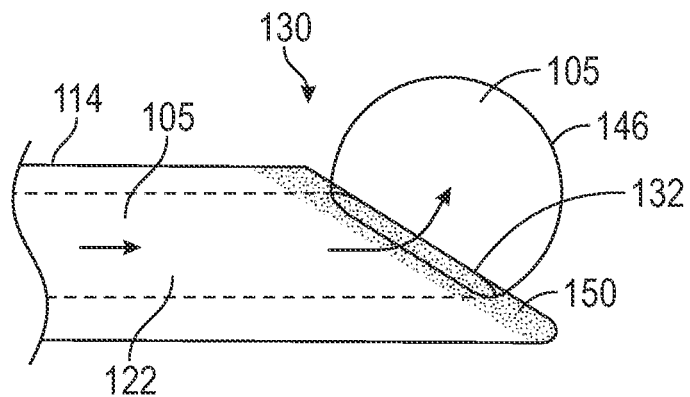
FIG. 4A is a side view of an example of a distal tip and a bubble formed from a substance.

FIG. 4A shows an example of a formation of a bubble 146 comprising a substance 150 filled with an expansion fluid 105 on the distal tip 130 of the device. A substance 150 is shown on a rim of the distal tip 130. The bubble was formed by passing an expansion fluid 105 through the distal opening 132 of the device, which was covered by a film or layer of the substance 150. As expansion fluid 105 is continued to be advanced through the distal opening 132, the film or layer can stretch and move into a spherical or bubble-like shape, with more substance 150 being drawn into the bubble or the existing substance stretching as the bubble is enlarged, such as is shown in FIG. 4A, the substance 150 being used to form the bubble 146. The bubble 146 is formed as expansion fluid 105 is advanced through the passageway 122 of the cannula 114 and through the distal port 132. The expansion fluid 105 fills the interior space within the bubble 146.

Figure 4B:
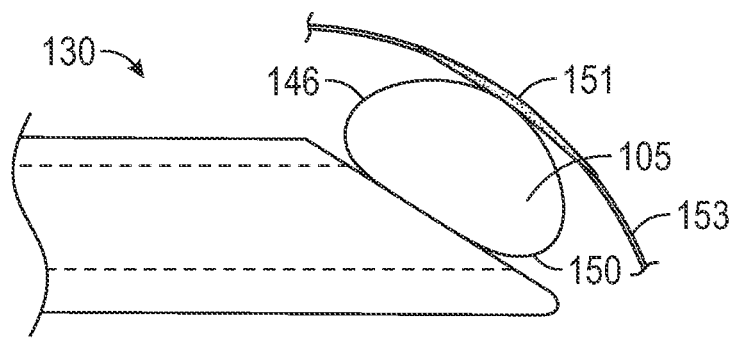
FIG. 4B shows the distal tip and bubble being advanced toward a desired treatment location.
Figure 4C:
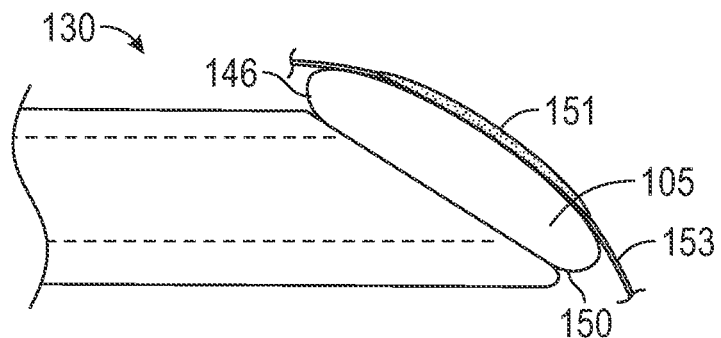
FIG. 4C shows the distal tip and bubble being pressed into contact with a defect in the target tissue or surface in the desired treatment location.

With the bubble 146 formed or enlarged to the desired size or wall thickness, the surgeon or user can then advance the distal tip 130 of the device having the bubble thereon to the desired treatment location, as shown in FIG. 4B. The distal tip 130 of the device can be used to advance the bubble 146 comprising the substance in a controlled fashion toward a defect 151 in the tissue or object surface 153, as shown in FIG. 4B. Thereafter, the bubble 146 can be pressed in further contact with the defect 151 (which can be a retinal defect) or surface 153 of the object by advancing the distal tip 130 further toward the defect to elongate the bubble and spread the substance over the defect 151 and target surface 153.

The bubble 146 and, hence, the substance 150 can thereafter be released from the distal tip in multiple different ways. For example, continued advancement of the distal tip 130 toward or against the target tissue surface and/or defect, or continued enlargement of the bubble, can cause the bubble to rupture against the target tissue surface. The distal tip can be made from a hydrophobic or other material configured to repel or reduce the surface tension of the substance relative to the distal tip so that at least a portion, or most or substantially all of the substance that was used to form the bubble can be deposited over the defect or against the target tissue surface. Additionally, as will be described below with reference to FIG. 43, an applicator device 1002 can be used to remove the bubble from the distal tip and/or apply or rupture the bubble against the defect or target surface. Further, in some arrangements, a movement of the distal tip relative to the target surface can exert a shear force on the bubble that can cause the bubble to burst or dissipate and deposit against the target surface. In some arrangements, a needle or other piercing element (both of which can optionally have a blunt or sharp end surface) or other suitable piercing instrument can be advanced either through the distal tip or separate from the distal tip toward the bubble to cause the bubble to burst against the target tissue surface. Further, any of the other devices or components described herein configured to facilitate the release of the bubble from the distal tip can be used to facilitate the release of the bubble from the distal tip.

Figure 4D:
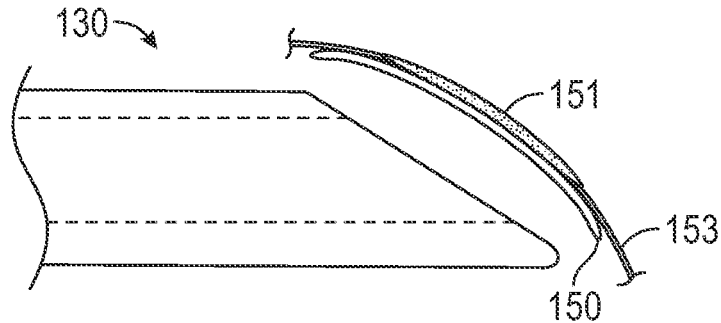
FIG. 4D shows the distal tip being withdrawn after the bubble has ruptured or dissipated, depositing the substance over the defect in the desired treatment location.

Optionally, the distal tip 130 of the device can be moved in close proximity to the defect or target location before the bubble is fully or even partially or substantially expanded so that the bubble can merely be expanded against the defect or target surface. Thereafter, as shown in FIG. 4D, the distal tip 130 can be retracted or withdrawn from the target location, leaving the substance 150 deposited against the target surface 153 so as to cover the defect 151.

Any arrangements of the device or methods disclosed herein can include a liquid reservoir or chamber, together with means for applying the liquid from said reservoir to the film retaining member (a ring or loop such as a flexible loop) or the distal end of the cannula to form a film thereon, whereby each time the device can be actuated and/or touched to the retina to remove the film, additional liquid to provide a new film may be applied to said ring to make the device ready for next use, by retracting the ring.

In any arrangements, the substance can be provided from reservoir that can be in the form of a cartridge, absorbable material, or chamber which may be detachably mounted on the device, integral to the device, or otherwise, or can be advanced into an internal passageway of the device, such as the expansion fluid passageway. The device can optionally be configured such that, when said cartridge or chamber is emptied, it may be readily replaced with a full cartridge, absorbable material or chamber of duplicate construction.

Figure 5:
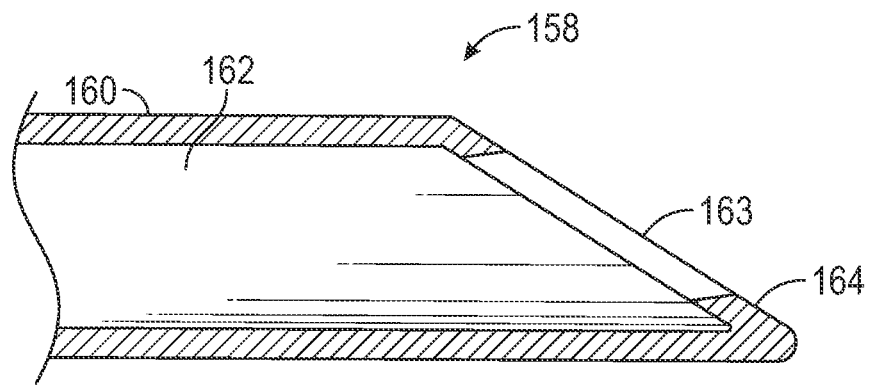
FIG. 5 is a section view of a distal portion of a non-limiting example of a substance supply channel.
Figure 6:
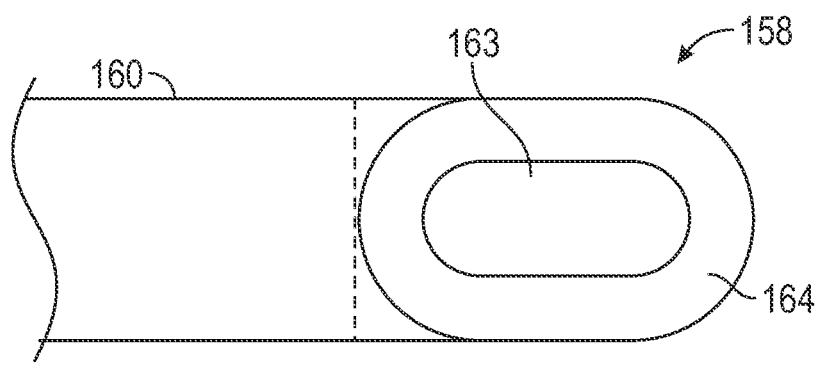
FIG. 6 is a top view of the distal portion of the substance supply channel illustrated in FIG. 5.
Figure 7:
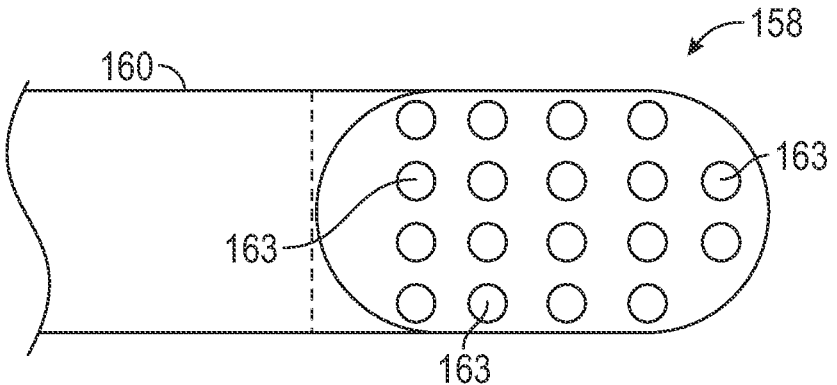
FIG. 7 is a top view of another non-limiting example of a distal portion of a substance supply channel.

Any arrangements disclosed herein can be configured to have a substance supply lumen or chamber within the handle portion and/or the cannula, or advanceable within the handle and/or cannula such as but not limited to cannula 114. The substance supply channel can be configured to advance the substance to the distal tip of the cannula, such as cannula 114. In some arrangements, as shown in FIGS. 5 and 6, the substance supply channel can have a separate elongate body portion that can be advanced distally through the expansion fluid passageway of the cannula to the distal tip of the cannula so that substance can be ejected out of the end of the substance supply channel onto the opening in the distal tip of the cannula to provide and/or replenish the substance that is on the distal tip for formation of bubble elements. The substance supply channel can optionally be advanceable and retractable within the expansion fluid passageway of the cannula as desired. In some arrangements, as shown in FIG. 7, one or a plurality of substance supply channels can be formed in a wall portion of the cannula so that a steady supply of the substance can be provided to the distal tip without requiring a separate device for doing so.

With reference to FIGS. 5 and 6, in some arrangements, the substance supply channel or tube 158 can have a separate elongate body 160 that can be advanceable within the expansion fluid passageway of the cannula (not shown in FIG. 5). The elongate body 160 can have a passageway 162 extending through the length of the elongate body 160 which can be in fluid communication with a distal opening or port 163. The distal port 163 can extend through the distal end 164 of the supply channel 158. The body portion 160 can therefore be sized and configured to be advanceable without restriction through the expansion fluid passageway of the cannula with which the supply channel 158 is configured to work with. For example, the elongate body 160 of the supply channel 158 can be approximately 20% smaller than the inner diameter of the expansion fluid passageway of the cannula, or from approximately 2% to approximately 20% or more, or from approximately 5% to approximately 10% smaller than the inner diameter of the expansion fluid passageway of the cannula. The distal end 164 of the supply channel 158 can have a shape and angle that approximately matches the shape and angle of an end portion of the inside surface of the inside of the expansion fluid passageway and internal surfaces of the inside of the cannula, and a size that is slightly smaller than the expansion fluid passageway.

The supply channel 158 can be advanced distally within the expansion fluid passage inside the cannula of the bubble generating devices so that the distal end 164 is adjacent to or in contact with the end of the internal passageway. Thereafter, the substance can be advanced through the one or more openings 163 to create a film across the distal port in the bubble generating device. The substance can be spread across the distal port in this fashion. The supply channel 158 can be used in this fashion to fill the tip of any cannula or device disclosed herein with the substance. The end surface may have multiple substance delivery holes (as shown in FIG. 7), or a single hole 163 as shown in FIGS. 5 and 6. Each hole may be large, for example and without limitation encompassing greater than 50% of the end surface 163 of the tip of the substance supply channel, or small, for example and without limitation encompassing 5-25%, or less than 50% of the end surface 164 of the beveled tip of the substance supply channel. Some arrangements can have five or more holes, or from 4 to approximately 10 or more holes in the distal end of the supply channel.

Some arrangements of the system, device, cannula, or distal tip comprise a space beneath the substance retention rim 133 and the substance supply channel 158. Said space can be configured to allow the bioadhesive substance to coalesce from the substance supply channel 158.

As mentioned above and as shown in FIG. 7, any arrangements of the supply channel disclosed herein can include a substance supply tip comprising any desired number of openings 163 at a distal end portion thereof, including one opening, two openings, three openings, four openings, five openings, six openings, seven openings, or up to twenty or more openings, or between five and ten openings, or any number of openings between any of the foregoing values. As mentioned, the substance supply channel can include a proximal end that extends into the fluid passageway of the cannula. The substance supply channel can be sized so that the expansion fluid can flow around an outside surface of the substance supply channel when the expansion fluid is blown through the fluid passageway of the cannula.

In some arrangements, the cannula can optionally include an outer wall and an inner wall, the inner wall comprising the substance supply channel, and a space between the inner wall and the outer wall comprising the expansion fluid passageway of the handpiece, the fluid passageway of the cannula body, or a fluid passageway of the cannula base or tip. The substance can optionally be advanced through the innermost lumen or inside the inner wall. The substance supply tip can include a surface that can be beveled as compared to a longitudinal axis of the substance supply channel body and the substance supply exit port, per any of the details of the other beveled tips disclosed herein or otherwise.

Figure 8:
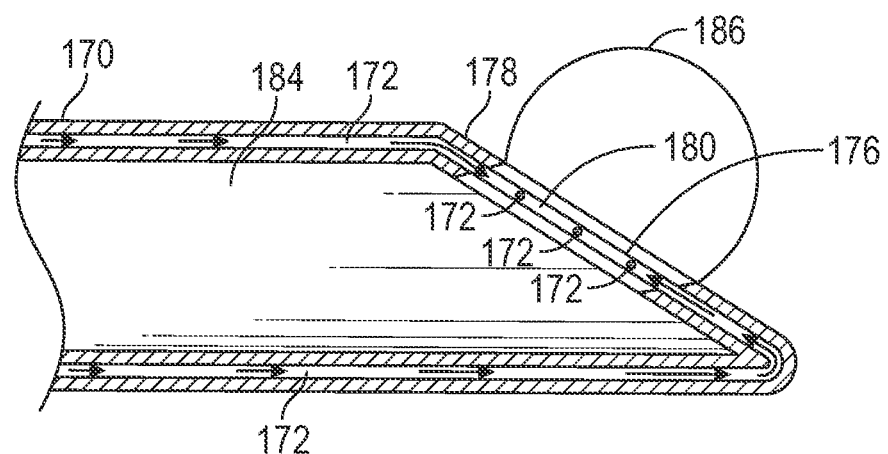
FIG. 8 is a section view of another non-limiting example of a device for providing a substance.

Another example of a cannula 170 having an internal substance supply passageways 172 is shown in FIG. 8. The cannula 170 can have a plurality of substance supply passageways 172 that can, optionally, be integrally formed with the cannula, extending through the cannula 170 that are configured to permit passage or advancement of the substance from a proximally located source of substance or substance reservoir to the opening 176 in the distal dip 178. The arrows through the substance supply passageways 172 in FIG. 8 illustrate a direction of flow of the substance through the substance supply passageways 172 when the surgeon or user advances the substance through the substance supply passageways 172. The substance supply passageways 172 can optionally be in communication with a manifold 180 surrounding the opening 176 in the distal tip 178. The manifold 180 can be sized and configured to create a film or membrane of the substance across the opening 180 in the distal tip 178 when the substance is advanced through the passageways 172 so that, when an expansion fluid is advanced through the expansion fluid passageway 184 of the cannula 170, a bubble 186 can be formed from the film or membrane of the substance. The manifold 180 can have a series of radially inwardly projecting openings, an open annulus, openings or jets that can be configured to facilitate the formation of the film of substance. The cannula 170 can be formed as a unitary piece, or from multiple pieces coupled together. The opening 176 can be sized and configured to ensure the consistent formation of bubbles when an expansion fluid is passed through the substance, and/or the consistent formation of a membrane of the substance supplied through the passageways 172.

Figure 9:
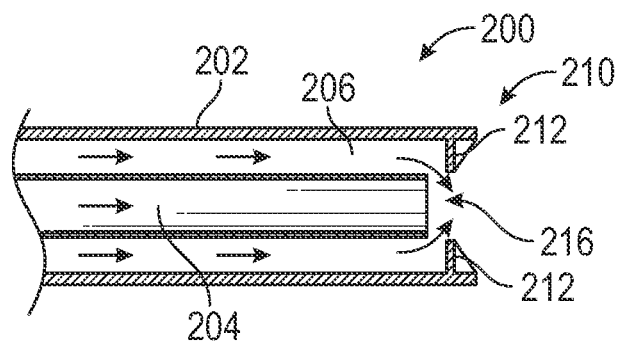
FIG. 9 is section view of another non-limiting example of a distal portion of a device for providing a substance.

As described, any arrangements of the devices disclosed herein can be configured so that the substance supply channel surrounds at least a portion of the expansion fluid passageway of the handpiece, the fluid passageway of the cannula body, and/or a fluid passageway of the cannula base or tip. As illustrated in FIG. 9, for example, device 200 can have an elongate body portion 202 having an expansion fluid passageway 204 extending therethrough. The expansion fluid passageway 204 can be partially or completely surrounded by a substance supply channel or lumen 206 that can be used to advance the substance to the distal tip 210 of the device 200. The lumen 206 can be a single annular lumen or can comprise one or a plurality of openings all in communication at a proximal and a distal end or portion of the lumen 206. In some arrangements, a deflector or deflectors 212 can be positioned at a distal end of the lumen 206 and be configured to direct the flow of substance radially inwardly toward the opening 216 in the distal end of the device 200. The deflector can optionally have an annular shape. The deflector can be angled inwardly at an angle that is less than approximately 90 degrees, or have a ramped surface to provide a more efficient flow pathway of the substance toward the opening 216.

Figure 10:
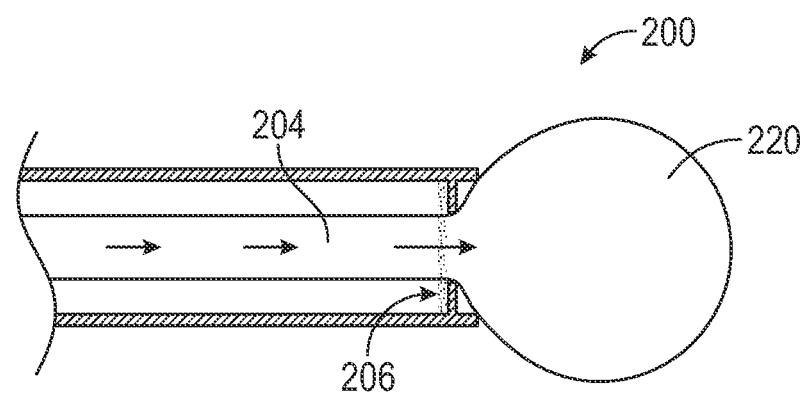
FIG. 10 is section view of another non-limiting example of a distal portion of a device for providing a substance, showing a bubble formed from a substance.

The device 200 can optionally include a continuous (360 degree) circumferential deflector member 212 or a plurality of discrete deflector members. The deflector member can be configured to allow for longer retention of the bubble on the tip of the cannula. This configuration allows fluid to flow around the expansion fluid (which, in any arrangements disclosed herein, can be air, sterilized air, or another inert gas, or the other fluids described herein) and form a film of substance at the cannula exit port 216. After the film has been formed, the expansion fluid can be advanced against the film to cause a bubble to be formed. FIG. 10 illustrates a bubble being formed from the film of substance advanced through the substance supply channel or lumen 206. The bubble may be supported by a flared opening.

In other arrangements, the substance supply channel can include a tube or cannula that can be advanced within the expansion fluid passageway 362 of the handpiece, the fluid passageway of the cannula body, or a fluid passageway of the cannula base or tip. The substance supply channel tube can be advanced to be in contact with or within the distal tip toward the cannula exit port. The substance supply channel tube can have a distal end that reaches near the cannula exit port.

Any arrangements of the system and/or device disclosed herein can further have a second substance supply channel. The substance supply channel and the second substance supply channel each can include a separate bioadhesive substance, for example a polyethylene glycol solution and a trilysine amine solution, hydrogel, double layer hydrogel, or polymeric hydrogel.

The at least one end surface can be configured to support a bioadhesive bubble. The end surface, retention ridge, lip, or rim can include a flat surface configured to hold and/or maintain a bioadhesive bubble. The distal tip and/or the end surface of the distal tip can include a retention ridge, lip, or rim comprising a flat surface configured to hold and maintain the bioadhesive bubble.

The end surface of the distal tip can have a 1-15°, 15-30°, 30-45°, 45-60°, 60-75° angle relative to a square end (in either direction), or an angle in a range comprising more than one of the aforementioned angle ranges, compared to the longitudinal axis of the cannula body and/or at least one cannula exit port. The angle of the end surface can be configured to enhance retention of the bioadhesive bubble so the bubble can be kept from falling off.

The distal tip of some arrangements can be configured to not have a bevel. For example, the distal tip may comprise a flat or square surface with a cannula exit port at 90° in relation to the longitudinal axis of the cannula body, or the distal tip may be rounded and/or blunt without a flat surface.

Any arrangements of the distal tip and/or the end surface of the distal tip can include a retention ridge, lip, or rim for retaining or supporting a bubble thereon. Additionally, the size, angle and/or shape of the distal tip (such as distal tip 130 or any other distal tips disclosed herein) and the retention ridge, lip, or rim thereof can be based on the application and on other factors related to the substance, including without limitation the viscosity of the substance. For example, the substance retention rim 133 may be thinner (e.g. 1 mm) for a viscous substance than for a non-viscous substance (e.g. 2.5 mm). In other arrangements, the substance retention rim 133 can be thicker when configured for a substance with lower viscosity than for a higher viscosity substance. The cross-sectional shape of the port 132 can optionally be round, square, ovular, rectangular, triangular, pentagonal, hexagonal, star shaped, or otherwise. The shape can be selected based on the viscosity of the bioadhesive substance and the size or other parameters of the desired bubble or bubbles, or foam to be formed.

The end surface 131 can be flat, curved, or otherwise, and can have a depression formed therein sloping toward the opening 132. The depression can be angled inward and can have a flat cross-sectional profile or be curved. Any arrangements disclosed herein can have a plurality of openings 132 formed in the distal end portion to enable the simultaneous formation of a plurality of bubbles of the substance, or to form a foam-like structure of the substance. Any arrangements can have two or more openings, or from two to approximately twenty or more openings, or from four to twelve openings, or from and to any values within these ranges.

Figure 11:
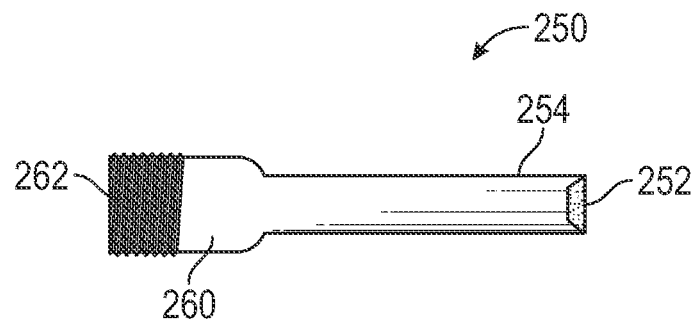
FIG. 11 is a side view a non-limiting example of a cannula.
Figure 12:
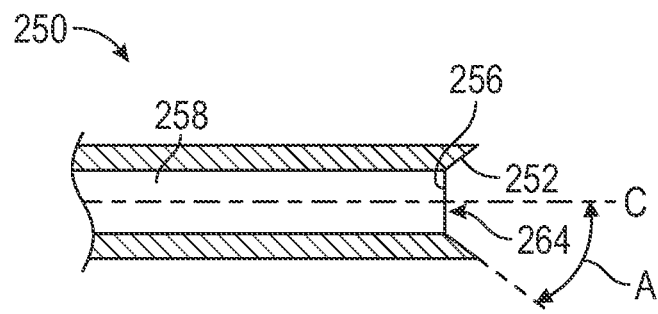
FIG. 12 is a section view of a non-limiting example of a distal tip.

FIGS. 11 and 12 illustrate another arrangement of a cannula 250. The end surface 252 of the distal tip 254 of the cannula 250 can optionally be circular, ovular, non-circular or otherwise. For example, the distal tip 254 can optionally be round, square or rectangular shaped. Additionally, the distal tip 254 can have a non-planar end surface 252 such as is shown in FIGS. 11 and 12. The end surface 252 can be angled inward toward a center of the cannula 258. The end surface 252 can have a bevel or angle formed around the opening 256. The opening 256 can be in fluid communication with an expansion fluid passageway 258 through the cannula 250. The end surface 252 can be at an angle A (as shown in FIG. 12) that is approximately 45 degrees relative to the longitudinal axis C (as shown in FIG. 12), or from approximately 30 degrees or less to approximately 90 degrees or more, or from approximately 40 degrees to approximately 70 degrees, or from approximately 50 degrees to approximately 60 degrees relative to the longitudinal axis C, or to and from any values within these ranges.

Additionally, the cannula 250 can have a hub or hub portion 260 and connector threads 262 on an external surface (as shown) or internal surface thereof. The cannula can optionally include a solid cannula wall, a core or cannula fluid passageway 258 through which a substance supply channel or an expansion fluid can be advanced, an opening or cannula exit port 256 at the tip of the cannula, and a space 264 configured to maintain a film of substance such as a bioadhesive substance. As with any arrangements disclosed herein, the cannula 250 can be dipped into a substance dispenser as described below for adding the substance to the distal tip of the cannula, and can retain the bioadhesive substance as a film in the space 264 at the tip.

Accordingly, in any arrangements, the end portion of the cannula (whether beveled, square, or otherwise) can have a concave or inwardly curved depression formed in the end surface thereof. Alternatively, in any arrangements, the end portion of the cannula (whether beveled, square, or otherwise) can have a convex or outwardly curved depression formed in the end surface thereof. The end surface may be flared or flanged at the end, and/or include a space that holds or provides greater surface area to the bioadhesive substance. An advantage of the flared or flanged surface is that it can retain a film of the bioadhesive substance that forms a bubble when a gas such as air blows into and/or against the film.

Some arrangements of the distal tip can have multiple end surfaces. Some arrangements of the distal tip can have no more than one end surface, while in other arrangements, a plurality of end surfaces are used. The distal tip can be blunt or rounded, or can include a blunt or a rounded end.

Figure 13:
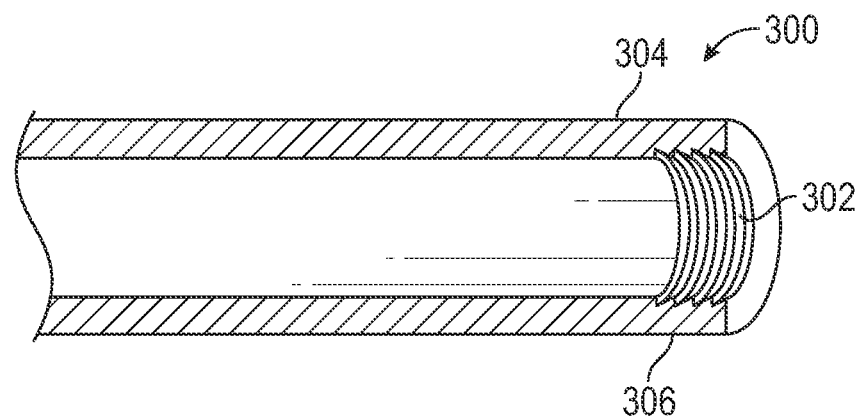
FIG. 13 is a section view of a non-limiting example of an interior of a distal tip with grooves.
Figure 14:
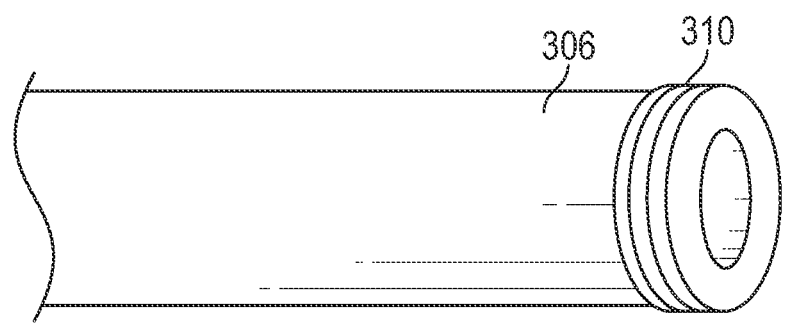
FIG. 14 is a side view a non-limiting example of an exterior of a distal tip with grooves.

The tip can include one or more grooves at, for example, the distal tip. An advantage of having grooves at the distal tip is that the one or more grooves may help retain bioadhesive substance and aid in bioadhesive substance bubble formation. The distal tip can include one to ten, or from three to six (for example, five) grooves, or any number of grooves within that range or more in any of the same numbers. The distal tip can include an inner surface comprising the grooves. For example, FIG. 13 illustrates a side view of another arrangement of a cannula 300 having a plurality of grooves 302 formed on an inside surface of the distal tip 304. The distal tip 304 can optionally include an outer surface 306 also or alternatively having one or more grooves 310, as illustrated in FIG. 14, which is a side view of a distal tip having a plurality of grooves 310 on an outside surface of the distal tip. Any arrangements can have ridges, grooves, or other patterns of protrusions and/or depressions on the inner or outer surface of the tip of the cannula, optionally including the end surface, to help retain substance within and/or on the tip of the cannula. The ridges, grooves, or other patterns may be configured to retain the bubble or hold the bubble in place.

In any arrangements, the cannula, cannula base, cannula body, and/or distal tip can have a cross sectional diameter that is from approximately 0.1 mm to approximately 10 mm or more, or from approximately 1 mm to approximately 4 mm, or from approximately 1.5 mm to approximately 2 mm, or to and from any values within these ranges. In some arrangements, the cannula, cannula base, cannula body, and/or distal tip can have a cross sectional diameter that is from 0.1-0.5 mm, 0.5-1 mm, 1-2 mm, 2-3 mm, 3-4 mm, 4-5 mm, 5-6 mm, 6-7 mm, 7-8 mm, 8-9 mm or 9-10 mm. The cannula, cannula base, cannula body, distal tip and/or cannula exit port can have a length of approximately 0.1-0.5 mm, 0.5-1 mm, 1-2 mm, 2-3 mm, 3-4 mm, 4-5 mm, 5-6 mm, 6-7 mm, 7-8 mm, 8-9 mm, 9-10 mm, 10-20 mm, 20-30 mm, 30-40 mm or 40-50 mm. The cannula, cannula base, cannula body, distal tip and/or cannula exit port can include an external diameter, an internal diameter and a width between the internal diameter and the external diameter, each being one of 0.01-0.05 mm, 0.05-0.1 mm, 0.1-0.5 mm, 0.5-1 mm, 1-2 mm, 2-3 mm, 3-4 mm, 4-5 mm, 5-6 mm, 6-7 mm, 7-8 mm, 8-9 mm, 9-10 mm, 10-20 mm, 20-30 mm, 30-40 mm or 40-50 mm any of the components or features disclosed herein can have any suitable or typical size, including without limitation any size within any ranges stated herein.

The retention edge, ridge, or lip can be 0.1-0.5, 0.5-1, 1-2, 2-3, 3-4, 4-5, or 5-10 mm thick. The retention edge, ridge, or lip, the retention edge, ridge, or lip can be 0.1-0.5, 0.5-1, 1-2, 2-3, 3-4, 4-5, or 5-10 mm long. Some arrangements include a retention edge, ridge, or lip that can be set back a short distance from the very tip of the cannula. The distal tip may or may not have a central air tube.

In any arrangements, the opening can be at the very tip of the distal end. Optionally, the opening can be on the side of the tip of the distal end. The opening can be on the side of the distal end, but more proximal than the tip of the distal end.

Figure 15:
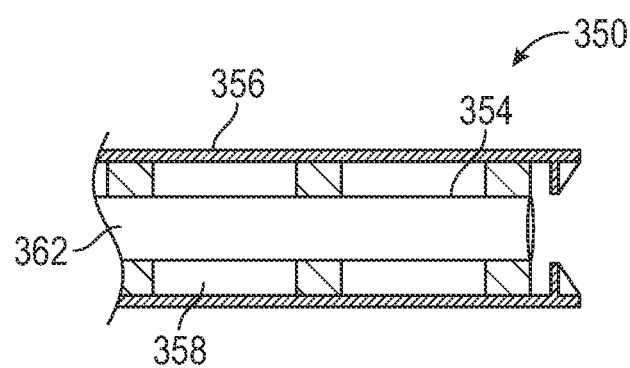
FIG. 15 is a section view of another non-limiting example of a distal tip.

Some arrangements of the system and/or device include circumferential or non-circumferential intermittent support structures. The intermittent support structures can connect the outer wall to the inner wall. Some arrangements can include 1, 2, 3, 4, 5, 6, 7, 8, 9, 10, 11, 12, 13, 14, 15, 16, 17, 18, 19, 20, or from 4 to 10, or any number of circumferential and/or non-circumferential intermittent support structures. Some arrangements comprise circumferential or non-circumferential intermittent support structures connecting the outer wall and the inner wall, for example 1, 2, 3, 4, 5, 6, 7, 8, 9, 10, 11, 12, 13, 14, 15, 16, 17, 18, 19, 20, any number therebetween, or more circumferential and/or non-circumferential intermittent support structures. FIG. 15 shows an example of a distal tip 350 comprising intermittent attachments or support structures 352 between a central tube 354 and an outer tube 356. The support structures can be configured to permit fluid passage around such structures.

The handpiece or cannula can include an outer wall and an inner wall, and a space such as space 358 of cannula 350 between the inner wall and the outer wall. The space between the inner wall and the outer wall can comprise a substance supply channel. The inner wall can bound the expansion fluid passageway 362 of the handpiece, the fluid passageway 362 of the cannula body, or a fluid passageway 362 of the cannula base or tip.

In any arrangements, the expansion fluid can be provided from a source separate from the device, or from a reservoir or cartridge or absorbent material within the device, or built into the device. As described, any arrangements can have a fluid passageway through which gas can be advanced from the source. The device can optionally have a connector such as a port at the proximal end to which tubing or other conduit may be attached to allow pressurization of contents (such as the expansion fluid) within the device, in the presence or absence of a plunger or mobile plug. The handpiece or device in any arrangements disclosed herein can include an expansion fluid actuator. The expansion fluid actuator can be coupled with a proximal end of the device so as to be in fluid communication with the expansion fluid passageway. The expansion fluid actuator can be configured to be activated or moved by a user. The moving component can be configured such that an actuation of the moving component by the user causes flow or movement of the expansion fluid through the expansion fluid passageway, such as from the proximal end to the exit port of the distal end. The handpiece can include an expansion fluid actuator connected at the proximal end to the expansion fluid passageway, and configured to be engaged by a user, wherein said engagement can cause movement of the expansion fluid through the expansion fluid passageway from the proximal end to the exit port of the distal end.

The expansion fluid actuator can optionally include a roller wheel or roller ball that can be moveable forward and backward in order to advance or withdraw, respectively, a fluid through expansion fluid passageway. In this configuration, a roller wheel device can include a plurality of movable ribs or spokes coupled with a cylindrical outer surface that are configured to rotate about a center axis. In any embodiments disclosed herein, the roller wheel can be configured to expel the expansion fluid from the bladder through the expansion fluid passageway from the proximal end to the exit port of the distal end when the roller wheel is rolled or moved along a length of the tube or chamber by, for example, a person's finger, a small motor, a coil spring, or otherwise.

A non-limiting example of an expansion fluid actuator 500 that can be used with any of the device arrangements disclosed herein is shown in FIGS. 16A and 16B. The actuator 500 can have a roller wheel 502 configured to move along a length of the expansion fluid conduit 504 and to squeeze the expansion fluid conduit 504 so as to flatten and/or collapse the expansion fluid conduit 504 as the roller wheel 502 moves along the length of the expansion fluid conduit 504. As this occurs, the roller wheel 502 can force fluid within the passageway 506 in the distal direction, toward the distal tip of the cannula where the fluid can contact a film of substance such as a bioadhesive and create a bubble. The conduit 504 can be made from the resilient tubing material or even a non-resilient single use tubing material that collapses as the roller wheel 502 advances along the length of the conduit 504. In any arrangements, the roller wheel 502 can roll in both a distal direction and a proximal direction, withdrawing air back into the passageway 506 as the roller wheel is moved in the proximal direction. The actuator 500 can optionally also include a second roller coupled with the first roller wheel that can be joined with an roll together with the first roller so as to exert an opposing force on the tubing that squeezes the tubing between the first and second rollers. Some arrangements include a roller ball that can be moveable forward and backward, or in any restricted or unrestricted fashion 360 degrees around a point or axis.

Some arrangements include a fixed device where a bladder moves relative to a ball, sphere, stopper, plunger, or other stoppage device. For example, some such arrangements include a port in the handle configured to receive an adhesive substance into the handle, where a bladder containing the adhesive can be configured to be moved from a distal to a proximal direction, and the ball creates a barrier to the contents of the bladder, thus causing expulsion of the bioadhesive through the distal end of the device. Some arrangements include a bioadhesive packet that may be loaded into the device.

As described, the handpiece can further have a source of an expansion fluid, which can include an expansion fluid actuator, connected at the proximal end to the expansion fluid passageway. The expansion fluid actuator can be configured to be engaged, directly or indirectly, by a user, wherein such engagement can cause movement of the expansion fluid through the expansion fluid passageway from the proximal end to the exit port of the distal end. In some arrangements, the expansion fluid actuator can include a compressible bladder, syringe, a collapsible vial or other reservoir, such as an accordion type collapsible reservoir, or other similar device configured to expel the expansion fluid from the bladder through the expansion fluid passageway from the proximal end to the exit port of the distal end of the device. In some arrangements, the expansion fluid actuator can have a roller wheel moveable forward and backward, and be configured to expel the expansion fluid from the bladder through the expansion fluid passageway from the proximal end to the exit port of the distal end.

In still additional arrangements, the expansion fluid actuator can have a sliding piece, such as a plunger, etc. In some arrangements, the expansion fluid actuator can include a syringe filled with an expansion fluid, such as air. Optionally, the expansion fluid actuator can comprise a compressed fluid or gas cartridge, such as a compressed air cartridge that can be fluidically coupled with the expansion fluid passageway. A trigger, valve, stopcock, or other device or component can be used to control the flow of air from the compressed air cartridge into the expansion fluid passageway.

The expansion fluid actuator can optionally include a compressible bladder. The compressible bladder can be configured to expel the expansion fluid from the bladder through the expansion fluid passageway from the proximal end to the exit port of the distal end. The expansion fluid actuator can include a compressible bladder configured to expel the expansion fluid from the bladder through the expansion fluid passageway from the proximal end to the exit port of the distal end. The compressible bladder can have a diameter that extends out from the center of the handle 1-1.5, 1.5-2, 2-3, 3-4 or 4-5 times a diameter of another portion of the handle such as the elongate body, on one or more sides of the handle or elongate body. For example, the compressible bladder may extend 1, 2, 3, 4, 5, 6, 7, 8, 9, 10, 10-15, 15-20 or more from a side of the handle or elongate body of the handle. The compressible bladder can include any flexible material such as rubber, plastic, a flexible metal, or an elastic material.

FIG. 17 shows a side view of an embodiment of an expansion fluid actuator 520 that can be used with any of the device arrangements disclosed herein to provide an expansion fluid to a distal end or tip of the cannula and, hence, to the substance to form a bubble. The arrangement of the fluid actuator 520 illustrated in FIG. 17 can include a compressible bladder 522 having an internal air space 523 that is in fluid communication with an expansion fluid passageway 524 of and expansion fluid channel 526. The air bladder 522 can extend or protrude away from one side of the handle such as from the top of the handle so that a user can exert a force F in generally one direction so as to collapse the air bladder 522 and to force an expansion fluid to advance through the expansion fluid passageway 524. The actuator 520 can have a support or support surface for the compressible bladder on the bottom of the compressible bladder. The support for the compressible bladder may comprise the handle of the device or system, or an intermediate support structure, depending on the arrangement. The air bladder can be compressible, for example, with a person's finger to force air from the bladder.

Some arrangements can include an actuator mechanism provided with a compression device comprising a normally expanded, resilient air storage bulb, thus forcing air distally through an air tube toward a distal tip of a cannula or through a bubble-making ring at the end of the device. Some arrangements can include a trigger mechanism that compresses the air storage bulb from one side. Some arrangements include a trigger mechanism that compresses the air storage bulb from more than one side simultaneously. The bulb may be made of a material which can be sufficiently resilient to return the trigger to its normal position, but if desired a small coiled spring may be associated with the trigger to maintain the trigger in a normal inactive position and to return the same to such position after each operation.

The device can include a cannula and an associated distal tip, separate from the bubble generating portion of the device, that permits the blowing of air onto the retina to create a drying effect, prior to application of the bubble. In some arrangements, the device can be configured to permit the device to blow air through the distal tip of the cannula without the presence of a substance so that air can be blown onto the target tissue.

FIG. 18 shows another arrangement of an actuator 540 that can be used to advance the expansion fluid toward the distal end of a cannula of any of the arrangements of devices disclosed herein. In any arrangements, the actuator 540 can have a bladder 542 having the volume of space 543 therein that is in fluid communication with the passageway 544 through an expansion fluid conduit or channel 546. The bladder 542 can be arranged with flexible ribs or struts, corrugations, or otherwise to improve the flexibility and collapsibility of the bladder. The ribs can be configured to help the bladder 540 retain its shape and elasticity, and/or to bias the bladder to return to an expanded shape. The ribs can be made of the same material as another portion of the compressible bladder, or as the rest of the compressible bladder, or may be made of another flexible material.

In any arrangements, the actuator 540 can have one or more one-way valves in fluid communication with the bladder so that air can refill the bladder when the bladder is released and allowed to expand back to its original expanded state, and to prevent air from sucking back from a distal portion of the conduit 546 back into the bladder 542. The bladder 542 can be sized to have any desired volume of expansion fluid contained within the bladder 542. The bladder 542 may be squeezed or otherwise compressed in any direction to expel the expansion fluid toward the distal tip.

In some arrangements, the bladder 542 can be spherical or generally spherical and extend in all directions radially away from the centerline of the conduit 546. In other arrangements, the bladder 542 can have a semi-spherical shape, or any other desired shape.

Any arrangements of the systems and/or devices disclosed herein can include a separately or electrically powered means for advancing the expansion fluid through the expansion fluid passageway of the handpiece or through the expansion fluid passageway of the cannula. For example, the expansion fluid passageway can include a proximal end connected to a tube, channel, or other passageway connected to and configured to receive expansion fluid from an expansion fluid receptacle. The receptacle can include a valve. Said valve can be configured to open by operation of a button on the handpiece of the system or device, or by operation of a foot pedal. Said valve can be configured to open by manual operation such as through operation of a screw handle.

In any arrangements, the expansion fluid actuator can include a sliding piece. The sliding piece or other expansion fluid actuator can be configured to move a plunger, such as a plunger toward the distal end of the device. Movement of the plunger can force the expansion fluid through the expansion fluid passageway and/or exit port of the handpiece, and/or through the cannula expansion fluid passageway and/or cannula exit port of the cannula to produce the bubble.

Figure 19:
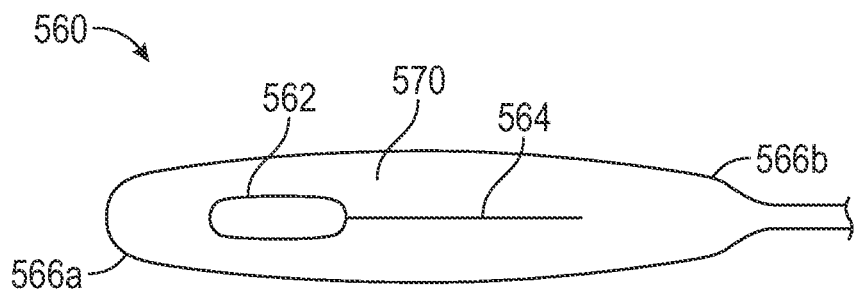
FIG. 19 is a top view of a non-limiting example of a device for providing an expansion fluid comprising a moveable slider.
Figure 20:
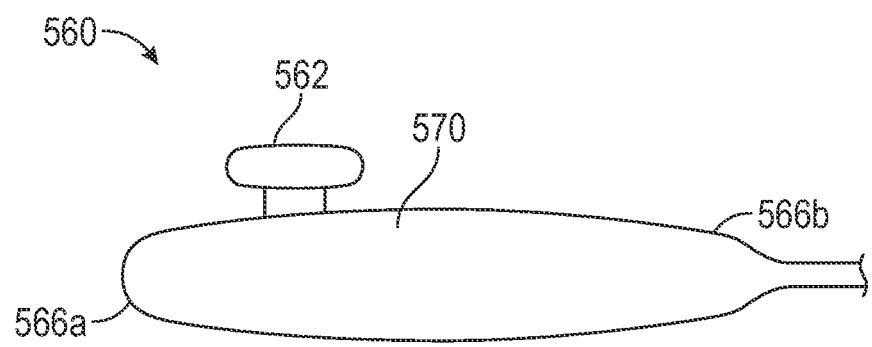
FIG. 20 is a side view of the device for providing an expansion fluid comprising a moveable slider.

FIGS. 19 and 20 show a non-limiting example of an expansion fluid actuator 560 comprising a sliding piece 562. The sliding piece 562 can include a moveable part or slider 562, where the moveable slider 562 can be coupled with a sealed diaphragm, a piston, a plunger or other similar component located within the chamber 570 of the actuator 560 that can move with the movement of the slider 562 so as to change a volume of space within the chamber 570. The chamber 570 can optionally have a general cylindrical shape at least in a middle portion thereof. The slider 562 can be configured to be movable along a pathway or groove 564 from a proximal end 566a to a distal end 566b of the device, thereby expelling air or expansion fluid through the expansion fluid passageway of the device or system. It shall be appreciated that the slider 562 can be moved in both directions, thus enabling control of the amount of expansion fluid expelled from the device.

In some arrangements, moving the slider 560 toward the proximal end of the device can be configured to withdraw air from the passageway that the chamber 570 is connected to, so as to reduce the volume of a bubble or otherwise withdraw a fluid from the fluid passageway of the cannula. In some arrangements, one or more one-way flow valves can be positioned in fluid communication with the chamber to prevent withdrawal of air from the cannula as the slider 560 is moved toward the proximal end of the device however. The chamber can be rechargeable using sterile or filtered ambient or another fluid source as the slider is moved proximally or from a separate source.

The device 560 can be handheld. The distal end 566b can be tapered. When the slider 560 is moved from the proximal end 566a toward the distal end 566b, fluid within the chamber 570 can be forced through the device to put pressure on a film of substance, that may be liquid, gel or some other non-solid composition, that can be suspended across an opening in the distal end 566b. Thereby, a bubble of the substance can be formed out of the hole in the tapered distal end 566b. The film of substance can be formed across a ring that can be positioned inside the distal end of the device. In other arrangements, fluid (e.g., a gas) can be forced from the chamber 570 and into a cannula of any other arrangements disclosed herein toward a distal tip of the cannula by moving the slider 562 toward the distal end 566b of the device.

Some arrangements can optionally include a mechanism for locking a trigger mechanism once the bubble is created, allowing maneuvering of the device in the eye without the need to maintain pressure on the trigger to avoid deflation of the bubble. Additionally, in some arrangements the diaphragm, plunger, or piston within the chamber 570 or any other chamber, such as a cylindrical chamber formed as part of the handle portion or attachable thereto, can be moved by a rotating or twisting action such as by spinning a dial or other threaded components to move the diaphragm, plunger, or piston within the chamber and, thereby, force the expansion fluid out of the chamber and into the cannula. The device of this arrangement, because of the threaded nature of the actuator, can resist inadvertent movement by the back pressure provided by the bubble and also provide greater resolution and control by the user in terms of the amount of air that is evacuated from the chamber.

In some arrangements, both the proximal or the distal end can optionally include an opening that may produce bubbles. Optionally, either the proximal or the distal end, but not both, can include an opening for the production of bubbles. Both the proximal and/or the distal end can include multiple openings that may produce multiple bubbles at the same time.

Any of the arrangements of the devices disclosed herein can include a one-way flow valve that can be configured to allow fluid, such as the expansion fluid or the substance, to flow in the distal direction when the pressure on the proximal side of the valve is greater than on the distal side of the valve, and to prevent back-flow (i.e., flow in the proximal direction) of the fluid or substance.

Some arrangements include a mechanism for locking the actuator mechanism once the bubble is created, or to prevent any backflow of fluid toward the proximal end of the device once the bubble is created. In this state, the device can be maneuvered and manipulated by the surgeon (such as, optionally, in the eye) without the need to maintain pressure on the trigger to avoid deflation of the bubble.

The distal tip of any arrangements disclosed herein can include a one or more flaps adjacent to or covering the distal port of the device. For example, the distal tip can include four flaps, or from two to eight or more flaps, or from three to six flaps. The flaps can be connected to a circumferential edge at or adjacent to the distal tip of the device and/or extend across the cannula exit port.

Figure 21:
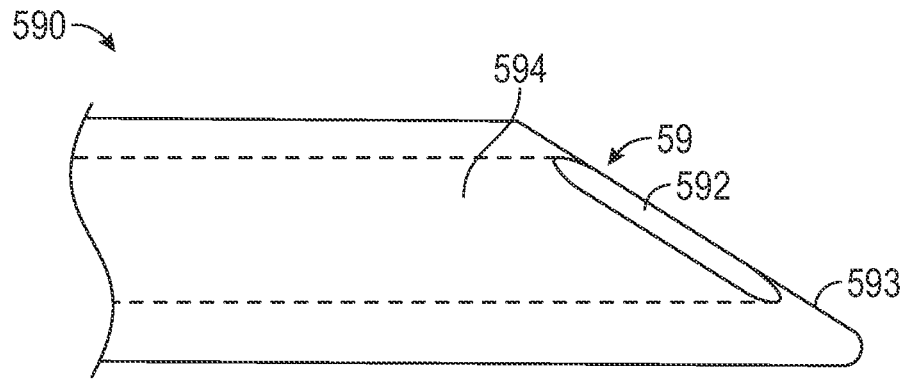
FIG. 21 is a side view of a non-limiting example of a distal tip comprising flaps.
Figure 22:
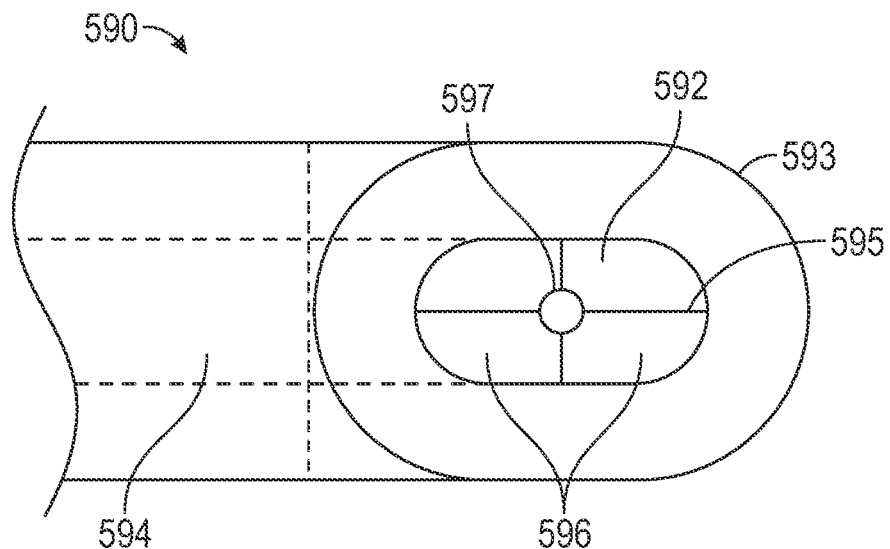
FIG. 22 is a top view of the distal tip shown in FIG. 21.

FIGS. 21 and 22 illustrate another arrangement of a device 590 having an opening 592 extending through a distal surface 593 of a distal end of the device, the opening 592 being in fluid communication with a passageway 594 extending through the device. One or more bendable, resilient flaps 596 (four being shown) selectively cover the opening 592. The flaps 596 can be made from silicon and can form a diaphragm over the opening. The flaps 596 can serve or act as a valve. As shown in FIG. 22, the flaps 596 may include slits 595, rounded or beveled edges, and/or a hole. One or more of the flaps can optionally each comprise a beveled edge.

The silicone diaphragm with one or more slits and/or a central hole may be used with any of the various cannula or applicator tips described herein. The silicone diaphragm may function as a valve to hold substance inside, and/or to control bubble formation. The optional slits or hole at the center of the silicone diaphragm may be any shape. The flaps comprise rubber, silicone, plastic, or an elastic material.

The handle of any arrangements disclosed herein can have a joining portion. The joining portion can include a coupling end. The coupling end can be configured to reversibly or non-reversibly couple with a proximal portion of any cannula arrangement or elongate body arrangement disclosed herein. The proximal portion of the cannula can be configured to reversibly couple with the coupling end of the elongate body or the joining portion of the handle. If the handle has an elongate body, the elongate body can include a joining portion, the joining portion comprising a coupling end configured to interact with a proximal portion of the cannula.

The handle, cannula, or any component thereof or other components of the device, can be made from or can comprise plastic, metal, polyvinyl chloride, glass, acrylic, carbon fibers and/or wood. The distal tip plug or protective tip cover can include plastic, metal, polyvinyl chloride, glass, acrylic, carbon fibers and/or combination thereof or any other suitable materials. The handpiece or cannula, or a component thereof, can be minimally, moderately, or maximally thermally conductive.

The handpiece elongate body, cannula, exit port and/or expansion fluid passageway can have an approximately 20 mm to approximately 50 mm cross-sectional diameter, size, or width, or an approximately 25 mm to approximately 40 mm cross-sectional diameter, size, or width, or a 0.1-0.5 mm, 0.5-1 mm, 1-2 mm, 2-3 mm, 3-4 mm, 4-5 mm, 5-6 mm, 6-7 mm, 7-8 mm, 8-9 mm, 9-10 mm, 10-20 mm, 20-30 mm, 30-40 mm or 40-50 mm cross-sectional diameter, size, or width. The handpiece or handle can have a length of from approximately 4 cm to approximately 12 cm or more, or from approximately 6 cm to approximately 9 cm, or from and to any values within these ranges. The cannula can have a length of from approximately 0.5 cm or less to approximately 10 cm or more, or from approximately 2.5 cm to approximately 5 cm.

Additionally, in any arrangements, infusion and/or aspiration of the bioadhesive substance and/or an activation solution can be manual or foot pedal controlled. Therefore, any arrangements disclosed herein can include a foot pedal. The foot pedal can be configured to expel air or expansion fluid through a tube or channel into the expansion fluid passageway so that it may flow toward and through the distal portion of the device to form a bubble at the distal tip of the device.

A liquid retaining member in the form of an annular wire ring can be used with any of the cannula arrangements disclosed herein. The ring can optionally be secured by means of an angular arm to the tip of the distal end of the device. The liquid retaining member (also referred to herein as a ring) need not be an annular ring but could take any desired shape. The liquid retaining member can be adapted to retain a bubble forming liquid thereacross. When the liquid is applied to the ring, a film of said liquid can be formed thereacross and can be retained in such position until displaced therefrom by air or other pressure.

In some arrangements, an angular arm can be made integral with the ring. The arm can extend along part of the length of the body of the device. The angular arm of the ring can be attached to the device using any suitable components or means. The ring have an attachment, that may be shaped like a button or any other suitable shape, that may extend outside the central core of the device so that it can be easily manipulated with a finger or fingers. The attachment may be used to move the angular arm and attached ring distally and proximally.

Some arrangements include a ring or plurality of rings that provide the means to retain a film of material across the space within the ring, capable of forming a bubble or bubbles when a stream of air or gas is directed against said film to form bubbles. In some arrangements, the ring can be fixed and can be dipped in liquid to create a film across the ring. Some arrangements include a fixed ring that can have liquid actively distributed across the central aperture of the ring. The ring can be a hollow reservoir, that can hold fluid, and that has one or more openings on the inner aspect of the ring that can allow fluid to be infused through the hollow ring then exiting the ring through the openings in the inner aspect of the ring in such a way that creates a film of the liquid across the ring aperture, enabling a bubble to be formed as gas passes through the ring.

For directing a stream of air against the film which can be retained across the ring, an air tube can be mounted axially within the device. The spacing between the ring and the end of the air reduction tube controls the action of the bubble or bubbles which are formed. Also the volume, as well as the velocity of the air passing through the tube, which velocity can be controlled by the bore of the outlet end of said tube, may have an effect on the results obtained. If the end of the tube is too close to the ring, the force of the air stream may merely displace the liquid film without forming the bubble or bubbles. This can cause the rupture of the film. On the other hand, if the spacing between the ring and the end of the tube is too great, the air stream may be dissipated before it reaches the film and bubbles will not be formed. By optimizing the spacing between the air tube and the ring, a bubble or series of bubbles, the size of which can be controlled by the size of the retaining ring, will be formed upon depression of the bulb or a single large bubble may be formed upon each operation of said bulb. Thus, by adjusting the distance between the ring and the tube, as well as by controlling the size of the bore of the tube, a desired effect may be obtained.

Some arrangements of the system and/or device can include a loop. The loop can be retractable—e.g., the loop extends from an end of the device, such as the distal end, and can be retracted in a proximal direction partially or completely within the distal tip of the device to change the size and/or shape of the loop. The loop may be retracted into a handle, cannula or distal tip in accordance with some arrangements. The loop can include a wire. The loop or wire can include a metal such as iron, steel or stainless steel, titanium, nitinol, platinum, or another material such as plastic. The ring can be configured such that the substance fills or forms a film on the wire loop. The adhesive may fill or form a film on the wire loop when the wire loop is retracted and/or expanded, depending on the arrangement. The film may come out from the distal tip and expand or eject into the loop.

The system or device can be configured so that after the bioadhesive substance forms a film on the flexible loop, the wire loop may be applied to a retinal break or tear. Some arrangements include a method of applying a flexible loop with a film of bioadhesive substance to a retinal break or tear. When the wire containing a film is laid on a surface such as a retina or retinal tear, the device and substance can be configured such that the film adheres to the surface (to a degree greater than the adherence of the film to the loop) and can be displaced from the loop.

The loop can be non-flexible and/or non-retractable. The wire or loop can include a thickness of approximately 0.02 mm to approximately 1 mm, or 0.01-0.02 mm, 0.02-0.05 mm, 0.05-0.1 mm, 0.1-0.5 mm, 0.5-1 mm, 1-2 mm, 2-3 mm, 3-4 mm, or 4-5 mm, or a range comprising any combination of said thicknesses. For example, the loop may optionally comprise a flexible suture material such as a polypropylene or collagen suture, and may have one of the aforementioned diameters. Suitable sutures include but are not limited to sutures having a USP designation of 11-0, 10-0, 9-0, 8-0, 7-0, 6-0, 5-0, 4-0, 3-0, 2-0, 0, 1, 2, 3, or 4. The loop can have a diameter of 1-2 mm, 2-4 mm, 4-6 mm, 6-10 mm, 10-20 mm, or 20-30 mm, or a range comprising any combination of said diameters.

Figure 23:
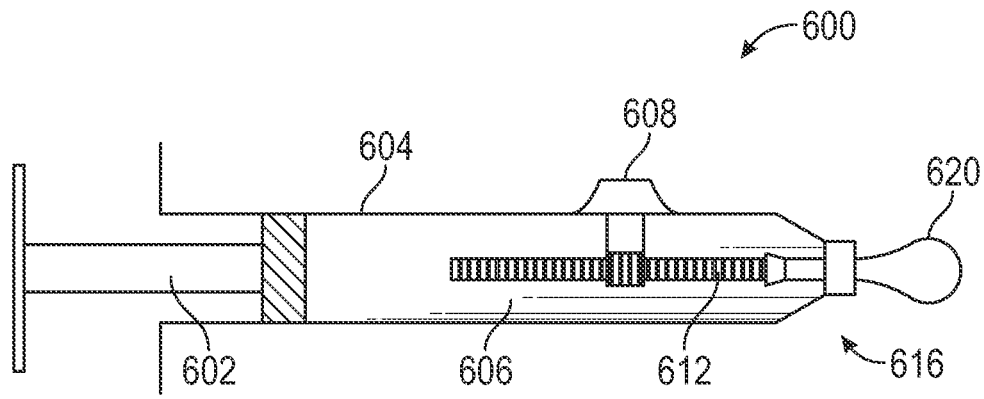
FIG. 23 is a section view of a non-limiting example of a device for providing a substance.

FIG. 23 illustrates an example of a system and/or device that can have a plunger 602, a handle 604, a cavity 606 for holding a bioadhesive substance, an extender knob 608, a rod 612, a locking connector 616, and a flexible loop 620 configured to contain a film of bioadhesive substance. The loop 620 shown in FIG. 23 can optionally be configured to extend further than shown.

The plunger 602 may be used to expel a bioadhesive substance through a hollow cannula and/or into the flexible loop 620 when advanced distally on by a user (for example, pressure from a user's finger or using pneumatic pressure supplied by an external device connected to the handle). For example, the extender knob 608 may be used to extend the rod and, hence, the flexible loop 620 from a retracted position as seen in FIG. 23 to a more extended position or even a more retracted position. The knob 608 and rod 612 can be toothed such that a rotation of the knob in a first direction causes the teeth of the knob to engage the teeth of the rod to advance the rod in the distal direction. A rotation of the knob in a second direction causes the teeth of the knob to engage the teeth of the rod to retract the rod in the proximal direction. For example, the knob 608 can take the form of a roller wheel with teeth on a surface or with a smooth surface that can, when rolled, cause the movement of the rod either distally or proximally. The teeth can optionally be formed in a direction that is parallel with the rotational axis of the knob/roller wheel (not shown).

Alternatively, the knob and rod can be smooth, but in contact such that a rotation of the knob in a first direction causes the advancement of the rod and loop in the distal direction, and rotation of the knob in a second direction causes the retraction or withdrawal of the rod in the proximal direction. Any arrangements of the loop disclosed herein can be used to support a film of substance, such as a bioadhesive, that can be applied to an ocular tissue. This can be used with or without the introduction of an expansion fluid and, hence, with or without the formation of one or more bubbles using the loop. The loop can be, for example, placed in contact with or moved against the target tissue to deposit the substance carried by the loop on the target tissue.

Additionally, in any arrangements, the loop can be temperature controlled (i.e., cooled or heated) to change the adhesive or cohesive properties of film adherence of the substance to the loop, allow disengagement from the film, and/or allow stronger adhesion to the film. For example and without limitation, the wire can be heated or cooled with heating or cooling elements in communication with the loop to any desired temperature to promote release of the substance from the loop.

In some arrangements, bubbles can be formed of the substance retained by the loop. Additionally, in such arrangements, release of the bubble can be achieved by tightening or closing the loop (by withdrawing the loop, advancing a clasp, cinch, or other tightener to tighten the loop, or otherwise) to pinch the loop off of the bubble and detach the bubble from the device. The bubbles can be produced in a controlled fashion, such as being produced slowly, or in a controlled size. The bubbles can be produced one at a time. When a bubble is formed, it can be removed from the device onto a surface such as a retinal or other body tissue. The surface can be of a biological object including but not limited to an eye, a retina, a sclera, a conjunctiva, a hand, skin, or another body part.

Figure 24:
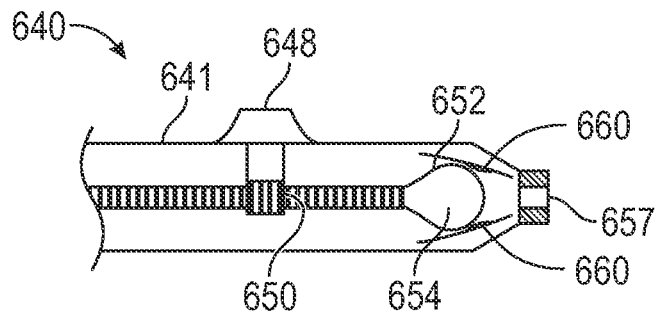
FIG. 24 is a section view of another non-limiting example of a device for providing a substance.

FIG. 24 illustrates an example of a device 640 that can have a handle or housing 641, an extender knob 648, a rod 650, a flexible loop 652 that can be configured to support a film of bioadhesive substance 654, and two or more guide ridges 660 that can be used to guide the loop 652 through an opening 657 in the distal end of the device. The loop can be a retractable loop that can be advanced out of a distal end of the device, as shown in FIG. 25. When the loop 652 is within the housing 641, a substance can be applied to the loop 652 through an injection port, through a distal end of the device, through a passageway within the housing, and/or using any of the other device, components, or methods for advancing a substance through a cannula disclosed herein or known in the industry. A substance can also be added to the loop when the loop is positioned outside of the cannula.

Figure 25A:
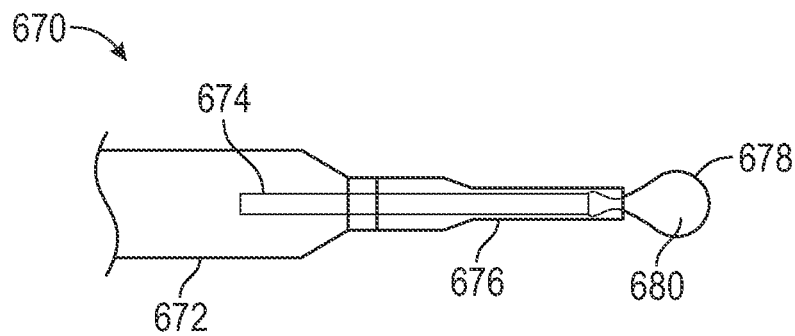
FIG. 25A is a section view of another non-limiting example of a device for providing a substance, showing the loop in an extended position.

FIG. 25A illustrates another example of an arrangement of a device 670 that can include a handle or housing 672, a rod 674, a cannula 676, and a flexible loop 678 that can be configured to support a film of bioadhesive substance 680 across the loop 678. The cannula may be detachable or non-detachable. Additionally, the loop 678 can optionally be detachable from the rod 674 so that the loop can remain in situ after the application of the substance to the target tissue surface. Alternatively, the loop 678 can be withdrawn back into the cannula 676 to cause the substance 680, which can be in the form of a bubble or planar film, to release from the loop 678. Note that the rod 674 can optionally extend from the handle portion, or proximal to the handle portion, so that a user can grasp and manipulate a proximal end 674a of the rod 674 to advance and withdraw the rod 674 distally and proximally, respectively, rotate the rod 674 to manipulate the rod and loop 678, or otherwise. In some arrangements, the rod can be keyed or indexed to the cannula to prevent the relative rotation of the rod relative to the cannula. The loop material in any embodiments described herein can include Nitinol, stainless steel, nylon, or any other desired polymeric or other acceptable material.

Figure 25B:
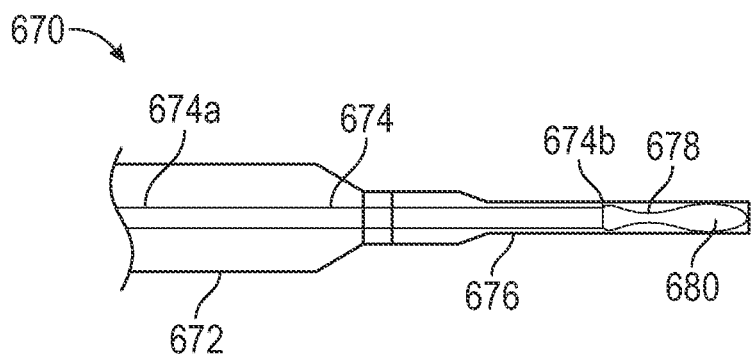
FIG. 25B is a section view of the device shown in FIG. 25A, showing the loop in a withdrawn position within the cannula.

Additionally, in some arrangements, a desired substance can be applied to the loop 678 and the loop can be retracted within the cannula 676 before the device is delivered to the surgeon or the operating room. FIG. 25B illustrates the device 670 with the rod 674 and, hence, flexible loop 678 withdrawn in a proximal direction relative to the handle 672 so that the flexible loop 678 is positioned at least partially (or completely, as shown) within the cannula 676. For example and without limitation, the loop can be preloaded with any of a desired range of substances 680 and the loop 678 can be retracted within the cannula, as shown in FIG. 25B. A plug or seal can be positioned over or into the cannula to prevent the inadvertent discharge or leakage of the substance from the device. In this preloaded state, the device 670 can be ready for use without the surgeon or user having to load the desired substance on the loop 678. The seal can be removed and the rod 674 and loop 678 can be advanced past the distal end of the cannula once the device has been advanced into the desired location, wherein the substance can be deposited from the loop onto the target tissue or surface.

Figure 26:
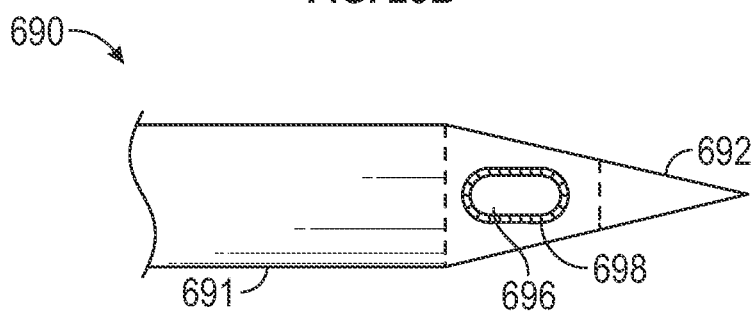
FIG. 26 is a top view of a non-limiting example of a system or device with a trans-scleral tip.

The rod of any arrangements disclosed herein (including but not limited to rod 612, rod 650, and/or rod 674) can be hollow or can be surrounded by an additional sleeve, thereby providing an additional lumen (hereinafter referred to as a supply lumen) through which an additional or a first supply of a substance can be advanced to the loop. For example and without limitation, in some arrangements, the loop 678 (or any loop disclosed herein) can be withdrawn into the cannula and a supply of a substance can be advanced through the supply lumen, past a distal end 674b of the rod 674 (or any rod disclosed herein) and onto the loop 678 while the loop is positioned within the cannula. This can result in the loop being loaded and/or reloaded with the substance within the cannula where the loop and the substance advanced through the supply lumen are confined within the cannula to prevent inadvertent contact of the substance to any unintended surfaces. Some arrangements of the system and/or device can include a trans-scleral tip. For example and without limitation, FIG. 26 illustrates an example of an arrangement of a cannula tip portion 690 for administering a substance, the device having cannula or body portion 691 and a trans-scleral tip 692, among other features. The device 690 can also have a first sharp, pointed distal tip 692 that can be beveled or otherwise. The tip 692 can be configured to facilitate a penetration of the scleral. The device 690 can also have a distal port 696 that can be used for communication of a substance to a desired tissue surface. The port 696 can optionally include a rounded or smooth edge or bevel 698 around the distal port 696. The port 696 may include a silicone diaphragm having any of the components and/or features of the diaphragm(s) disclosed above, or a diaphragm made out of another material. The end surface or tip portion 692 can be solid and can be beveled on both sides or on just one side, can have a conical shape, or otherwise. In some arrangements, the distal tip 692 can be sharp and can be used for cutting a tissue of the eye. The cannula tip 690 and its features can be used with any of the arrangements of devices disclosed herein.

Figure 27:
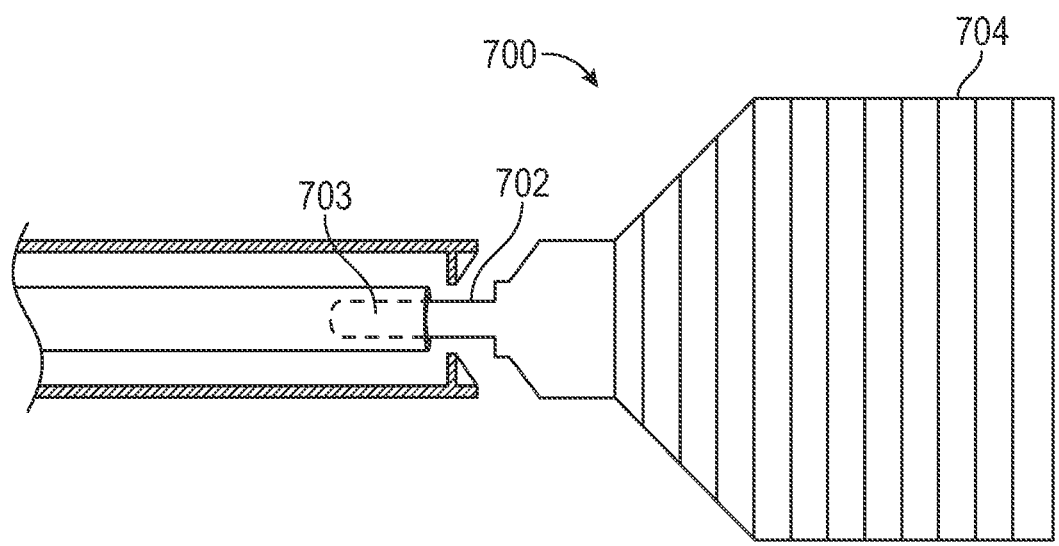
FIG. 27 is a section view of a distal portion of a non-limiting example of device for providing a substance.
Figure 28:
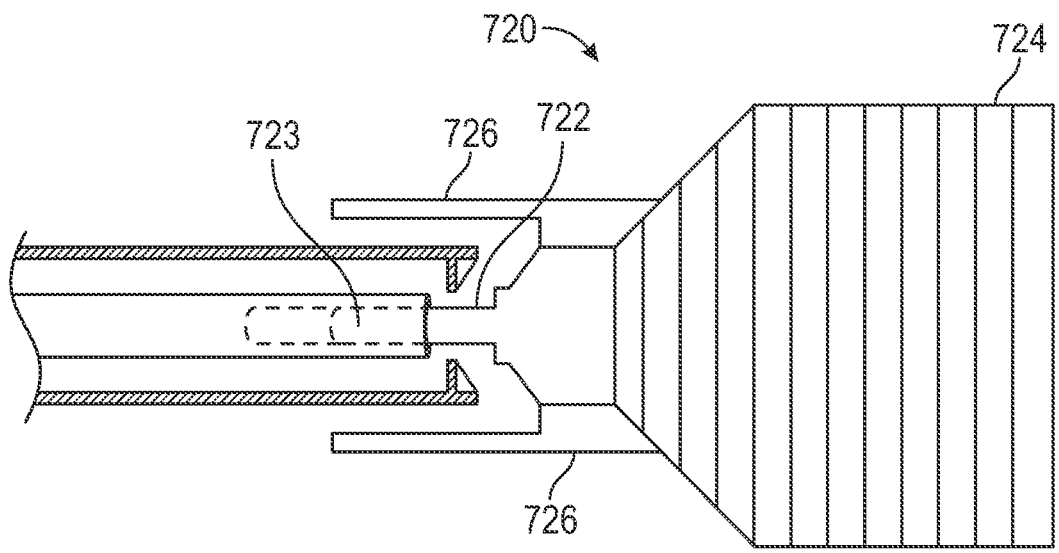
FIG. 28 is a section view of a distal portion of another non-limiting example of device for providing a substance.

Some arrangements of the system and/or device can include a tip plug. Non-limiting examples of tip plugs are shown in FIGS. 27 and 28. The tip plugs 700, 720 shown in FIGS. 27 and 28 can include a neck portion 702, 722, respectively. The neck portions 702, 722 can be shaped to fit the dimensions of the tip of the cannula. For example, the neck portions 702, 722 can be shaped to fit the dimensions of any substance retention rim, lip, or ring on or at the end or tip of the cannula. The neck portions 702, 722 of the tip plugs 700, 720 can include a beveled portion configured to be flush with a beveled portion of the distal tip. The tip plug can include a beveled portion configured to be flush with a beveled portion of the distal tip when the elongated member of the tip plug is placed within the distal tip.

The tip plugs 700, 720 can include an elongated portion 703, 723, respectively. The elongated portion 703, 723 of each plug can be connected to the neck 702, 722 of each plug. The elongated portion 703, 723 can include a proximal end and a distal end. The proximal end of the elongated portion 703, 723 can be configured to fit within a distal tip of any arrangements of cannulas or devices disclosed herein. For example, the elongated portion 703, 723 can fit inside a central tube of the system or device. The tip plug can include an elongated member comprising a proximal end and a distal end, wherein the proximal end of the elongated member can be configured to fit tightly (e.g., to prevent expansion media escape) within the distal tip. The elongated portion 703, 723 can optionally be 1-5, 5-10, 10-20, 20-30, 30-40, or 40-50 mm in length. For example, as shown in FIG. 28, the elongated portion can be formed in a range of lengths. The elongated member 1305, 1405 can include an elongated plug tip that fits inside a central tube of the device or system, or a distal tip of the system or device.

The tip plugs 700, 720 can include a tip plug handle or pull tab 704, 724. Tip plug handle 704, 724 can be connected to the distal end of the elongated member 703, 723 or to the neck 702, 722. For example, the tip plugs 700, 720 can include a fingertip tab 704, 724 that can be wider and more easily grasped compared to the elongated member 703, 723. The fingertip tab 704, 724 may include a textured surface on one or more sides, such as ridges, dots, and/or hashes, or some other non-smooth surface. The tip plug can include a tab connected to the distal end of the elongated member of the tip plug.

With reference to FIG. 28, the tip plug can include one or more supportive struts 726. The supportive struts 726 can be configured prevent the tip plug 720 from breaking off when the elongated member 723 is inserted into the distal tip. The supportive struts 726 are configured to fit around the distal tip and can be have a continuous, annular shape, or two or more discrete struts. Some arrangements include a single circumferential supportive strut. The circumferential supportive strut can be an outer tube that fits over or around a portion of the tip of the cannula. The tip plug can include an outer tube that fits over or around a portion of the tip of the cannula. The elongated member 723 can be configured to fit inside the cannula. The central core can be longer, shorter, or the same length as the outer tube or supportive struts 726. Some arrangements include a continuous, annular strut. Some arrangements include non-continuous struts.

Figure 29:
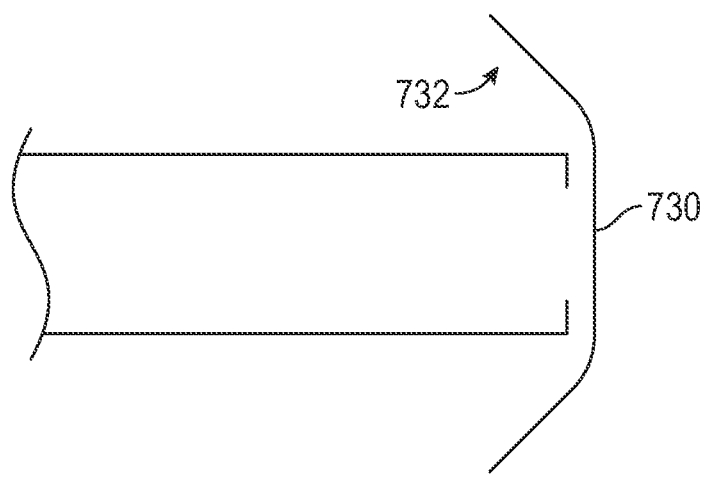
FIG. 29 is a side view of a distal portion of another non-limiting example of a tip cover.

As mentioned, some arrangements of the system and/or device include a tip cover such as a protective tip cover. A non-limiting example of another type of tip cover 730 that can be configured for use with any cannulas disclosed herein is shown in FIG. 29. The tip cover 730 can include a first or proximal side and a second or distal side. The first side can optionally include an adhesive configured to engage the cannula. The protective tip cover can further include a nonadhesive tab, such as for example and without limitation, the nonadhesive tab 732 shown in FIG. 29. The tab 732 can be configured to aid in removal of the tip cover 730 from the distal tip of a cannula. The tip cover can be removable when the system or device, or the distal tip of the system or device is ready to use. The cannula can be configured to be filled or contacted with a bioadhesive substance through a hub of the cannula or through tip of the cannula before securing any of the tip covers disclosed herein.

The tip plug or tip covers disclosed herein can be configured to protect the distal tip, maintain the sterility of the distal tip, or prevent the distal tip from getting dirty or cutting another item such as a fingertip or other object, and/or preventing a leakage of the substance contained within the cannula or device. For example, the tip plug or tip cover can be attached to the system or device during transportation of the device or system. The system or device can be preloaded with a substance such as a bioadhesive substance. The preloaded system or device can include the tip plug or tip cover. The tip plug or tip cover retains the bioadhesive substance within the preloaded system or device.

Any devices or arrangements disclosed herein can include one or more features configured to disengage the substance from the device. Such features can include, for example and without limitation, cutting features or components such as razor blades or sharp blades, thin metal or polymer blades, scrapers, spatulas or other similar devices configured to slide the substance off of the device. Additionally, in some arrangements, the bubble can be optionally clipped or pinched off the device.

Figure 30:
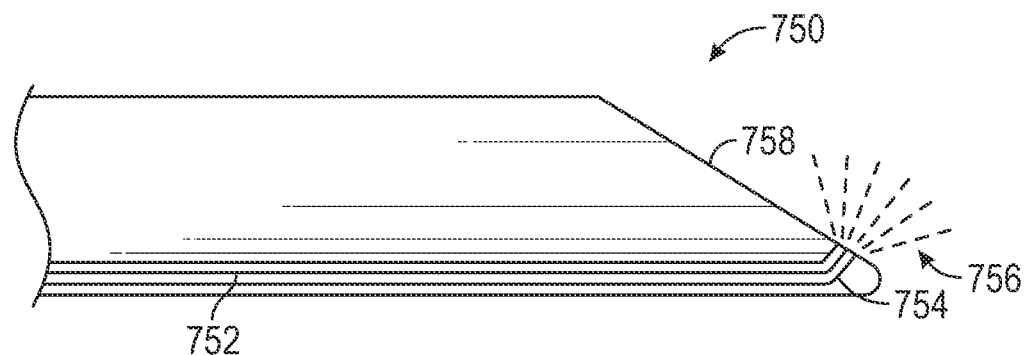
FIG. 30 is a side view of a non-limiting example of a cannula with one or more fibers or wires for light or cautery.

Any arrangements of the systems and/or devices disclosed herein can include an internal cautery component. Some arrangements can be configured to have a cannula with a fiber or wire that can be used for light or cautery. FIG. 30 illustrates an example of an arrangement of a cannula 750 having a fiber or wire for light or cautery. The cannula 750 can include a light fiber 752 within a tube along a length of the cannula. The light fiber 752 can include an angled end portion 754 in the example, but, in other arrangements, the end of the light fiber 752 can be straight. The end portion 754 of the light fiber 752 can be beveled at an angle that matches the angle of the bevel of the distal tip.

The cannula 750 can include a light 756 emitted by the end 758 of the cannula 758 or light fiber 752. Any arrangements of the devices disclosed herein can be configured to include one or more light fibers 752 or any of the other features of cannula 750, and the cannula 750 can be configured to include any of the features of any of the other cannulas, devices, or other components or systems disclosed herein.

Additionally, an extra tube can be included that can be configured for passage of an additional material (such as a liquid) that can be expressed from the distal tip as a spray or as drops. For example, the additional material may be used to activate the bioadhesive substance. The device or system, or a component thereof such as the handle, cannula, distal tip, light, or light fiber can be configured to emit a light at a wavelength that activates, thickens, or hardens the bioadhesive substance.

The system and/or device and/or components thereof may be activated in a manner that increases the temperature at the distal tip (using, for example, the internal cautery component). This can be advantageous according to some arrangements in aiding disengagement of the bioadhesive bubble from the distal tip in instances where the bioadhesive substance can be a temperature-responsive material that becomes more fluid and/or less cohesive at higher temperatures.

Some arrangements include a cryotherapy component such as a cryotherapy handpiece. The system or device can be activated in a manner that decreases the temperature at the distal tip (using, for example, a cryotherapy component). This can be advantageous according to some arrangements in aiding disengagement of the bubble or other form of the substance from the distal tip in instances where the bioadhesive substance can be a temperature-responsive material that becomes more fluid, friable, or releasable at lower temperatures.

Figure 31:
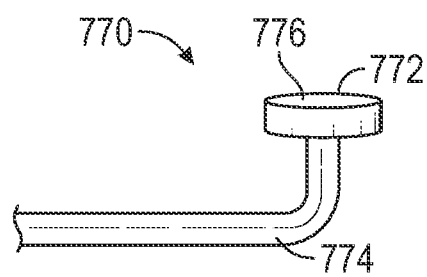
FIG. 31 is a first side view of a distal portion of a non-limiting example of a cannula.
Figure 32:
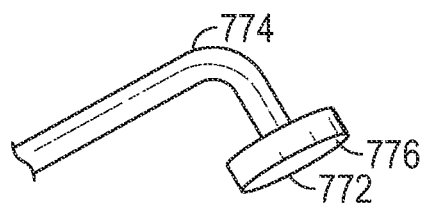
FIG. 32 is a second side view of the cannula shown in FIG. 31.

Some arrangements of the systems and/or devices disclosed herein can have a special end portion that can have an increased application area, for example for applying heat or cold to a tissue surface or to a bioadhesive. Some arrangements can have a distal end portion having a solid circular shape, such as a button shape. FIG. 31 is a first perspective view and FIG. 32 is a second perspective view of an example of an end component 770 having a button tip arrangement. The button tip end component 770 can have an enlarged end surface or portion 772 and an elongated arm portion 774 coupled with the end portion 772 that can be straight or can be bent, as shown. The end portion 772 can be solid or can have one or more passageways therethrough, for expansion fluid, substance, or otherwise.

The button base can include a solid floor with an opening for the distal tip which ends flush with the button floor. The surface of the button can be open so as to form a reservoir configured to hold a substance such as a bioadhesive substance. The surface of the button can be solid with a central opening. The distal surface 776 of the end portion 772 can be generally planar, curved, or otherwise.

The button tip cannula can be configured to be heated or cooled. The button-tip cannula can be used to liquefy a viscous, solidified, or partially solidified bioadhesive by holding the cooled or heated button-tip cannula over the bioadhesive substance until it can be converted into a liquid state enabling it to be aspirated with the same or a different device. The button tip design provides an area such as a broad area of either heat or cold over an area such as a broad area of bioadhesive providing more rapid liquification and removal of the bioadhesive than might otherwise be achieved with a cooling or heating tip with a smaller surface area.

Examples of substances that can be used with any of the devices, systems, and methods disclosed herein include, without limitation, adhesives, bioadhesives, gels, hydrogels, thick liquids or semi-liquid treatment substances, double layer hydrogels, nonsolids and the like. As used herein, any use of the term substance is intended to include any of the types and examples of substances disclosed anywhere in this disclosure.

Examples of substances that can be used with any of the devices, systems, and methods disclosed herein and which are contemplated as being included in each use of the term "substance" herein include, without limitation, any of the following: adhesives, bioadhesives, gels, hydrogels, thick liquids or semi-liquid treatment substances, double layer hydrogels, nonsolids, a polyethylene glycol solutions, a trilysine amine solutions, polymeric hydrogels, thermoresponsive gels, polyvinyl acetate, glue, aliphatic, cyanoacrylate, epoxy, polyurethane glue, and contact cement, glycoproteins, elastic, proteins, carbohydrates, mucopolysaccharides, hydrogels, double layer hydrogels, polymeric hydrogels, polyethylene glycol hydrogel and other hydrogels, biomimetic substances, ReSure™ sealant, a polyethylene glycol hydrogel, fibrin glue, a polyethylene glycol solution, a trilysine amine solution, glycoproteins, a polyethylene glycol solution, trilysine amine solution, elastic proteins, carbohydrates, mucopolysaccharides, temperature activated bioadhesives, UV or light activated bioadhesives, and vaccines, etc.

Any arrangements disclosed herein can also be configured to use one or more substances that polymerize as the temperature of the substance reaches a threshold value or range of values, such as for example and without limitation, normal body temperature, or to any values from approximately 80° F. to approximately 100° F. or greater, or from approximately 90° F. to approximately 100° F. or greater, or from approximately 95° F. to approximately 100° F. or greater, or to and from any values within these ranges. Additionally, any arrangements can be used to apply a cold cured substance to a tissue surface—i.e., substances that polymerize as the temperature of the substance drops to a threshold value or range of values, such as for example and without limitation, 10° F. below body temperature, or to any values from approximately 70° F. or less to approximately 90° F., or from approximately 80° F. to approximately 90° F., or to and from any values within these ranges.

Any arrangements disclosed herein can also be configured to use one or more substances that polymerize with activation by any number of various wavelengths of light, or are activated by light. Activation light may be provided by special applicator within or separate from the substance delivery device. Suitable substances that can be used also include substances that are typically used in or are approved for use in subretinal space, a vitreous cavity, or an ocular surface including on or under conjunctiva, and substances that may be used for closing gaps in tissue.

The substance can be configured so as to be safe and non-toxic to the eye, injectable, and bindable to a retinal tissue when hydrated and/or cured. The substance can also include substances with characteristics suitable for bubble/foam formation including but not limited to adhesive and non-adhesive substances for use both inside and outside the eye or any other human or animal tissue.

After creation of the bioadhesive bubble and dissociation of the bioadhesive bubble from the distal tip, the bioadhesive substance can be activated with application of a solution that may be delivered by the bioadhesive delivery device which may be constructed so that it has separate tubes for delivery of the bioadhesive substance and the activation solution.

The devices disclosed herein can be used for vaccine delivery, and the substance delivered by the device can include a vaccine. The vaccine delivery may comprise nasal delivery using a bubble, which may be a more efficient delivery than a spray delivery. The device may deliver the vaccine in a greater concentration over a greater surface area than existing vaccine delivery methods, potentially increasing the amount of vaccine absorbed by a subject to which the vaccine is applied.

Other substances that can be delivered with any of the arrangements disclosed herein and which are contemplated as part of the term substance, as used herein, include: substances that polymerize as they approach body temperature, substances that polymerize with activation by any number of various wavelengths of light, substances that are activated by light, and substances that are intended for use in a subretinal space, a vitreous cavity, or an ocular surface including on or under conjunctiva.

Any combination of the devices and/or components described herein can be provided together in a kit. Some arrangements of the kit further comprise a second system or device, and wherein the systems or devices are each disposable after a single or limited number of uses. Some arrangements of the kit further comprise an adhesive biomaterial. Some arrangements of the kit further comprise a substance dispenser. Some arrangements of the kit further comprise a tip plug or protective cover. The system, device, or kit described can be sterile or pre-sterilized. The kit can include a pre-sterilized substance dispenser described herein. The device can be used for non-medical substance delivery, including but not limited to adhesives, lubricants, insulators, sealants (for example, gas fittings, or pipe/plumbing fittings). This may be preferable to Teflon tape in hard to reach areas.

Arrangements of the system and/or device can comprise a substance dispenser. The substance dispenser can include a base with a well or a series of wells or open ended reservoirs. The dispenser can include a container made of plastic, metal or glass. The well or the series of wells can each comprise a substance such as the bioadhesive substance. Alternatively, the substance dispenser can include a series of distal tips preloaded with a substance configured to be selectively attached to a handpiece or cannula of any arrangements disclosed herein. The cannula or cannulas can be configured for a one-time or single use, or may be reusable. For example, the cannula can optionally be configured to be reusable within a period of time such as 1-60 min, 1-24 hours, and/or 1-3 days.

Figure 33:
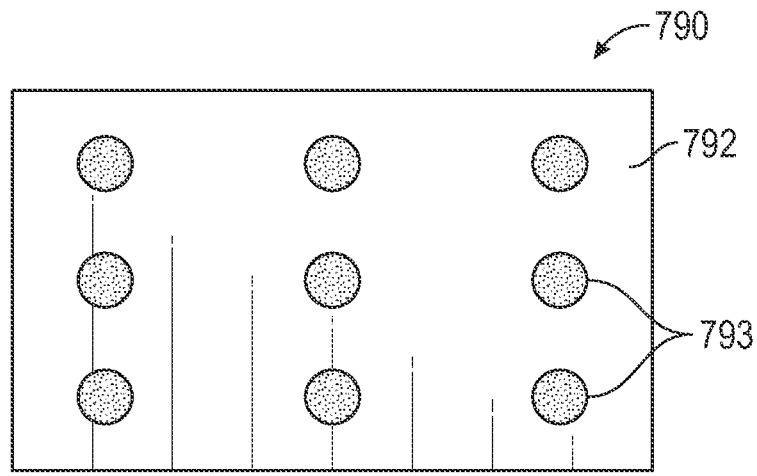
FIG. 33 is a top view of a non-limiting example of an arrangement of a substance dispenser.
Figure 34:
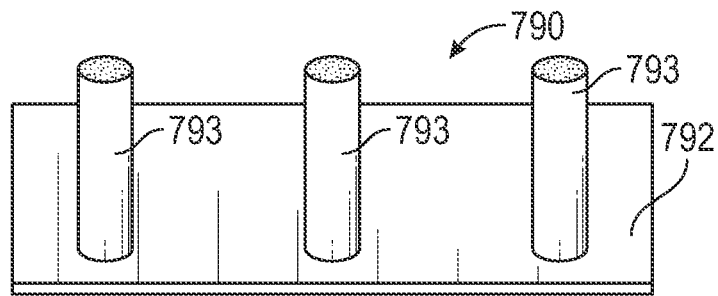
FIG. 34 is a front view of the arrangement of the substance dispenser shown in FIG. 33.

An example of a substance dispenser 790 is shown in FIGS. 33 and 34. The example can include a base 792 having a series of wells or reservoirs 793 each comprising or preloaded with a bioadhesive substance or comprising a different cannula or tip portion. Each well can optionally contain a single dose of substance or multiple doses of a substance. The diameter of each well can be such that the cannula fits tightly within the well so that the substance may be efficiently and cleanly drawn into the cannula. In some arrangements, the substance dispenser 790 can have a plurality of cannulas that can be removed from the base 792 and attached to the device that is being used.

Some arrangements of the system and/or device include a method of using a substance dispenser. The method can include placing a cannula in a well containing a dose of substance, and/or optionally applying a small amount of gentle aspiration to the cannula to engage the substance within the tip of the cannula, and withdrawing the cannula from the dispenser. The wells of the substance dispenser can each include a tear-off cap or cover. The substance dispenser can be sterilized or pre-sterilized, and/or can include a sterilized liquid or substance such as a sterilized bioadhesive substance.

Figure 35:
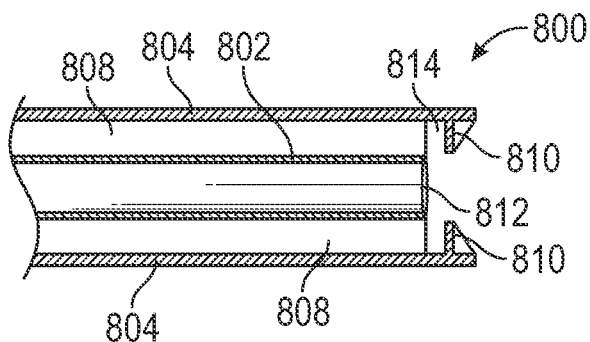
FIG. 35 is a section view of a distal portion of another non-limiting example of a cannula.

FIG. 35 is a section view of a distal tip 800 having a first and a second substance supply channel through at least a portion of the distal tip. An attachment or coupling 801 can be formed between an inner tube or channel 802 and an outer tube or channel 804. The attachment may be along the entire length of the channels or may have intermittent attachments.

Figure 36:
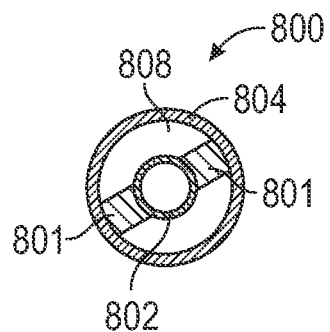
FIG. 36 is a section view of another non-limiting example of a cannula.

The distal tip 800 can have a space 808 between the inner tube 802 and the outer tube 804. The distal tip 800 can also have a substance retention rim 810 extending radially inwardly adjacent to the distal end port or opening 812 of the distal tip 800. The space provided inside the retention rim 810 can be filled with a substance and can aid in bubble formation. The example in FIG. 36 shows the attachments 30 between the inner tube 802 and the outer tube 804. In some arrangements, connectors can be used to stabilize the inner tube 802 within the outer tube 804.

Figure 37:
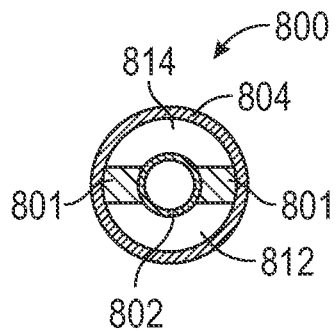
FIG. 37 is a section view of another non-limiting example of a cannula.
Figure 38:
FIG. 38 is a side view of a non-limiting example of a distal tip.
Figure 39:
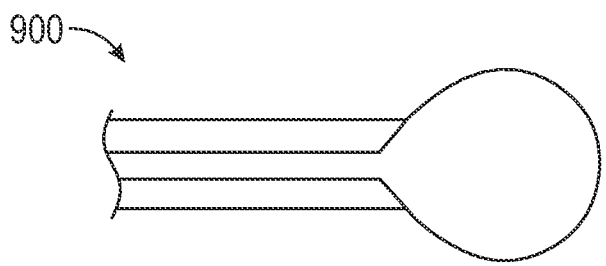
FIG. 39 is a side view of a non-limiting example of a distal tip with a bubble.

Another arrangement of the device is shown in FIG. 37. A first reservoir 812 (or a first substance supply channel) and a second reservoir 814 (or a second substance supply channel) can be formed along a length of the distal tip 800. The first and second reservoirs can be divided and separate along the length thereof. In the example shown in FIG. 37, the first reservoir can be configured to hold a first substance, and the second reservoir can be configured to remain empty and act as a receptacle for (or receive) a second substance or an activation solution as the second substance or activation solution advances out of the end of the first reservoir. A distal tip plug may be used to prevent efflux of substance out of the distal tip. The first and second reservoirs can each be configured to hold a separate bioadhesive substance or an activator substance, and/or the reservoirs can be configured to expel both bioadhesive substances together to allow the bioadhesive substances to mix and optionally react with each other prior to forming a film and bubble.

Any devices disclosed herein can be used to apply a bioadhesive bubble to a retina, comprising a proximal end comprising a handle, a distal end, an internal fluid passageway from the proximal end to the distal end, and a cannula connected to the distal end, comprising a distal tip, and configured to generate a bioadhesive bubble from a bioadhesive when a gas flows through the internal fluid passageway, maintain the bubble on the distal tip when the gas stops flowing through the internal fluid passageway, and release the bubble when the bubble can be brushed against a retina or when the gas flows again through the internal fluid passageway.

Some arrangements relate to a use of a system, device or kit for generating and/or applying the bioadhesive bubble to an eye or retina such as for repair of the eye or retina. The use can include generating a bioadhesive bubble using a system, device or kit described herein, and/or applying the bioadhesive bubble from the tip of the cannula to the eye or retina using a system, device or kit described herein.

Some arrangements relate to a method of repairing a retinal tear. Some arrangements of the method or use include generating, with a system, device or kit, a bioadhesive bubble comprising an approximately spherical film of bioadhesive substance enclosing an expansion fluid. Some arrangements of the method or use include applying the bioadhesive bubble to the eye or retina from the system, device or kit. Some arrangements relate to a method of repairing a retinal tear or hole, comprising: generating, with a system, device or kit, a bioadhesive bubble comprising an approximately spherical film of bioadhesive substance enclosing an expansion fluid, and applying the bioadhesive bubble to the eye or retina from the system, device or kit. Some arrangements include operation of a button on the handpiece of the device or system, or operation of a foot pedal to, for example, open a valve to allow expansion fluid to flow through the expansion fluid passageway of the handpiece and/or through the fluid passageway of the cannula.

Some of the devices disclosed herein convert a cohesive liquid into a bubble with much larger surface area and control and accuracy of placement, than the original cohesive liquid without a bubble, significantly improving its capabilities when used for any of the following functions: closing gaps in tissue, reducing incidence of PVR by blocking liberation of RPE cells into the vitreous cavity.

The devices and methods disclosed herein can be used to close a variety of discontinuous and continuous structures including but not limited to retina tears and holes, macular holes, macular pits, break in posterior lens capsule, scleral laceration, corneal laceration, corneal abrasions, conjunctival laceration, retinal pigment epithelial tears, non-ocular medical uses include but are not limited to skin lacerations, mucosal laceration—regardless of location, and delivery of substance with no other functions, without limitation.

The substance delivered by any device disclosed herein can be used to deliver substance transvitreally. For transvitreal use, delivery through the device may employ a cutting action to amputate the cohesive/sticky substance once the substance has been advanced to the target location. Excess can be removable with a vitrectomy cutter and/or aspiration. Transvitreal delivery may be utilized in an air filled eye to avoid adhesive substance floating to non-targeted ocular structures such as lens/IOL/pars plicata/angle, corneal endothelium which could result in obscuration of view through lens/IOL or impairment of inflow/outflow of aqueous humor.

Any devices disclosed herein can also be delivered by trans-scleral delivery, and may include delivery of substance to the retinal break through the subretinal space. After the substance is applied to the retina after being delivered via a tapered end of the device, or needle, the substance may be detached as the needle is withdrawn from the sclera. The substance may act as a buffer to prevent retinal incarceration into sclera defect left by the cannula, needle, or device utilized to cross the scleral and choroidal tissue.

Any arrangements of the delivery devices disclosed herein can have a single, double, or triple bore. The double bore device can include one bore for delivery of a substance and a second bore for reflux of intraocular fluid to outside the eye as TOP increases. One of the bores can contain a light fiber that may be used for illumination. One of the bores contains a fiber that can deliver a laser light. One of the bores contains a fiber that delivers heat or some other source of energy used for curing the injected substance. The triple bore device can include one bore for delivery of a substance, one bore for passage of gas used to create bubble or film of adhesive substance, and a third bore for reflux of intraocular fluid to outside the eye as TOP increases.

Figure 40:
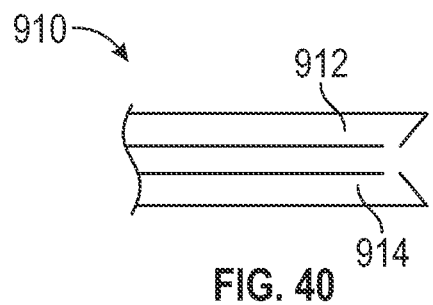
FIG. 40 is a side view of a non-limiting example of a distal tip.
Figure 41:
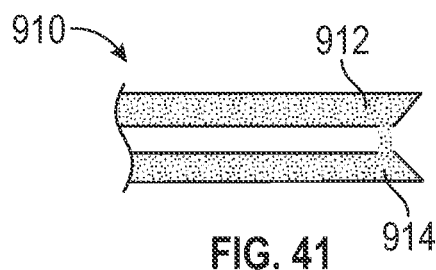
FIG. 41 is a side view of a non-limiting example of a distal tip with a substance within the distal tip.
Figure 42:
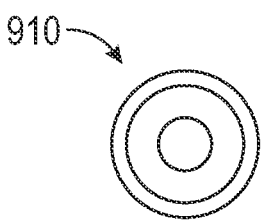
FIG. 42 is an end view of a non-limiting example of a system or device as described herein.

FIGS. 38-42 show schematic illustrations of examples of the distal end or tip of various arrangements 900, 910 of devices. In any arrangements, a single or dual compartment syringe can attach to a distal tip with dual compartments matching up when connected. With reference to FIG. 40 and FIG. 41 dual, isolated columns of air can optionally compress contents within the optional two distal tip compartments 912, 914. Some arrangements include a handle such as a syringe-like handle.

As shown in FIGS. 38-42, there may be an internal aspect of the distal tip, which may be flared to provide support and stability to a bubble at the tip. The tip may comprise material such as a hollow wall on the outside, and air or gas inside or in the internal aspect. The tip can have one or more openings (such as passageways) that can communicate between hollow walls of the cannula containing material, and a central core of the cannula through which passes a gas such as air, nitrogen, oxygen, or another gas. A film of substance can be created across an opening in the distal end or distal tip. Hollow walls of the cannula may be of various volumes and relative volumes of hollow walls and the center core may vary. Some arrangements include a dual plunger for the central core, and/or a hollow walled outer cannula. The dual plunger may work and/or advance in unison or independently of the other components of the cannula or device. Components may be of various lengths, widths, and volumes.

In any arrangements disclosed herein, the device and/or method of use can be configured to have one or more of the following features, characteristics, capabilities, processes, or details: A hand held, syringe-shaped device that creates bubbles in controlled fashion, one bubble at a time; The ability to create bubbles from liquids of various compositions and viscosities; The ability to create bubbles from gels of various compositions and viscosities; The ability to maintain reservoir of substance, from which bubbles are created, at temperature within specific range depending on the substance used; A temperature-controllable chamber within device that can be calibrated specifically for the substance being used for task at hand so temp control can be on-off, though a temperature control mechanism could optionally be added to the device; A source of power comprising one or more batteries, wherein the batteries can optionally be incorporated into the hand-held device; A source of power comprising an electrical cord that connects to a vitrectomy machine power supply or to an external power supply; One or more color-coded devices with each color correlating with a specific substance composition, wherein the different substance compositions can optionally have a specific optimal temperature or temperature range to optimize bubble creation; A device configured to allow control and variation of bubble wall thickness based on, for example and without limitation, a temperature of the substance during bubble creation using one or more of heaters and/or coolers; A device configured to allow control and variation of bubble wall thickness based on the viscosity of the substance during bubble creation; A device configured to vary bubble wall thickness with various dimensions of certain device apertures and the amount of air or gas passed through the substance composition during the bubble making process, including without limitation a kit or system that has a plurality of different of devices, each with a different distal tip aperture that generates bubbles with consistent size/diameter and wall thickness that is different from other devices of the kit; and another arrangement that has a device with an adjustable aperture and the ability to control a volume of the air injected to form the bubble, providing ability to customize size of bubble and thickness of bubble wall depending on clinical setting, for example in a retinal detachment application with multiple retinal tears of various sizes where it may be desirable to use bubbles or a variety of sizes but each having approximately the same bubble wall thickness.

In any arrangements disclosed herein, the device can be configured to also have one or more of the following features, characteristics, capabilities, or details: Using one device to close retinal tears and then at end of case to close external scleral opening through which cannulas were inserted (i.e. sclerotomies) in which case surgeon may wish to have access to greater bubble wall thickness due to greater tensile forces associated with scleral wound compared to retinal break; Variations of the device to create bubbles of various sizes with various diameters ranging from, for example 0.5 mm-15 mm, other ranges of bubble diameters include, for example, 0.1 mm-0.5 mm, 0.5 mm-1 mm, 1 mm-2 mm, 2 mm-5 mm, 5 mm-10 mm, 10 mm-25 mm, 25 mm-50 mm, and 50 mm-100 mm, or any number therebetween; The ability to release the bubble and create additional bubbles that can also be released, which can be done in fashion that avoids plugging of cannula/device tip; A mechanism to release the bubble from cannula/device tip, which mechanism to release the bubble can include one or more of heating of tip to melt or heat the substance, chilling the tip to fracture the substance, and a device having a cutting or wiping mechanism at the tip; A device including a light fiber used to transmit light used for the curing of the substance used in the balloon, which light fiber can be fixed or it can be movable so as to be advanced out of the tip of the device, which light fiber may be advanced to the interior of the bubble to bring it into closer proximity to the portion of the bubble that is in contact with the retina, sclera, or other targeted human tissue, and/or which light fiber may be housed in a different bore of the cannula and be used to cure the substance from outside the balloon; and a device that may include a cannula and associated distal tip, separate from the bubble generating portion of device, that permits the dripping or spraying of a liquid or gel or other substance on the surface of retina prior to application of the bubble, wherein a purpose of this other substance may be to deposit a substance of specific composition that reacts with the bubble substance, resulting in a change in the consistency of both substances, for example from liquid to solid.

Figure 43:
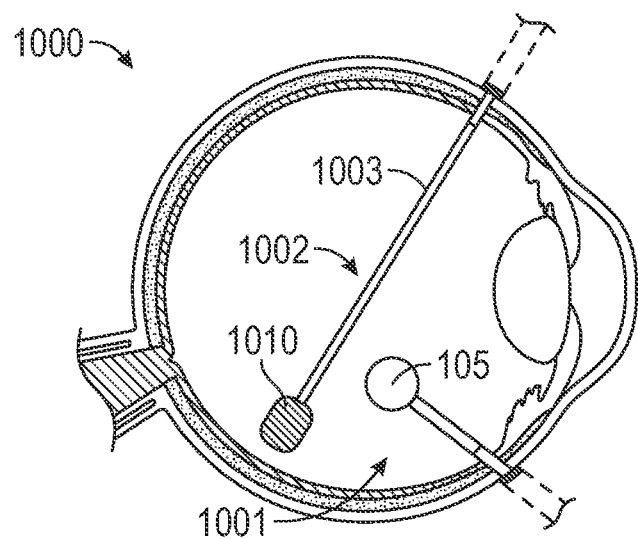
FIG. 43 illustrates a non-limiting example of a system having an applicator device and a substance providing device.

Any of the arrangements of the devices and systems disclosed herein can be used to apply an adhesive to a biological or non-biological surface or object, which object can include medical scaffolding, patches, covers, grafts, or other objects or implements used in medical and non-medical applications. For example and without limitation, FIG. 43 illustrates a non-limiting example of a system 1000 having a substance supply device 1001 and an applicator device 1002. The substance supply device 1001 can include any of the devices, arrangements, and/or components disclosed elsewhere herein in any combination to provide a substance to a surface or an object, including without limitation devices 100, 200, 250, 350, etc. The substance supply device 1001 can be advanced through a first introducer cannula or sheath into a desired space or location (such as, without limitation, an eye cavity that has been filled with air) and the applicator device 1002 can be advanced into the eye cavity through a second introducer cannula or sheath. The substance supply device 1001 can be used to apply a substance, which can include a bioadhesive, to a desired surface of the applicator device 1002.

Figure 44:
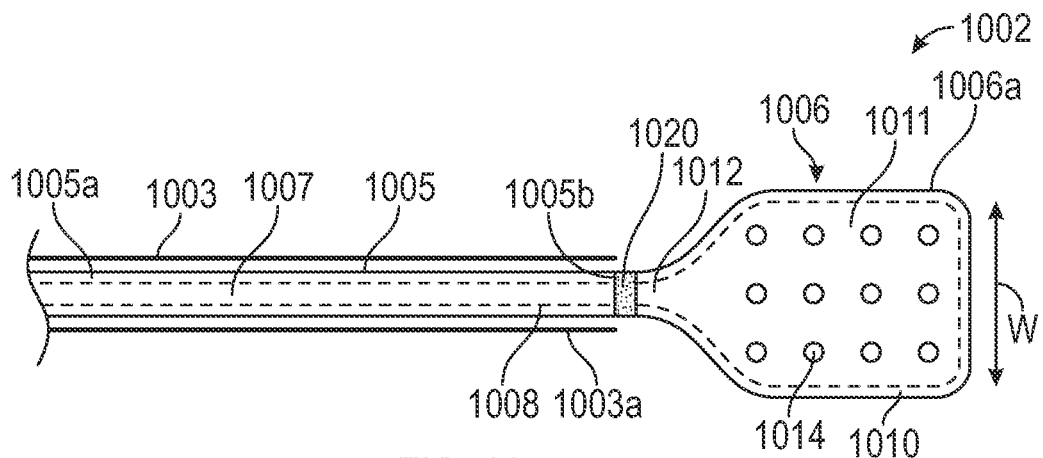
FIG. 44 is a top view of a non-limiting example of an applicator device, showing an applicator tip of the device in an open state.
Figure 45:
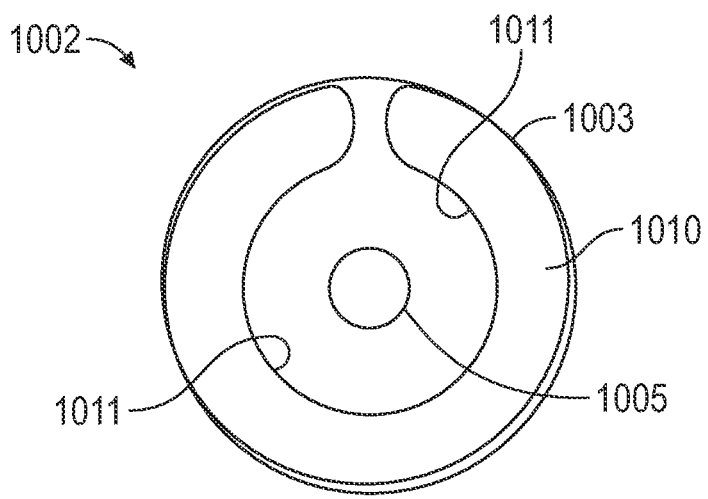
FIG. 45 is an end view of the applicator device shown in FIG. 44, showing the applicator tip of the device in a closed state.

FIGS. 44 and 45 depict a top view and a side view, respectively, of an example of the applicator device 1002 that can be used with any of the devices disclosed herein for supplying a substance to a surface or an object. As will be described, in any arrangements, the applicator device can be used to receive a substance on an applicator portion thereof for application of the substance to a tissue surface or an object, to support an object therewith (such as a patch or otherwise) and deliver the object to a desired location, or otherwise. For example and without limitation, the applicator device can be configured to support a patch, tissue cover, tissue graft, tissue scaffolding, or otherwise (collectively referred to herein as a patch) thereby, wherein the surgeon or user can use the applicator device 1002 to position and apply the patch to the desired target location. The patch can optionally be pre-loaded with an adhesive (which can be a bioadhesive) or other substance, or can be loaded with the adhesive in the surgical location or space using the substance supply device 1001. Thereafter, once the patch has been loaded with the desired amount of adhesive, the patch can be applied to the desired object or tissue surface. Additionally, without limitation, the applicator device 1002 can be used to hold the patch in the desired application location to allow for the adhesive to sufficiently set or cure and, hence, bond to the target tissue.

With reference to FIGS. 43 and 44, the applicator device 1002 can include a cannula or outer sleeve 1003 (also referred to herein as an elongate body or outer sheath), an inner sleeve or rod 1005 that can optionally have a solid cross-section or a lumen or passageway 1007 extending therethrough, and an applicator tip 1006 coupled with the inner rod 1005. The outer sleeve 1003 can optionally be configured to provide additional rigidity and manipulability to the inner rod 1005 and at least a portion of the applicator tip 1006 to facilitate or improve the user's control of the applicator device 1002 during application of the substance 1001.

The inner rod 1005 can have a proximal end 1005a (not shown) and a distal end 1005b. The passageway 1007, if any, can extend from the proximal end 1005a to the distal end 1005b of the inner rod 1005. As shown, the applicator tip 1006 can be coupled with the distal end 1005b of the inner rod 1005. The proximal end of the inner rod 1005 can be manipulable by the surgeon or user of the device to advance, withdraw, rotate, and otherwise move the applicator tip 1006.

The cannula can optionally be flexible, semi-rigid, or rigid and can be formed from any suitable materials, including metal alloys, polymer materials, or otherwise. The system can optionally be configured to not have an outer sleeve 1003, wherein the inner rod 1005 and the applicator tip 1006 are sufficiently rigid and manipulable to not require the outer sleeve 1003.

In any arrangements disclosed herein, the applicator tip 1006 and/or other components can be pre-loaded in the cannula or outer sleeve 1003 such that the applicator tip 1006 need not be advanced into a proximal end of the cannula 1003 after the cannula 1003 has been advanced to the target location, and such that the size of the applicator device 1002 being advanced to the target location is defined by the size of the cannula 1003 and not the larger applicator tip 1006, thereby improving maneuverability of the device and reducing risk of injury the patient. Optionally, the applicator device 1002 can be configured such that the applicator tip 1006 is advanced into the proximal end of the cannula 1003 after the cannula 1003 has been advanced into the target location. A proximal end of the cannula 1003 can be flared or tapered to facilitate the insertion of the applicator portion 1010 of the applicator tip 1006 into the cannula 1003 and/or facilitate the collapse and/or rolling or furling of the applicator portion 1010 for insertion into the cannula 1003.

As mentioned, when the applicator tip 1006 is in the first or withdrawn state (i.e., within the cannula 1005), the distal portion of the applicator device 1002 can have a smaller profile or cross-sectional size which can be defined by the outer sleeve 1003 so as to be advanceable through an opening in a tissue surface with less force required and, consequently, less risk of trauma to the tissue. Some arrangements of the applicator device 1002 can be configured such that, when the applicator portion 1010 is withdrawn within or positioned within the outer sleeve 1003, the applicator portion 1010 can be biased to assume a curved, furled, folded, or rolled shape so as to fit within the inner space of the outer sleeve 1003, as best shown in FIG. 45.

With reference to FIG. 45, the applicator portion 1010 can be configured such that, when the inner rod 1005 and the applicator tip 1006 are withdrawn back into the outer sleeve 1003 from the second state to the first or withdrawn state, the applicator portion 1010 can be biased or otherwise configured to collapse to a more compact or narrow shape or state described above and shown in FIG. 45 so that the applicator device 1002 can be withdrawn through the opening in the tissue with the applicator tip 1006 withdrawn within the outer sleeve 1003. As shown and described, the applicator portion 1010 can have a width W that is greater than a width of the outer sleeve 1003. Because the applicator portion 1010 is configured or biased to move to a more compact profile upon withdrawal into the cannula 1003, withdrawing the applicator portion 1010 within the outer sleeve 1003 as shown in FIG. 45 can reduce the size of the distal portion of the applicator device 1002 to the size of the outer sleeve 1003, thereby reducing trauma to the patient during withdrawal of the device. In any arrangements, the applicator portion 1010 can be configured to have any features or be made from any materials that allow it to be folded, rolled, compressed, squeezed, narrowed or otherwise reduced in width W or size to fit within the outer sleeve when withdrawn within the outer sleeve.

The applicator portion 1010 can have or define a first width when the applicator portion 1010 is in the first position (wherein the applicator portion 1010 is contained within the outer sleeve 1003) and a second width when the applicator portion 1010 is in the second position (wherein the applicator tip extends past the opening at the distal end 1003a of the outer sleeve 1003). The second width of the applicator portion 1010 can be substantially greater than the first width of the applicator portion 1010. In any arrangements disclosed herein, the second width of the applicator portion 1010 can be approximately 5 times greater than the first width of the applicator portion 1010, or from approximately 2 times greater (or, optionally, less) to approximately 8 times greater (or, optionally, more) than the first width of the applicator portion 1010, or from approximately 3 times greater to approximately 6 times greater than the first width of the applicator portion 1010.

The inner rod 1005 can be advanced relative to the outer sleeve 1003 so that a distal end portion 1006a of the applicator tip 1006 can extend out of a distal end 1003a of the cannula 1003. In any arrangements, the applicator tip 1006 can have an elongate portion 1008 and an applicator portion 1010. The elongate portion 1008 of the applicator tip 1006 can optionally have a passageway 1012 extending therethrough from a proximal end 1008a to a distal end 1008b of the elongate portion 1008. The passageway 1012 can, in an operable state, be in fluid communication at the proximal end 1008a of the elongate portion 1008 with the passageway 1007, if any, of the inner rod 1005. One or, optionally, a plurality of openings 1014 can optionally be formed through a first surface 1011 of the applicator portion 1010, the openings or orifices 1014 being in fluid communication with the passageway 1012. The openings 1014 can be used to transmit a source of suction or negative pressure or a positive pressure or airflow to any objects in close proximity to the applicator portion 1010 or in contact with the applicator portion 1010. The source of suction can be communicated to the openings 1014 through the passageways 1007 and 1012, from, for example, a proximal end of the device such as through a handle coupled with the outer sleeve of the device. For example, a suction force can be applied through the openings to selectively attract and secure any desired objects against the first surface 1011 of the applicator portion 1010 including, without limitation, one or more bubbles comprising a substance (with, optionally, a gentle suction force to avoid bursting the bubble), a patch, tissue cover, scaffolding, or other object. For example and without limitation, a gentle suction force can be applied through the openings 1014 to attract and secure a bubble comprising a substance against the first surface 1011 of the applicator portion 1010.

Thereafter, the applicator portion 1010 can transfer the bubble to a desired location, such as a tissue defect in a surgical airspace within an eye. The substance can be released from the applicator portion 1010 by reducing the suction force or negative pressure provided through the openings 1014, by pressing and/or manipulating the applicator portion 1010 against the target surface, and/or by exerting a positive pressure through the openings, such as optionally a short burst or positive pressure. A supply of positive pressure (e.g., through a provision of a positive airflow through the opening or openings 1014) can be used to facilitate the release of the bubble.

Figure 46:
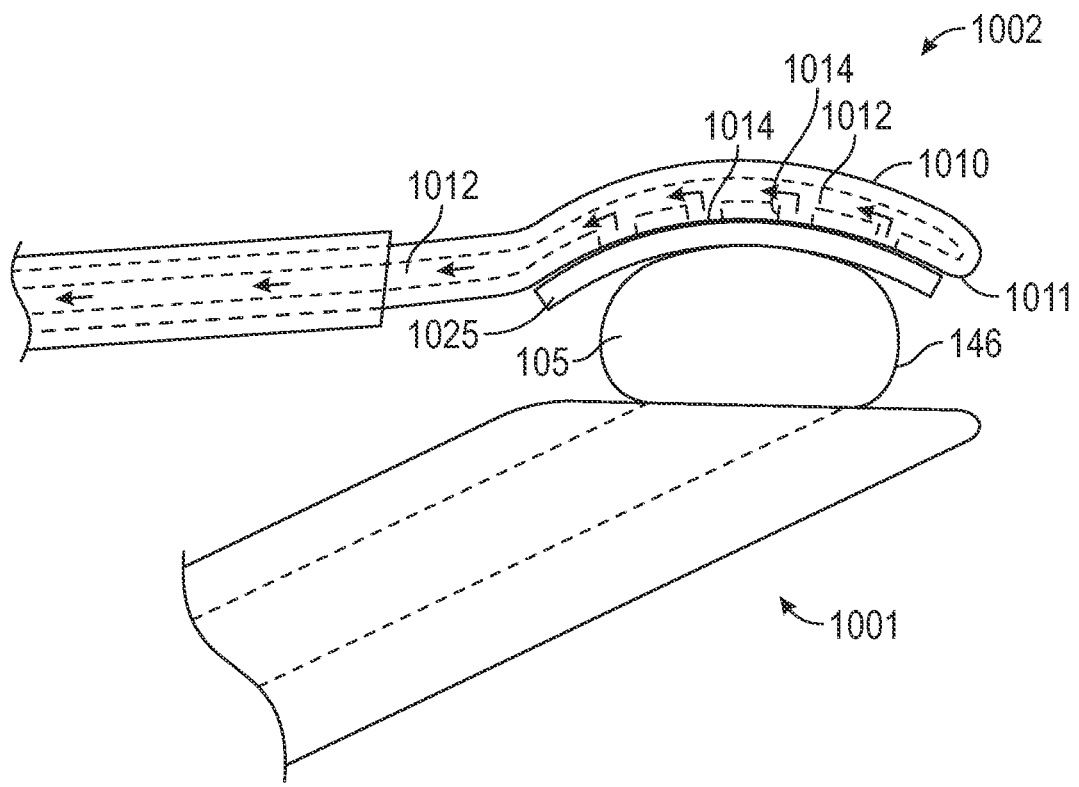
FIG. 46 is a side view of a non-limiting example of an applicator device and a substance providing device, showing the substance providing device depositing a bubble of a substance against a surface of a patch supported by an applicator tip of the applicator device.

In another nonlimiting example, negative pressure can be used to selectively secure a patch or any other implement against the first surface 1011 of the applicator portion 1010. For example, as shown in FIG. 46, a source of suction can be applied through the openings 1014 to a patch or other medical implement 1025 to selectively and releasably hold the patch 1025 against the first surface 1011 of the applicator portion 1010. Thereafter, the patch 1025 can be delivered to a desired location and advanced into contact with the target tissue surface by advancing the applicator device 1002 to the target location. When the desired position of the patch 1025 has been achieved, and the patch has optionally been retained in position long enough to secure the patch to the target tissue surface, the negative pressure may be reduced and the patch released from the applicator portion 1010. A positive pressure or airflow can optionally be provided through the openings to facilitate the release of the patch.

Figure 47:
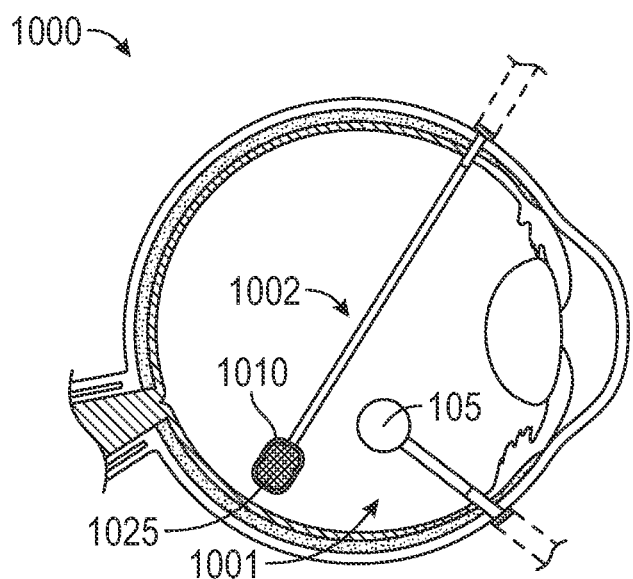
FIG. 47 is another illustration of the system having the applicator device and the substance providing device.

Additionally, with reference to FIG. 46, a source of suction can be applied through the openings 1014 to a patch or other medical implement 1025 to selectively and releasably hold the patch 1025 against the first surface 1011 of the applicator portion 1010. Thereafter, the substance supply device 1001 (which can be or have any of the components or details of any of the arrangements of the bubble, loop, or other substance supply devices disclosed herein) can provide a bubble 146 or layer of substance 105 on a surface of the patch 1025. The substance 105 can be a bioadhesive. The bubble 146 and/or the substance 105 can be applied against the patch as described above for device 130 in FIGS. 4A-4D. After the substance 105 has been applied to the patch, the patch 1025 can be delivered to a desired location and the adhesive coated surface of the patch 1025 can be advanced into contact with the target tissue surface by advancing the applicator device 1002 to the target location, as shown in FIG. 47. When the desired position of the patch 1025 has been achieved, and the patch has optionally been retained in position long enough to secure the patch to the target tissue surface, the negative pressure may be reduced and the patch released from the applicator portion 1010. In any arrangements, the applicator portion 1010 may be biased and configured such that, as the applicator portion 1010 is withdrawn into the cannula 1003, interaction with the distal end of the cannula 1003 will cause the applicator portion 1010 to assume a folded or furled shape so that the applicator portion 1010 can be completely withdrawn into the cannula.

In other arrangements, the applicator portion 1010 can be solid and without any openings or orifices therein. Additionally, the applicator tip 1006 can have a planar shape, a curved shape as shown in FIG. 46, or otherwise. In other arrangements, clips, tabs, depressions, ridges or protrusions, or other features can be used to selectively and releasably retain the patch or other medical implement to the first surface 1011 of the applicator portion 1010. In other arrangements, the applicator portion 1010 and applicator device 1002 can be configured so that a patch, cover, or other medical implement can rest freely on the first surface 1011 of the applicator portion 1010. In any arrangements, the patch can come preloaded in the cannula 1002, and can be rolled up against the surface 1011 of the applicator portion 1010 so that, as the applicator portion 1010 is advanced out of the distal end of the cannula 1003, the applicator portion 1010 can self-expand or open up to an open shape, with the patch 1025 still retained against the first surface 1011 of the applicator portion 1010.

In any arrangements, the patch can be secured at a proximal end of the patch using end-grasping forceps that are extendable from a cannula. The forceps can be self-expanding such that, as the cannula is retracted relative to the forceps or the forceps are advanced distally relative to the distal end of the cannula, the forceps will open up and release the grip on the patch. In this arrangement, the patch can be preloaded inside a distal end of the cannula with at least a portion of the patch grasped by the forceps. Because the forceps are constrained by the cannula, the forceps will retain their grasp on the patch until the forceps are advanced distally out of the cannula or the cannula is withdrawn proximally relative to the forceps. For example, as the forceps are advanced distally relative to the cannula, the patch can be moved past the distal end of the cannula and allowed to unfold, unroll, or unfurl into a relaxed, expanded state while the forceps are still sufficiently constrained in the closed position by the cannula such that the forceps continue to grasp the patch. In this state and position, a substance such as a bioadhesive can be applied to a desired surface of the open or relaxed patch using any of the substance applicator devices disclosed herein, for example and without limitation device 130. The substance can be applied as a bubble, a plurality of bubbles, or otherwise. The substance applicator can also optionally be used to spread the substance over the surface of the patch. After the adhesive has been sufficiently applied to the surface of the patch, the patch can be positioned in contact with the desired tissue surface until the substance has created a sufficient bond between the patch and the tissue surface. Thereafter, the forceps can be further expanded to release the grasp of the forceps on the patch by advancing the forceps distally relative to the cannula and/or retracting the cannula to permit the forceps to expand, by button or slide action, or otherwise. Thereafter, the forceps can be withdrawn back into the cannula and withdrawn from the surgical site.

The forceps or other grasping means disclosed in any arrangements herein can be or include the ALCON Revolution DSP forceps or GRIESHABER DSP forceps. For example, such forceps can be use to grasp and/or manipulate a patch used in any arrangements disclosed herein.

The patch can also be released from the applicator portion using any mechanical components, including a button, that a surgeon or user can advance to advance the end-grasping forceps and attached patch and/or patch material. If the forceps are loaded into the passive-open position, then once the forceps are extended past the distal tip of the cannula, the forceps can be biased or configured to open or return into their open or relaxed state.

In another method, the same internal end-grasping forcep can pinch the patch in its tips, but use a button in the reverse manner—to retract the cannula from around the end-grasping forceps and attached patch. This can allow surgeon to hold the tip of the cannula close to the target tissue and slowly expose the patch without actually advancing the patch forward, thereby avoiding hitting the retina with the patch which can occur if the surgeon does not compensate by gradually pulling the cannula back away from retina as tip advances. Once the cannula is fully retracted proximal to the tips of the end-grasping forceps, the forceps would be biased to passively open and release the patch or spatula or both.

Additionally, some arrangements can have a selectively disconnectable connector 1022 that couples the proximal end 1008a of the elongate body 1008 with the distal end 1005b of the inner rod 1005. In some arrangements, the applicator tip 1006 including, hence, at least the applicator portion 1010, can be released from the inner rod 1005 by disengaging the connector 1022. This can allow the applicator tip 1006 to be removed from the device and left in situ within the patient's body. In this configuration, the applicator portion 1010 can essentially be the patch or cover for the defect. The applicator tip 1006 can be made from any suitable material, including any suitable bioabsorbable or biocompatible materials.

In any arrangements of the applicator device 1002 or any substance supply device embodiments disclosed herein, the handle, cannula or outer sheath 1003, the inner sheath 1005, or other rigid or semi-rigid components can be made from or comprise any suitable plastic material, patch material, metal, polyvinyl chloride, glass, acrylic, carbon fibers and/or any combination of the foregoing. In some arrangements, the cannula tip plug or protective tip cover can comprise plastic, metal, polyvinyl chloride, glass, acrylic, carbon fibers, rubber (such as, without limitation, silicon), and/or any combination of the foregoing.

Figure 48:
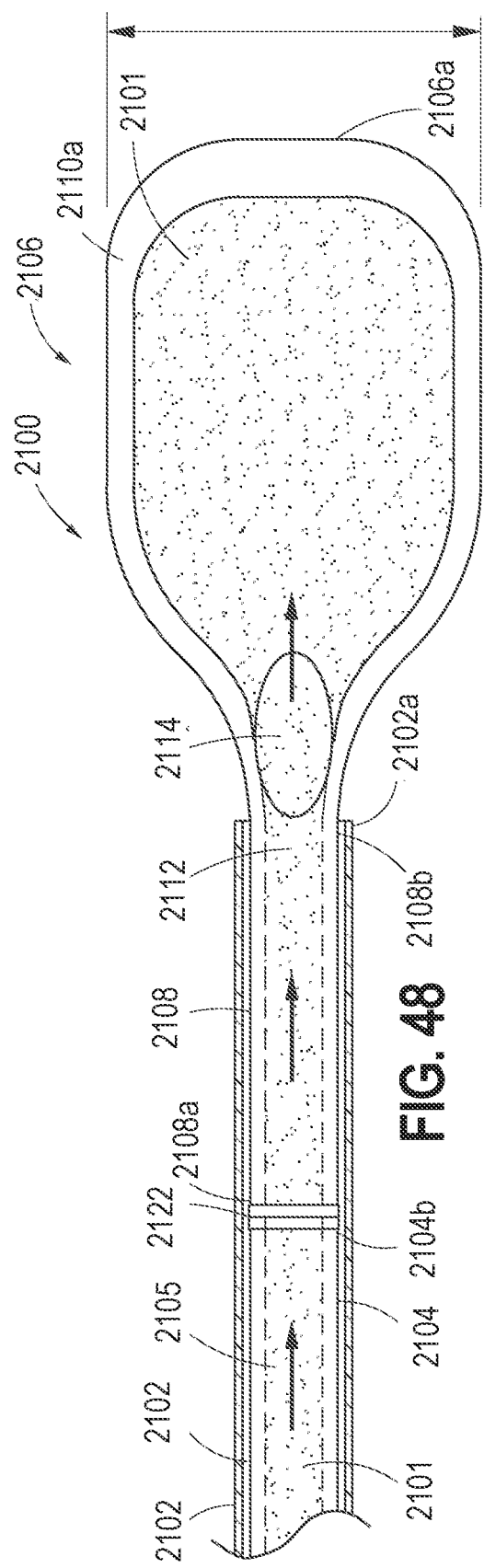
FIG. 48 depicts a top view of an embodiment of a device for application of a substance to a surface of an object, showing the device in a second or extended state.
Figure 49:
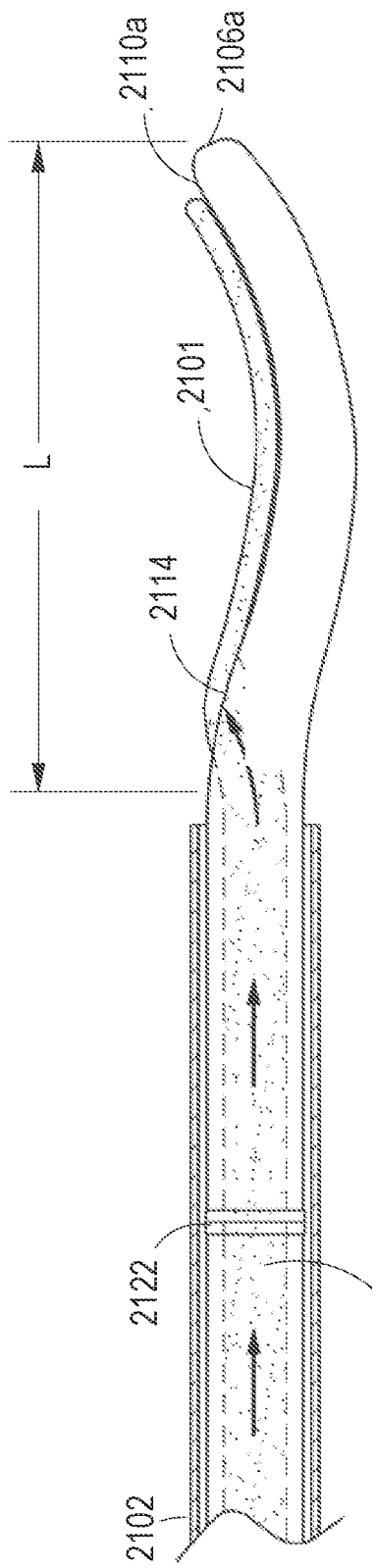
FIG. 49 depicts a side view of the embodiment of the device shown in FIG. 48, showing the device in the second or deployed state.

FIGS. 48 and 49 depict a top view and a side view, respectively, of an embodiment of a device 2100 (also referred to herein as a delivery device) for application of a substance 2101 to a surface of an object. In some embodiments, the device 2100 can include a cannula or outer sleeve 2102 (also referred to herein as an elongate body or outer sheath), an inner sleeve 2104 (also referred to herein as an inner cannula) having a lumen or passageway 2105 therein through which the substance 2101 can be advanced, and an applicator 2106 (also referred to herein as an applicator tip) coupled with the inner sleeve 2104. The outer sleeve 2102 can be configured to provide additional rigidity and manipulability to the inner sleeve 2104 and at least a portion of the applicator 2106 to facilitate or improve the user's control of the device 2100 during application of the substance 2101.

The inner sleeve 2104 can have a proximal end 2104a (not shown) and a distal end 2104b. The passageway 2105 can extend from the proximal end 2104a to the distal end 2104b of the inner sleeve 2104. As shown, the applicator 2106 can be coupled with the distal end 2104b of the inner sleeve 2104.

The cannula can optionally be flexible, semi-rigid, or rigid and can be formed from any suitable materials, including metal alloys, polymer materials, or otherwise. The system can optionally be configured to not have an outer sleeve 2102, wherein the inner sleeve 2104 and the applicator 2106 are sufficiently rigid and manipulable to not require the outer sleeve 2102.

In any embodiments disclosed herein, the applicator 2106 and/or other components may be pre-loaded in the cannula or outer sleeve 2102 such that the applicator 2106 need not be advanced into a proximal end of the cannula 2102 after the cannula 2102 has been advanced to the target location. Optionally, the device 2100 can be configured such that the applicator 2106 is advanced into the proximal end of the cannula 2102 after the cannula 2102 has been advanced into the target location. A proximal end of the cannula 2102 can be tapered to facilitate the insertion of the applicator portion 2110 into the cannula 2102 and/or facilitate the collapse and/or rolling of the applicator portion 2110 for insertion into the cannula 2102.

In any embodiments of the device 2100, the handle, cannula or outer sheath 2102, the inner sheath 2104, or other rigid or semi-rigid components can be made from or comprise a any suitable plastic material, metal, polyvinyl chloride, glass, acrylic, carbon fibers and/or any combination of the foregoing. In some embodiments, the cannula tip plug or protective tip cover can comprise plastic, metal, polyvinyl chloride, glass, acrylic, carbon fibers, rubber (such as, without limitation, silicon), and/or any combination of the foregoing.

A distal end portion 2106a of the applicator 2106 can extend out of a distal end 2102a of the cannula 2102. In any embodiments, the applicator 2106 can have an elongate portion 2108 and an applicator portion 2110. The elongate portion 2108 of the applicator 2106 can optionally have a passageway 2112 extending therethrough from a proximal end 2108a to a distal end 2108b of the elongate portion 2108. The passageway 2112 can, in an operable state, be in fluid communication at the proximal end 2108a of the passageway 2108 with the passageway 2105 of the inner sleeve 2104. An opening or orifice 2114 can be positioned at a distal end 2108b of the body 2108 and can be in fluid communication with the passageway 2112. Some embodiments can have a connector 2122 that couples the proximal end 2108a of the body 2108 with the distal end 2104b of the inner sleeve 2104. In this embodiment, the substance 2101 can be advanced through the passageway 2105 of the inner sleeve 2104, through the connector 2122, through the passageway 2112 extending through the elongate portion 2108 of the applicator 2106, and be expressed out through the opening 2114 onto a first surface 2110a of the applicator portion 2110 of the applicator 2106.

In another embodiment, as shown in FIGS. 57 and 58, the device 2300 can have an outer sleeve 2302 and an applicator portion 2310, and an additional movable cannula 2338 having a passageway 2340 positioned within the outer sleeve or cannula 2302. The passageway 2340 can optionally provide a passageway for the transmission or provision of substance 2101 (which can, optionally, be the substance described above or in any other embodiments disclosed herein or any other desired material) onto various parts of applicator portion 2310. As will be described, the movable cannula 2338 (also referred to herein as a fill or refill cannula) can be configured to be moveable relative to the outer sleeve 2302, and/or at least a portion of the applicator 2306 from at least a first position, as illustrated in FIG. 57, to a second position, as illustrated in FIG. 58. The applicator 2306 and applicator portion 2310 can have any of the features, materials, or other details of any of the other applicators and applicator portions disclosed herein, including without limitation applicator 2106 and applicator portion 2110.

In any embodiments disclosed herein, the device can have an outer sleeve and an applicator portion, and an additional fixed lumen or cannula (such as, for example, a fixed version of cannula 2338) having a passageway therein within the outer sleeve or cannula. The lumen or cannula can provide a passageway for the transmission or provision of substance 2101 (which can, optionally, be the substance described above or in any other embodiments disclosed herein, or any other desired material) onto the applicator portion 2310. For example and without limitation, the substance can be exuded through an opening at a distal end of the lumen or cannula and onto the applicator portion. Further, some embodiments of the device can be configured such that the substance can be first exuded on a distal or leading edge of the applicator portion, and then across a length of the applicator portion as the applicator portion is extended in the distal direction, as substance is continuously injected and exuded through the opening at the distal end of the substance supply lumen or passageway. In some embodiments, the distal end of the substance supply lumen or cannula can be configured to exude the substance in a wide band on the applicator portion, such as through multiple openings, a manifold, or a wide slot opening. In some embodiments, the only movable or extendable component of the device or a distal end portion of the device can be the applicator and applicator portion (which can be integrally connected).

In practice, after the applicator 2306 is advanced to its fully extended position, the cannula 2338 can be advanced to, for example and without limitation, the distal portion of the applicator portion 2310, i.e., the first position shown in FIG. 57. The substance 2101 can be advanced through the passageway 2340 and onto the distal portion 2310a of the applicator portion 2310 first. Then, as the cannula 2338 is retracted (which can, optionally, be done slowly for better control and coverage of the applicator portion 2310) toward the second position (as shown in FIG. 58), the user can continue to eject substance on middle portions and/or the proximal portion of the applicator portion 2310. In this configuration, the user (who can optionally be a surgeon or other medical practitioner) can achieve a more even consistency and distribution of the substance over some or all portions (distal, medial, and proximal portions) of the applicator portion 2310 using the moveable cannula. In some embodiments, the movable cannula can enable a more even consistency and distribution of the substance over some or all portions (distal, medial, and proximal portions) of the applicator portion 2310 as compared to a fixed passageway or cannula.

Additionally, in any embodiments disclosed herein, the device can have a first or fixed inner cannula (such as cannula 2104) and a moveable cannula surrounding an outside surface of the inner cannula 2104, which is advanceable as described above through the passageway through the distal tip. In these embodiments, two passageways can be used to provide a substance to the applicator portion. The moveable passageway, which can optionally be an additional cannula or sleeve, can be configured to be advanceable and retractable relative to the inner cannula 2104, passageway through the applicator, and/or the applicator portion.

Thereafter, once the substance 2101 has been advanced onto the first surface of the applicator portion 2110 (or 2310) of the applicator 2106, the user can apply the substance 2101 to the desired surface. For example, in applications where the device 2100 is used for application of a therapeutic substance to an ocular surface, the surgeon or medical practitioner can advance the substance 2101 onto the first surface 2110a of the applicator portion 2110 of the applicator 2106 in there after use the applicator portion 2110 to apply the substance 2101 to the target portion of the ocular surface. In any embodiments, the applicator 2106 can be made from or otherwise configured to be flexible and conformable to reduce the risk of any puncture or other damage to the tissue to which the substance 2101 is applied. In some embodiments, the applicator 2106 can be made from a medical grade silicone material, one or more biodegradable materials, one or more different types of alloys, including stainless steel and Nitinol, or any other suitable rubber or other flexible polymeric materials. In any embodiments, the applicator portion 2110 can be made from a material designed to enhance the thermal conductivity of the applicator portion 2110, i.e., from a material that has enhanced thermal conductivity properties to better enable the applicator portion 2110 to transfer heat or cooling.

Any embodiments of the device 2100 can optionally have a distal tip (not shown) coupled with a distal end 2102a of the outer sheath or cannula 2102. The distal tip can optionally have a conical or tapered profile, and can be made from a flexible material such as silicone or other suitable polymers, alloys such as stainless steel or Nitinol, etc. Alternatively, in other embodiments, the distal end 2102a of the cannula 2102 can have an angled or beveled end surface configured to facilitate the advancement of the distal end 2102a through an opening in a tissue surface or other opening.

In other embodiments the distal end 2102a may be pointed and sharp, like a hollow needle tip, to allow insertion through tissue, such as through the sclera to access the subretinal space. Optionally, the device of any embodiments disclosed herein can have a distal tip portion distal to the cannula 2102 comprising a softer material, such as a flexible silicone. The soft tip portion can be used in some applications to reduce the risk of trauma to the tissue surface. Additionally, in any embodiments, the soft tip portion can also be used to brush the surface of the tissue to gently spread or move the substance, remove substance from the tissue, or otherwise.

The device 2100 can also optionally have a removable distal plug or tip cover that can be removably coupled with a distal end 2102b of the cannula 2102 and/or a distal tip of the device 2100. The distal plug or tip cover can provide a seal with the passageway through the cannula 2102, and can be removed prior to advancement of the device into the target tissue area to provide a seal for the device to maintain sterility within the device and also for sealing off the passageway through the cannula in devices that are pre-filled with sub stance.

Additionally, as most clearly shown in FIG. 49, some embodiments of the applicator 2106 can have a curved profile in at least one of a length direction L (identified in FIG. 49) and a width direction W (identified in FIG. 48). For example and without limitation, some embodiments of the applicator portion 2110 can have a curved profile or slightly curved profile in both the lengthwise direction and the widthwise direction, wherein the curved profile is sized and configured to be similar to a curvature of the target tissue surface (which can, optionally, be a retinal surface or other ocular surface of a human eye, an eye of an animal or living being, or otherwise) and/or to better hold the desired substance on the applicator portion. In other embodiments, the applicator portion 2110 can be configured to improve the ability of the applicator portion 2110 to hold the substance 2101 on the applicator portion 2110, particularly when the applicator portion 2110 is rotated, tilted, and/or turned upside down. In other embodiments, the applicator portion 2110 can have a generally flat profile or shape, or any other desired profile or shape.

The cannula 2102 and/or cannula (or inner sleeve) 2104 of any embodiments disclosed herein can optionally have a tubular shape and a size that is approximately 25 gauge (0.455 mm size), or 27 gauge (0.361 mm size), or that is from or from approximately 28 gauge (0.33 mm size) or smaller to or to approximately 20 gauge (0.813 mm) or larger, or from 27 gauge (0.361 mm size) to or to approximately 24 gauge (0.511 mm), or of any values or from and to any values within these ranges. Optionally, in other embodiments, larger cannula or smaller cannula can be used for the inner and/or outer cannula or sleeves.

In any embodiments, the cannula, cannula base, cannula body, and/or cannula tip can have a 0.1-0.5 mm, 0.5-1 mm, 1-2 mm, 2-3 mm, 3-4 mm, 4-5 mm, 5-6 mm, 6-7 mm, 7-8 mm, 8-9 mm or 9-10 mm cross-sectional diameter. Optionally, the cannula, cannula base, cannula body, cannula tip and/or cannula exit port can have a length of 0.1-0.5 mm, 0.5-1 mm, 1-2 mm, 2-3 mm, 3-4 mm, 4-5 mm, 5-6 mm, 6-7 mm, 7-8 mm, 8-9 mm, 9-10 mm, 10-20 mm, 20-30 mm, 30-40 mm or 40-50 mm. Additionally, the cannula, cannula base, cannula body, cannula tip and/or cannula exit port can have an external diameter, an internal diameter and a width between the internal diameter and the external diameter of 0.01-0.05 mm, 0.05-0.1 mm, 0.1-0.5 mm, 0.5-1 mm, 1-2 mm, 2-3 mm, 3-4 mm, 4-5 mm, 5-6 mm, 6-7 mm, 7-8 mm, 8-9 mm, 9-10 mm, 10-20 mm, 20-30 mm, 30-40 mm or 40-50 mm.

For other applications outside of ocular applications, the cannula 2102 can optionally have a tubular shape and a cross-sectional size or inner diameter that is from or from approximately 10 mm to or to approximately 200 mm or more, or from or from approximately 40 mm to or to approximately 80 mm.

Some embodiments of the devices and methods disclosed herein can be configured to deliver and apply a variety of materials or substances of varying viscosities to the target tissue or surface. Examples of substances that can be used with any of the devices, systems, and methods disclosed herein include, without limitation, adhesives, bioadhesives, gels, hydrogels, thick liquids or semi-liquid treatment substances, double layer hydrogels, nonsolids, a polyethylene glycol solutions, a trilysine amine solutions, polymeric hydrogels, thermoresponsive gels, and any combination of the foregoing. Examples of bioadhesive substances that can be used in any embodiments disclosed herein includes, without limitation, ReSure™ sealant, a polyethylene glycol hydrogel and other hydrogels, cyanoacrylate, fibrin glue, a polyethylene glycol solution, trilysine amine solution, glycoproteins, elastic proteins, carbohydrates, mucopolysaccharides, etc. In some embodiments of the system or device, the bioadhesive material comprises a resin. UV or light activated bioadhesives can also optionally be used with any device embodiments disclosed herein. In some such embodiments, the system, kit or device can incorporate a light or light fiber for activating the bioadhesive material.

Temperature activated bioadhesives can also optionally be used with any device embodiments disclosed herein. In some such embodiments, the system, kit or device can incorporate a material that conducts heat for activating the bioadhesive material.

In some embodiments, the substance can include an adhesive or bioadhesive. The term, "adhesive," as used herein, shall be given its ordinary meaning and also is intended to encompass a bioadhesive. Examples of adhesives that can be used with any embodiments disclosed herein include but are not limited to polyvinyl acetate, glue, aliphatic, cyanoacrylate, epoxy, polyurethane glue, and contact cement. Examples of bioadhesives include but are not limited to. In some embodiments the adhesive is a biomimetic material. In some embodiments, the adhesive is not a bioadhesive.

Any embodiments disclosed herein can also be configured to use one or more substances that polymerize as the temperature of the substance reaches a threshold value or range of values, such as for example and without limitation, normal body temperature, or to any values from 80° F. or from approximately 80° F. to or to approximately 100° F. or greater, or from or from approximately 90° F. to 100° F. or to approximately 100° F. or greater, or from 95° F. or from approximately 95° F. to 100° F. or to approximately 100° F. or greater, or to and from any values within these ranges. Additionally, any embodiments can be used to apply a cold cured substance to a tissue surface—i.e., substances that polymerize as the temperature of the substance drops to a threshold value or range of values, such as for example and without limitation, 10° F. below body temperature, or to any values from 70° F. or from approximately 70° F. or less to 90° F. or to approximately 90° F., or from 80° F. or from approximately 80° F. to 90° F. or to approximately 90° F., or to and from any values within these ranges.

Any embodiments disclosed herein can also be configured to use one or more substances that polymerize with activation by any number of various wavelengths of light, or are activated by light. Activation light may be provided by special applicator within or separate from the material delivery device. Suitable substances that can be used also include substances that are typically used in or are approved for use in subretinal space, a vitreous cavity, or an ocular surface including on or under conjunctiva, and substances that may be used for closing gaps in tissue.

In any embodiments, the applicator portion 2110 can be biased to be sufficiently flexible or otherwise structurally biased to be collapsible in the width direction W so as to be withdrawable within the outer sleeve 2102 and also so as to minimize forces exerted on and resultant trauma that may occur from a more rigid material. FIGS. 50 and 51 depict a side view and an end view, respectively, of the embodiment of the device 2100 shown in FIG. 48, showing the device in a first or withdrawn state wherein the applicator portion 2110 is contained or withdrawn into the outer sleeve 2102. FIG. 52 is an end view of another embodiment of the device 2100 and the applicator portion 2110.

The inner sleeve 2104 and applicator 2106 can optionally be advanceable and withdrawable through the lumen or passageway 2103 of the outer sleeve 2102, such as between the first state illustrated in FIGS. 50-51 and the second or deployed state illustrated in FIGS. 48-49.

When the applicator 2106 is in the first or withdrawn state, the distal portion of the device 2100 can have a smaller profile or cross-sectional size which can be defined by the outer sleeve 2102 so as to be advanceable through an opening in a tissue surface with less force required and, consequently, less risk of trauma to the tissue. Some embodiments of the device 2100 can be configured such that, when the applicator portion 2110 is withdrawn within or position within the outer sleeve 2102, the applicator portion 2110 can take a curved or helical shape so as to fit within the inner space of the outer sleeve 2102, as best shown in FIGS. 51 and 52 and, thereby, form a space 2130 confined by the first surface 2110a of the applicator portion 2110.

With reference to FIG. 52, the applicator portion 2110 can be configured such that, when the inner sleeve 2104 and the applicator 2106 all withdrawn back into the outer sleeve 2102 from the second state to the first or withdrawn state, the applicator portion 2110 can be biased or otherwise configured to collapse to a more compact or narrow shape or state described above and shown in FIG. 52 so that the device 2100 can be withdrawn through the opening in the tissue with the applicator 2106 withdrawn with in the outer sleeve 2102. As shown and described, the applicator portion 2110 can have a width W that is greater than a width of the outer sleeve 2102. Because the applicator portion 2110 is configured or biased to move to a more compact profile, withdrawing the applicator portion 2110 within the outer sleeve 2102 as shown in FIGS. 51 and 52 can reduce the size of the distal portion of the device 2100 to the size of the outer sleeve 2102. This can reduce the trauma to the tissue when the device 2100 is withdrawn through any openings, if any, in the tissue. In any embodiments, the applicator portion 2110 can be configured to have any features or be made from any materials that allow it to be folded, rolled, compressed, squeezed, narrowed or otherwise reduced in width W or size to fit within the outer sleeve.

The applicator portion 2110 can have or define a first width when the applicator portion 2110 is in the first position (wherein the applicator portion 2110 is contained within the outer sleeve 2102) and a second width when the applicator portion 2110 is the second position (wherein the applicator tip extends past the opening at the distal end 2102*a* of the outer sleeve 2102). The second width of the applicator portion 2110 can be substantially greater than the first width of the applicator portion 2110. In any embodiments disclosed herein, the second width of the applicator portion 2110 can be approximately 5 times greater than the first width of the applicator portion 2110, or from 2 times or approximately 2 times greater (or, optionally, less) to 8 times or approximately 8 times greater (or, optionally, more) than the first width of the applicator portion 2110, or from 3 times or approximately 3 times greater to 6 times or approximately 6 times greater than the first width of the applicator portion 2110.

In any embodiments disclosed herein, the second width of the applicator portion 2110 can be 2 mm, or approximately 2 mm, or 3 mm, or approximately 3 mm, or 4 mm, or approximately 4 mm, or from 1.5 mm or approximately 1.5 mm (or smaller) to 6 mm or approximately 6 mm (or larger), or from 2 mm or approximately 2 mm to 4 mm or approximately 4 mm, or from 2 mm or approximately 2 mm to 3 mm or approximately 3 mm, or any sizes within these ranges or from and to any sizes within these ranges. In other embodiments, wherein the device may be used for non-ocular tissue, the second width can be any values or from and to any values that are 2 times greater than the above-listed values or ranges, or 3 times greater than the above-listed values or ranges.

The applicator portion 2110 can be made of a solid, non-fenestrated material. Or, alternatively, the applicator portion 2110 can be made of a fenestrated material that has many openings or slits, or any combination thereof, like a sieve or fly swatter. The openings or slits can optionally be of variable sizes and/or dimensions.

An additional benefit of withdrawing the applicator portion 2110 within the sleeve 2102 is that, when the substance 2101 is advanced through the passageways formed in the inner sleeve 2104 and the applicator 2106, the substance 2101 can fill the space 2130 and thereby come into contact with and substantially cover the first surface 2110*a* of the applicator portion 2110. In this embodiment, to improve the coverage of the substance 2101 on the first surface 2110*a* of the applicator portion 2110, the user can withdraw the applicator portion 2110 within the outer sleeve so as to form the circular or rolled shape of the applicator portion 2110 and create the space 2130 within which the substance 2101 can be advanced and, optionally, substantially filled.

In any embodiments, the applicator portion 2110 can be withdrawn within the sleeve 2102 in an initial state of the device 2100. The substance 2101 can optionally be pre-dispensed within the passageways 2105, 2112 and within the volume 2130 before the device 2100 is advanced into the target location. Additionally, the substance can optionally be stored within the passageways 2105, 2112 and within the volume 2130 before the device is put into use. A thermoresponsive gel or other heat activated substance can be used in such embodiments to increase the shelf-life of a pre-filled device and reduce the likelihood of the substance curing during storage of the device or before application of the device. Heat from the patient's body or an added heat source (for example and without limitation, a heat source integrated into or applied to the applicator portion 2110) can be used to activate the thermoresponsive substance. In other embodiments, the user or surgeon can dispense the substance 2101 through the passageways 2105, 2112 after the device 2100 is advanced to the target location and/or after the applicator portion 2100 is advanced to the second or deployed state or position (shown in FIG. 48).

The device 2100 can optionally be configured such that the applicator 2106 can be selectively connectable to the inner sleeve 2104 at the connection 2122. In this configuration, the device 2100 can enable multiple additional capabilities that are not possible without the connectable interface 2122. As a first example, after the desired procedures have been formed in the substance 2101 has been applied to the target surface, a user of the device can disconnect the applicator 2106 from the inner sleeve 2104 at the connector 2122 so that outer sleeve 2102 and inner sleeve 2104 can be withdrawn from the target location without also withdrawing the applicator 2106 or portion thereof, such as the applicator portion 2110. For example, in some applications such as ocular applications, it may be desirable to leave the applicator 2106 in contact with the ocular tissue until the desired level of healing has been achieved or indefinitely. Thereafter, the distal tip 2106 or portion thereof can remain in the target location or can be removed from the target location by any suitable means, including by reconnecting the applicator 2106 with the inner sleeve 2104 and withdrawing the applicator 2106 within the outer sleeve 2102. The distal tip 2106 can be made from a bioabsorbable material, an inert material, or otherwise. If inert and left in the target location, the applicator portion 2110 can provide additional scaffolding or support to the tissue, even after the substance has dissolved or dissipated.

In any embodiments, any portions of the device 2100, including without limitation the passageway 2105 of the inner sleeve 2104, can be prefilled with a substance 2101 and stored in this partially filled condition. The applicator 2106 can be provided in an unattached or disconnected state wherein the applicator 2106 is disconnected from the inner sleeve 2104 and is free of any substance 2101. In this configuration, after the applicator 2106 is coupled with the inner sleeve 2104 at the connector 2122, the user can advance the substance 2101 through the passageway 2112 of the elongated portion 2108 of the application tip 2106, out through the opening 2114 and onto the applicator portion 2110 when the applicator portion 2110 is either the first state or the second state.

The connector 2122 in any embodiments disclosed herein can be configured to be self-sealing such that, when the applicator 2106 is disconnected from the inner sleeve 2104, the connector 2122 can seal the passageway 2105 of the inner sleeve 2104 to prevent the expulsion of any substance within the passageway number 2105 of the inner sleeve 2104 through the connector 2122.

Any embodiments of the applicator portion 2110 can optionally be configured to be less flexible in the lengthwise direction (indicated by L in FIG. 49) than in the width direction W. The material of the applicator portion 2110 can be configured to have stiffening features or materials, such as without limitation, stiffening wires, wire loops, ribs, sheets, or corrugations, or other structural members made out of Nitinol, stainless steel, or other alloys, channels, ribs, or other features such as in a lengthwise direction to increase a stiffness of the applicator portion 2110 in the lengthwise direction and decrease a stiffness of the applicator portion 2110 in the widthwise direction.

Additionally, some embodiments can optionally be configured to dispense or apply a flexible membrane of the substance to a surface, or to deliver any substance or material to an enclosed space, such as an eye, through a small opening in the eye.

Figure 53:
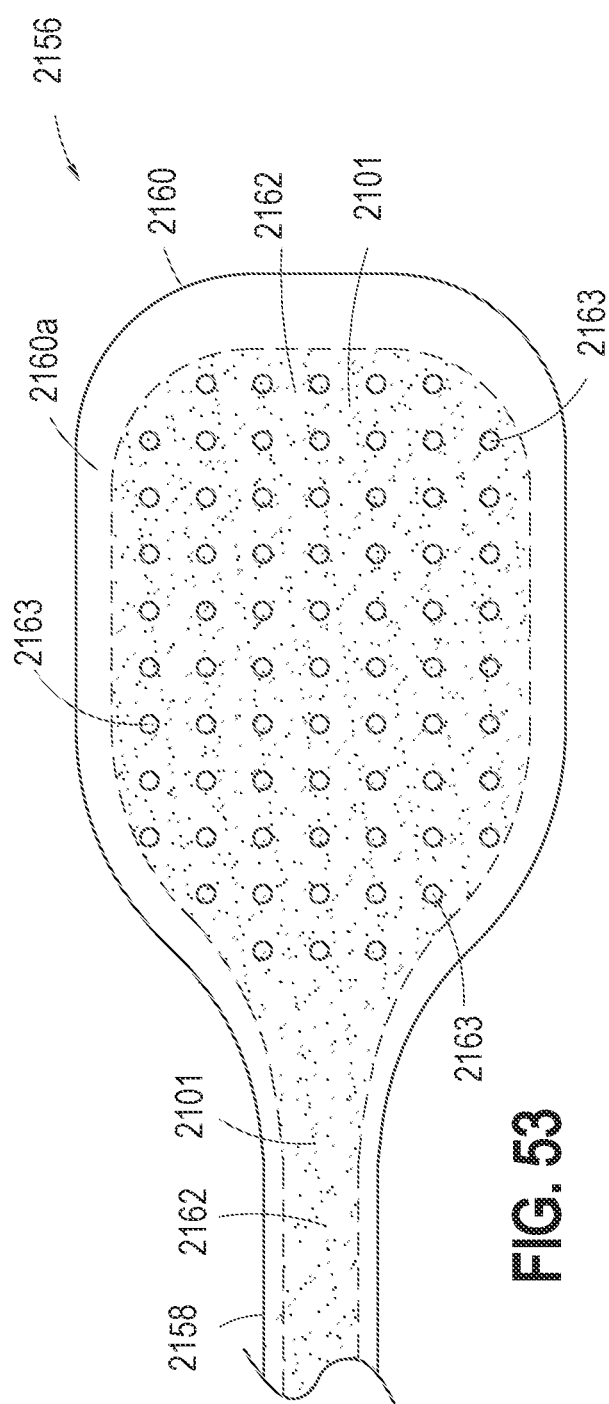
FIG. 53 depicts a top view of another embodiment of an applicator.

FIG. 53 depicts a top view of another embodiment of an applicator tip 2156 that can be used with any of the embodiments of the devices disclosed herein, including without limitation any of the devices 2100 disclosed above. The applicator tip 2156 can include any of the features, materials, or other details of any of the other applicator tip embodiments disclosed herein, including without limitation applicator 2106 described above, in combination with or in place of any of the features described below to form new embodiments.

With reference to FIG. 53, the applicator portion 2160 can include a plurality of openings 2163 in fluid communication with the passageway 2162 extending through the elongate portion 2158. The plurality of openings 2163 can be formed about the first surface 2160a of the applicator portion 2160 in any desired pattern and in any desired number. For example and without limitation, the applicator portion 2160 can have approximately 20 openings 2163 formed therein, or from 5 or approximately 5 to 40 or approximately 40 openings formed therein, or from 10 or approximately 10 to 30 or approximately 30 openings formed therein, or from 15 or approximately 15 to 25 or approximately 25 openings formed therein, or of approximately any number of openings 2163 within these ranges, or from and to any number of openings 2163 within these ranges.

The openings 2163 can provide for or enable a more even distribution of substance 2101 across the first surface 2160a of the applicator portion 2160. Additionally, the openings 2163, because they extend only through the first surface 2160a of the applicator portion 2160 to the passageway 2162, can increase the flexibility and/or collapsibility of the applicator portion 2160 so that the applicator portion 2160 to facilitate the collapse, bending, and/or withdrawal of the applicator portion 2160 within the outer sleeve of the device when the device is in the first or withdrawn state.

FIG. 54A depicts a section view of another embodiment of a device 2200 for application of a substance 2101 to a surface of an object, showing the device 2200 in the second or deployed state. The device 2200 can include any of the features, materials, or other details of any of the other device embodiments disclosed herein, including without limitation device 2100 described above, in combination with or in place of any of the features described below.

In some embodiments, the device 2200 can include a cannula or outer sleeve 2202 (also referred to herein as an elongate body) having a lumen or passageway 2203 therein through which the substance 2101 can be advanced, and an applicator tip 2206 coupled with an inner core 2204. The applicator tip 2206 and the inner core 2204 can be movable (e.g., extendable and retractable) within the outer sleeve 2202. In some embodiments, the applicator tip 2206 and the inner core 2204 can be rotatable within the outer sleeve 2202. The outer sleeve 2202 can be configured to provide additional rigidity and manipulability to the applicator tip 2206 to facilitate or improve the user's control of the device 2200 during application of the substance 2101, and also to advance the substance through the device 2200 to an applicator portion 2210 of the applicator tip 2206.

A distal end portion 2206a of the applicator tip 2206 can extend out of a distal end 2202a of the cannula or outer sleeve 2202. In any embodiments, the applicator tip 2206 can have an elongate portion 2208 and an applicator portion 2210. A seal 2222 can optionally be positioned at a distal end 2202a of the outer sleeve 2202 of the device 2200 to seal around an outside surface of the elongate body 2208 except for a channel or passageway that is aligned with a first surface 2210a (which can be referred to as an applicator surface) of the applicator portion 2210. Additionally, as with any embodiments disclosed herein, fluoroscopic or radiopaque markers can be positioned along the outer sheath 2202, such as a distal end 2202a of the outer sheath 2202, and/or along the applicator tip 2206 to provide visualization to a surgeon of the location of these components.

With this embodiment, as shown in FIG. 54A, a separate lumen through the elongate body 2208 and applicator tip 2206 need not be formed since the substance 2101 can be communicated through the space inside the outer sleeve 2202 between the outside surface of the elongate body 2208 and the inside surface of the outer sleeve 2202. In some embodiments, a channel or space can be formed along a length of an outside surface of the inner core 2204 or an inside surface of the outer sleeve 2202 along which or through which the substance 2101 can be advanced. In other embodiments, as shown in FIG. 54B, the outer sleeve 2202 can have a separate lumen 2203 through which the substance 2101 can be advanced.

In some embodiments, the elongate body 2208 can extend from at least a proximal end of the outer sleeve 2202 to the applicator portion 2210, such that no separate inner core is needed. In some embodiments, the proximal end of the elongate body 2208 or the inner core 2204 can extend past or through the handle (optionally, with appropriate seals, as needed) so that the user can manipulate the elongate body 2208 to advance and withdraw the applicator portion 2210 as needed. Similar to applicator portion 2110 described above, the applicator portion 2210 can be configured to be withdrawable within the outer sleeve 2202 and be configured to be moveable between the first or closed state and the second or extended state. For example and without limitation, the applicator tip 2206 can be withdrawn into the outer sleeve 2202 and then extended as substance 2101 is advanced past a distal end 2202a of the outer sleeve 2202, thereby applying the substance 2101 to a distal portion 2206a of the applicator tip 2206 and along a length of the applicator tip 2206 as the applicator tip 2206 is advanced distally relative to the distal end 2202a of the outer sleeve 2202.

In any embodiments of the device 2200, the handle, cannula or outer sheath 2202, the inner sheath 2204, or other rigid or semi-rigid components can be made from or comprise a any suitable plastic material, metal, polyvinyl chloride, glass, acrylic, carbon fibers and/or any combination of the foregoing. In some embodiments, the cannula tip plug or protective tip cover can comprise plastic, metal, polyvinyl chloride, glass, acrylic, carbon fibers, rubber (such as, without limitation, silicon), and/or any combination of the foregoing.

Any embodiments disclosed herein can have a handle (not shown) at the proximal end of the device 2100. The handle can have any details of any contemporary or existing designs of biomaterial or other liquid material delivery devices. In some embodiments, the handle can have a first handle portion or member that can be coupled to the outer sleeve 2102 of the device 2100. An additional or second handle can be coupled with the inner sleeve 2104. The second handle member can be independently movable relative to the first handle member so that a user can advance and withdraw the inner sleeve 2104 and, consequently, the applicator 2106, if coupled with the inner sleeve 2104, relative to the outer sleeve 2102.

A dispensing device or dispensing means (not illustrated) for dispensing the substance 2101 into the passageway 2105 can be in fluid communication with a proximal end 2104b of the inner sleeve 2104. The dispensing device can be coupled with or otherwise part of the handle of the device 2100. In some embodiments, the dispensing device can include a plunger or syringe, a fillable chamber that can be filled or contain the substance, a compressible bulb, a compressible bladder, or other device configured to eject the substance 2101 through the passageway 2105. Additional mechanisms for advancing the substance 2101 into the inner sleeve 2104 can include a mechanical pump, a powered pump, a pneumatic pump or cylinder, an electromechanical pumping means, etc. Optionally, the handle can include a port configured to receive an adhesive material into the handle. A bladder of material or other ejector device, such as is described herein, can be coupled in fluid communication with the port.

Figure 55A:
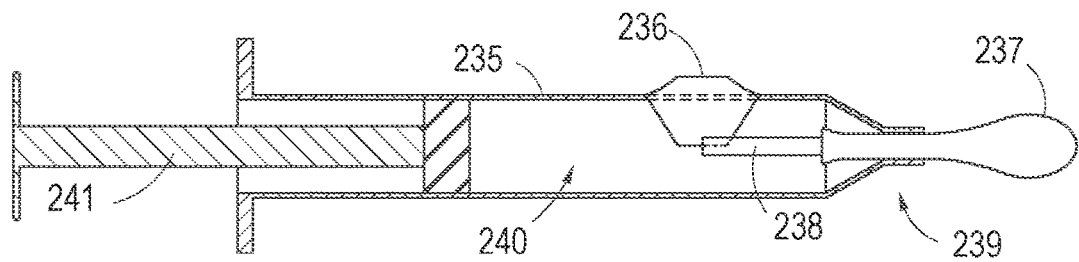
FIG. 55A depicts a non-limiting example of a system or device described herein.
Figure 55B:
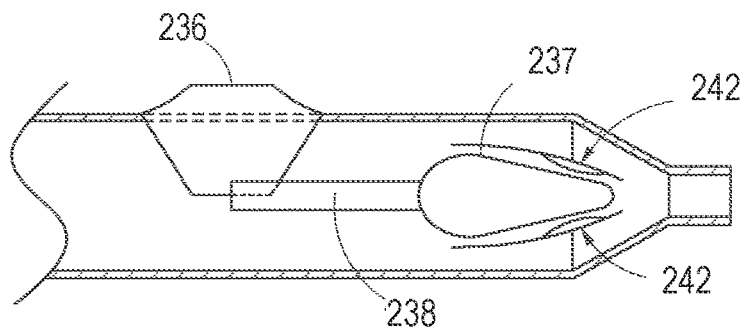
FIG. 55B depicts a non-limiting example of a system or device described herein.

FIG. 55A depicts an example of a system and/or device including a plunger 241, a handle 235, a cavity 240 for holding a bioadhesive material, an extender knob 236, a rod 238, a locking connector 239, and a flexible loop 237 containing a film of bioadhesive material 237 (partially extended). The plunger 241 may be used to expel a bioadhesive material through a hollow cannula and/or into the flexible loop 237 when pressed on by a user (for example, pressure from a user's finger or using pneumatic pressure supplied by an external device connected to the handle). In some embodiments, the plunger 241 is incorporated into the examples in FIGS. 55B and/or 55C. For example, the extender knob 236 may be used to extend the flexible loop 237 from a retracted position as seen in FIG. 55B. In some embodiments, the flexible loop 237 can be substituted with any of the applicator tips as disclosed elsewhere herein.

FIG. 55B depicts an example of a system and/or device that includes an extender knob 236, a rod 238, a flexible loop containing a film of bioadhesive material 237 and two guide ridges 242. Some embodiments include a retractable loop such as in FIG. 55B that expands out as shown in FIG. 55A and/or FIG. 55C.

Figure 55C:
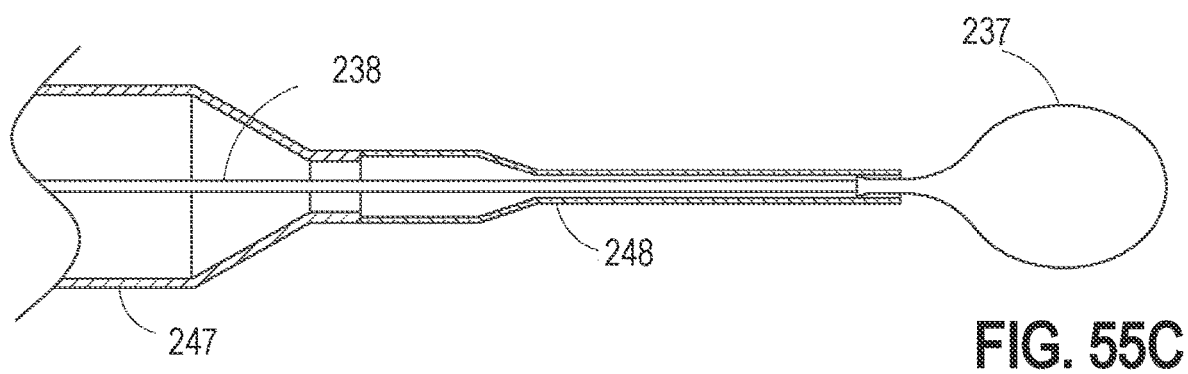
FIG. 55C depicts a non-limiting example of a system or device described herein.

FIG. 55C depicts an example of a system and/or device that includes a handle 247, a rod 238, a cannula 248, and a flexible loop containing a film of bioadhesive material 237. The cannula may be detachable or non-detachable.

Any components of the device 2100 in any embodiments disclosed herein, including without limitation the handle portion, the outer sleeve 2102, the inner sleeve 2104, and/or the distal tip 2106 can be configured to have temperature modulating capabilities. In some embodiments, the outer sleeve 2102, the inner sleeve 2104, and/or the distal tip 2106 can optionally be configured to dispel heat from the device that may result from any heat generated by the substance 2101 as the substance 2101 is advanced through the device 2100. For example, one or more of the outer sleeve 2102, the inner sleeve 2104, and the distal tip 2106 can optionally be made from materials or contain other materials such as thermally conductive metals (like copper, steel, Nitinol, aluminum, or other alloys, etc.) that have improved or enhanced thermal conduction which can conduct heat away from certain portions of the device 2100. In some embodiments, the outer sleeve 2102 and/or the inner sleeve 2104 can optionally be configured to conduct or dispel heat, while the applicator 2106 is not configured to dispel or conduct heat.

Alternatively, the outer sleeve 2102, the inner sleeve 2104, and/or the distal tip 2106 can optionally be configured to retain heat within one or more components of the device that may result from any heat generated by the substance 2101 as the substance 2101 is advanced through the device 2100. For example, one or more of the outer sleeve 2102, the inner sleeve 2104, and the distal tip 2106 can optionally be made from materials that have improved or enhanced thermal insulating capabilities which can reduce the amount of heat conducted away from certain portions of the device 2100. In some embodiments, the outer sleeve 2102 and/or the inner sleeve 2104 can optionally be configured to retain heat, while the applicator 2106 is not configured to retain heat.

In some embodiments, one or more of the components of the device 2100 (which can include the outer sleeve 2102 and the inner sleeve 2104, or, optionally, the outer sleeve 2102, the inner sleeve 2104, and the applicator 2106) can be pre-cooled to a desired temperature that is lower than the room temperature or the body temperature such that, if any heat is generated by the substance 2101, the temperature of the device 2100 will not elevate above a desired temperature threshold which, optionally, can be the body temperature of the patient.

Additionally, in some embodiments, one or more of the components of the device 2100 (which can include the outer sleeve 2102 and the inner sleeve 2104, or, optionally, the outer sleeve 2102, the inner sleeve 2104, and the applicator 2106) can be configured to maintain the substance 2101 (which can be a hydrogel) at a temperature that is below a threshold temperature value so that the adhesive properties or capabilities of the substance are reduced when the substance 2101 is contained within the device. Upon advancement of the substance 2101 onto the applicator portion 2110 or application of the substance 2101 on the target tissue or surface, the temperature of the substance and, consequently, the adhesive properties, can increase. For example and without limitation, the outer sleeve 2102 can be sized and configured such that an inner diameter of the passageway 2103 is greater than an outside surface of the inner sleeve 2104 so as to create a space between the inside surface of the outer sleeve 2102 and the outside surface of the inner sleeve 2104. A cooling fluid can be channeled through individual lumen or otherwise through the passageway 2103 to provide a source of cooling to the inner sleeve 2104 and, consequently, the substance 2101. One or more seals can be used to seal an end of the outer sleeve 2102 to the inner sleeve 2104 so that none of the cooling fluid is leaked from the device 2101. Alternatively, an outer shell that is configured to surround the outer sleeve 2102 can be positioned about the entire outer sleeve 2102 to provide an additional cavity or passageway for communication of a cooling fluid that will reduce the temperature within the outer sleeve 2102 and, consequently, of the substance 2101. An inlet port and an outlet port can be formed in or coupled with the handle for the inlet and outlet of cooling fluid through the device 2100. The cooling fluid can optionally include ammonium nitrate.

Optionally, a rheostat and/or other means can be positioned within the handle and can be used to control the temperature of any components of or all of the device 2100. Optionally, one or more thermal sensors or other sensors can be used to monitor the temperature of any components of or all of the device 2100. Additionally, any embodiments of the device 2100 disclosed herein can be configured to have the capability to automatically maintain a temperature of portions of the device within a specified range, even when the substance or application may tend to increase the temperature of the device or components thereof.

Additionally, any embodiments of the device 2100 disclosed herein can be configured to transfer heat to one or more of the components of the device 2100 (which can include the outer sleeve 2102 and the inner sleeve 2104, or, optionally, the outer sleeve 2102, the inner sleeve 2104, and the applicator 2106, or, optionally, just the applicator 2106 or applicator portion 2110) to elevate a temperature of the substance 2101 contained within the device and/or the applicator tip to transfer or deliver heat to the target tissue. In some embodiments, thermally conducting materials such as, without limitation, copper, steel, Nitinol, aluminum, or other alloys, etc., can be integrated into the device and extend lengthwise along the device to transfer heat from a heat source adjacent to a proximal end or handle of the device to the applicator 2106. Optionally, one or more thermoelectric components or means can be used to transfer heat to one or more of the components of the device 2100 (which can include the outer sleeve 2102 and the inner sleeve 2104, or, optionally, the outer sleeve 2102, the inner sleeve 2104, and the applicator 2106, or, optionally, just the applicator 2106 or applicator portion 2110).

In any embodiments disclosed herein, the device or method can include removing or liquefying solidified substance or gel from the device 2100 or tissue surface (such as the tissue on the surface of the eye), if desirable, by increasing or decreasing a temperature of the inner sleeve 2104, applicator 2106 or applicator portion 2110, depending on the specific thermoresponsive properties of the material. The liquefied substance or gel can then be aspirated through the device and removed through the proximal end of the device or handle portion. The device can optionally be configured to have one or more aspiration tubes or channels to aspirate any liquefied substance or gel, or any other substance that is desired to be removed from the device. The tubes can optionally be heated or temperature controlled to ensure that the removed substance remains in a liquid state.

Figure 56:
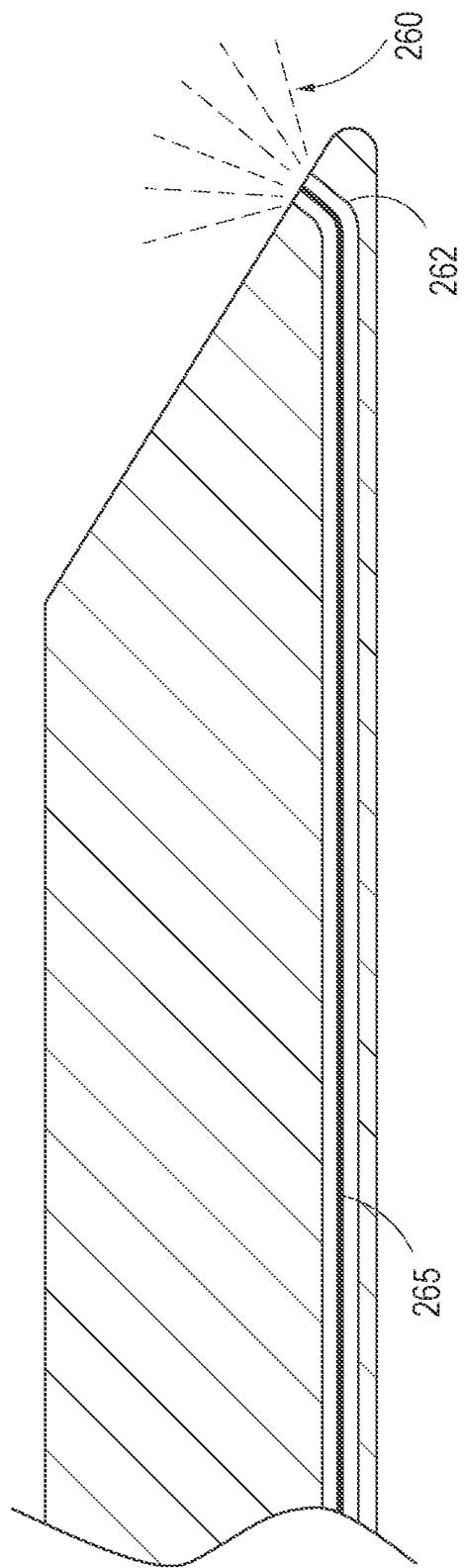
FIG. 56 depicts an example of a cannula with a fiber or wire for light or cautery.

Any embodiments of the devices disclosed herein can include an internal cautery component. Such embodiments can include a cannula with a fiber or wire for light or cautery. FIG. 56 depicts an example of a cannula with a fiber or wire for light or cautery. The example includes a light fiber 265 within a tube along an edge of the cannula. The light fiber 265 includes an angled end 262 in the example, but in some embodiments the end of the light fiber 265 is straight. The end 262 of the light fiber 265 can be beveled at an angle that matches the angle of the bevel of the cannula tip, if so angled. The example includes an illumination 260 emitted by the end 262 of the light fiber 265.

In some embodiments, the cannula tip can be configured to be used for cautery. For example, an extra tube can be included that is configured for passage of an additional material (such as a liquid) that can be expressed from the cannula tip as a spray or as drops. For example, the additional material may be used to activate the bioadhesive material. In some embodiments, the device or system, or a component thereof such as the handle, cannula, cannula tip, light, or light fiber can be configured to emit a light at a wavelength that activates, thickens, or hardens the bioadhesive material.

The system and/or device can be activated in a manner that increases the temperature at the cannula tip (using, for example, the internal cautery component). This is advantageous according to some embodiments in aiding disengagement of the bioadhesive from the applicator portions in instances where the bioadhesive material is a temperature-responsive material that becomes more fluid at higher temperatures. Some embodiments include a cryotherapy component such as a cryotherapy handpiece. In some embodiments, the system or device may be activated in a manner that decreases the temperature at the applicator tip (using, for example, a cryotherapy component). This is advantageous according to some embodiments in aiding disengagement of the bioadhesive from the applicator portion in instances where the bioadhesive material is a temperature-responsive material that becomes more fluid, friable, or releasable at lower temperatures.

The substance used with any of the embodiments disclosed herein can include a thermally activated substance. Additionally, the device can optionally be configured to provide a source of warm air or cold air onto the substance through an additional lumen within the inner cannula 2104, through an additional lumen or passageway outside of the inner cannula 2104, through a completely separate cannula from a separate device, or otherwise. The warm air or cold air can be blown onto the applied substance. The device can optionally include a filter to filter the air before warming or cooling it and applying it to the substance. In any embodiments, the air source passageway can have any of the sizes disclosed herein for the outer cannula 2102 and/or the inner cannula 2104. The source of warm or cold air can be a free-standing piece of equipment, can be integrated into the outer or inner cannula, can be integrated into other surgical devices such as a vitrectomy machine that is configured to filter the air and pass it to the eye or other instruments.

Any embodiments of the devices disclosed herein can be incorporated or included in a kit or a system, also comprising one or more substances (which can be any of the substances disclosed herein or other substances now known or later developed). The kit can also include a material dispenser for dispensing the substance, if not included with the device. The kit can also optionally include a tip plug or protective cover for a distal end of the device, if not already included with the device. The system, device, or kit can be sterile or pre-sterilized. In some embodiments, the kit includes a pre-sterilized material dispenser as described herein.

The kit or system can also include any of the other components or devices disclosed herein, including, for example and without limitation, one or more of the curing components and devices for applying the curing components to the substance after the substance has been applied to the target tissue surface. Additionally, in any embodiments disclosed herein, the substance or one or more different substances may be provided in a capsule or a self-contained syringe that can be coupled with an opening, port, or otherwise in the handle portion of the device.

Some embodiments relate to a use of a system, device or kit for applying a substance (which can comprise any of the substances listed above, including a bioadhesive) to an eye or retina such as for repair of the eye including the retina, sclera, conjunctiva, and cornea, etc. In any such methods, the cannula can optionally be advanced into the eye using any known or commonly used techniques. The surgical procedures disclosed herein can include piercing the surface of the eye or other tissue of the eye, or can include treating the eye tissue without entering or piercing any eye tissue.

The methods disclosed herein can include advancing the substance to the applicator portion of the applicator tip and from the applicator portion to the target tissue, which can be eye tissue or, optionally, retinal tissue. Any embodiments disclosed herein can optionally be used to repair a retinal tear or other defects or tissues within the body, as disclosed elsewhere herein and other surgical applications beyond what is disclosed herein. Some embodiments include operation of a button on the handpiece of the device or system, other manual controls, or operation of a foot pedal to, for example, control a valve to control aspiration of the substance, infusion of the substance, infusion or delivery of an activation solution or other curing means, allow the substance to flow through the passageway of the handpiece and/or through the flow passageway(s) of the devices, etc.

Any embodiments disclosed herein can include a means for curing the substance after it has been applied to the target surface, including light emitting equipment, UV emitting equipment, application of increased temperature (e.g., applying heat), application of reduced temperature (e.g., applying cooling), or otherwise.

Any embodiments disclosed herein can also be configured for applications outside of the eye tissue, including without limitation for applications in gastrointestinal tissue, colon tissue, etc.

In some embodiments, the material delivered by the device can be delivered transvitreally. For transvitreal use, delivery through the device may employ a cutting action to remove the cohesive/sticky material once it is delivered. In some embodiments, excess is be removable with a vitrectomy cutter and/or aspiration. Transvitreal delivery may be utilized in air filled eye to avoid adhesive material floating to non-targeted ocular structures such as lens/IOL/pars plicata/angle, corneal endothelium which could result in obscuration of view through lens/IOL or impairment of inflow/outflow of aqueous humor.

During application of the substance, one or more portions of the tissue can be covered with a fluid to protect such tissues or mask such tissue to avoid contact from the substance. Additionally, air can be used to control an application of the substance and/or avoid contact of some tissue surfaces by the substance. For example and without limitation, an air disc can be created to cover or protect a tissue surface, wherein the adhesive material can settle on a fluid surface rather than on underlying structures, and/or be immediately activated (made non-sticky) to avoid adhesion to non-target tissues. Activation in any embodiments disclosed herein can include activation by water or similar liquid. If the substance is thermoreactive, any undesirable material can have its temperature modulated by any embodiments of this device so the material can be converted to liquid form, after which such material can be aspirated from the eye.

Trans-scleral delivery is contemplated, and may include delivery of material to the retinal break through the subretinal space. After the material sticks to the retina after being delivered via a tapered end of the device, or needle, the material may be amputated as the needle is withdrawn from the sclera. The material may act as a buffer to prevent retinal incarceration into sclera defect left by the cannula, needle, or device utilized to cross the scleral and choroidal tissue.

The delivery device may be single, double, or triple bored. In some embodiments, the double bore device includes one bore for delivery of a material and a second bore for reflux of intraocular fluid to outside the eye as TOP increases. In some embodiments, one of the bores contains a light fiber that may be used for illumination. In some embodiments, one of the bores contains a fiber that delivers a laser light. In some embodiments, one of the bores contains a fiber that delivers heat or some other source of energy used for curing the injected material.

In some embodiments, the triple bore device includes one bore for delivery of a material, one bore for passage of gas used to create bubble or film of adhesive material, and a third bore for reflux of intraocular fluid to outside the eye as IOP increases.

Figure 59:
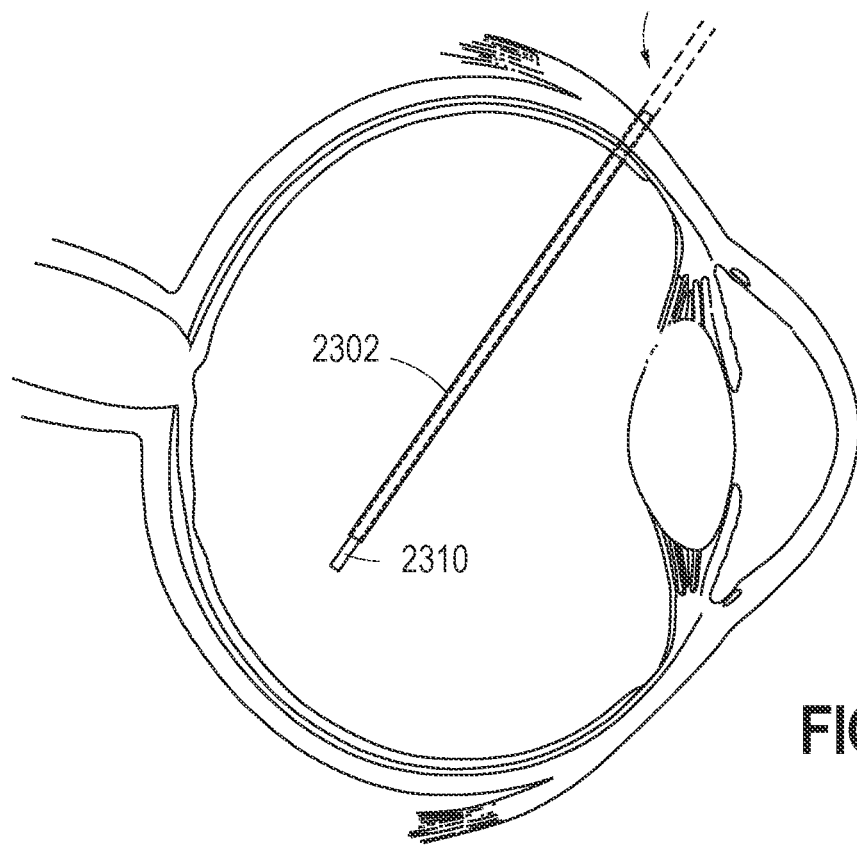
FIG. 59 is a side view of an embodiment of a device for application of a substance to a surface that has been surgically advanced into an eye, showing the applicator portion in a retracted state.
Figure 60:
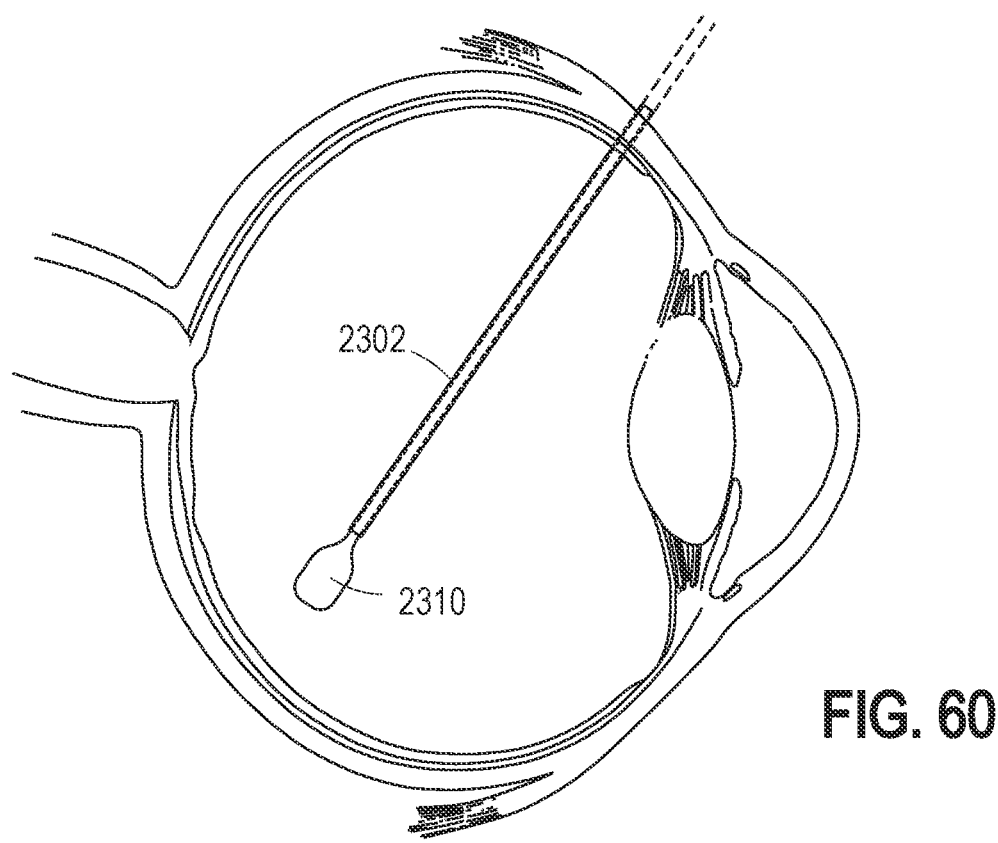
FIG. 60 is a side view of the device show in FIG. 59 that has been surgically advanced into an eye, showing the applicator portion in an extended, expanded state.
Figure 61:
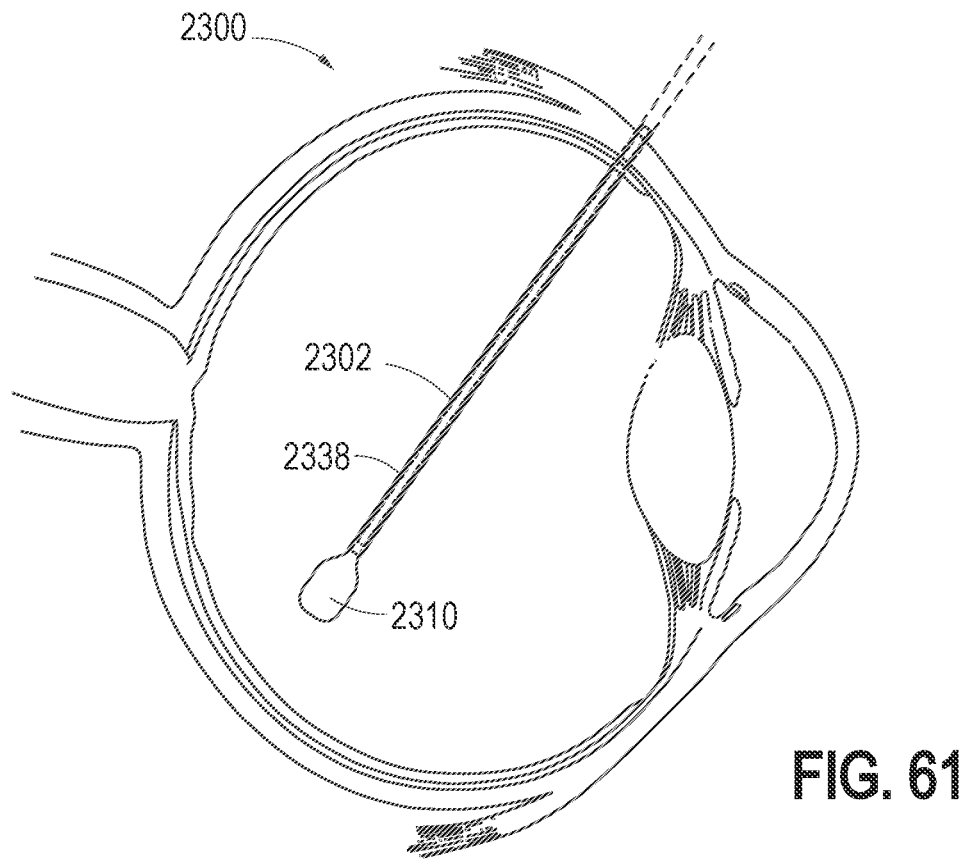
FIG. 61 is a side view of another embodiment of a device for application of a substance to a surface that has been surgically advanced into an eye, showing a supply cannula in a retracted state within the outer cannula.
Figure 62:
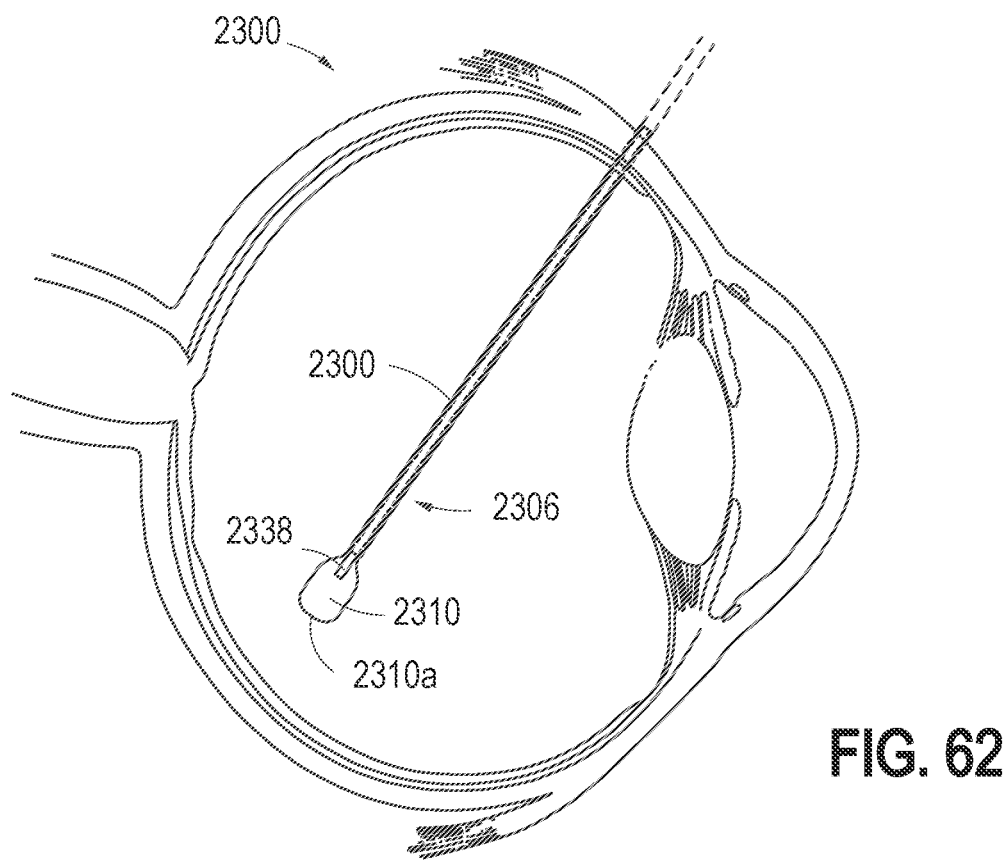
FIG. 62 is a side view of the embodiment of a device show in FIG. 61, showing the supply cannula in an extended state so as to overlap a portion of the applicator portion.
Figure 63:
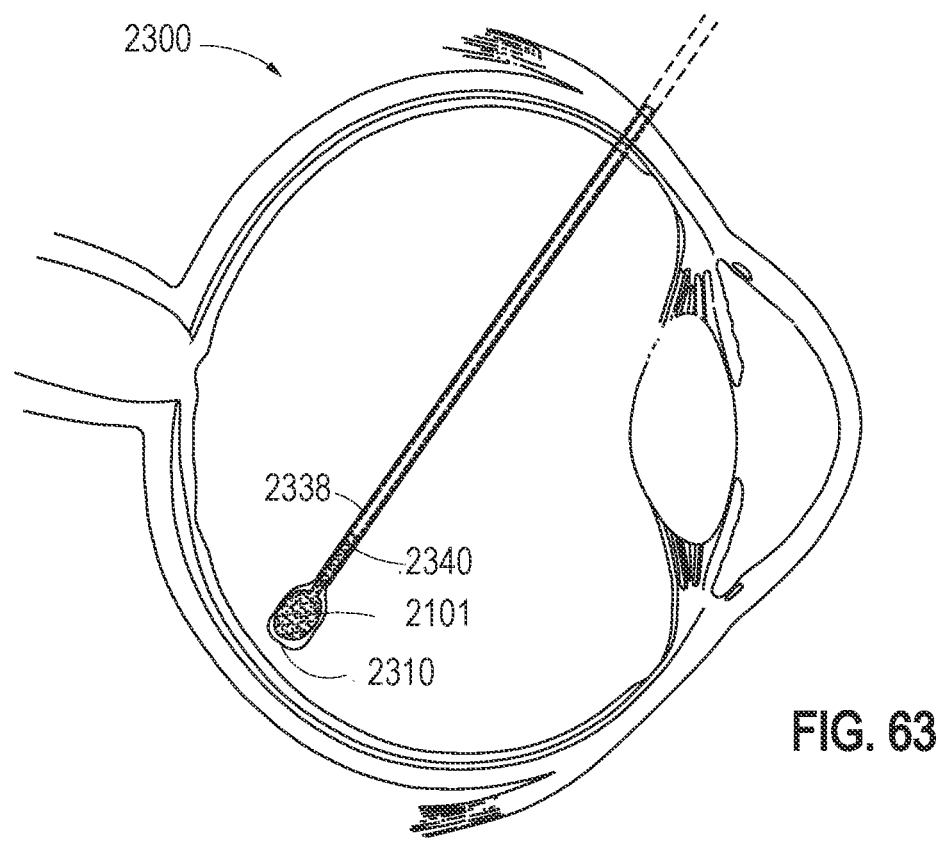
FIG. 63 is a side view of the embodiment of a device show in FIG. 61, showing the applicator portion at least partially covered with a substance.
Figure 64:
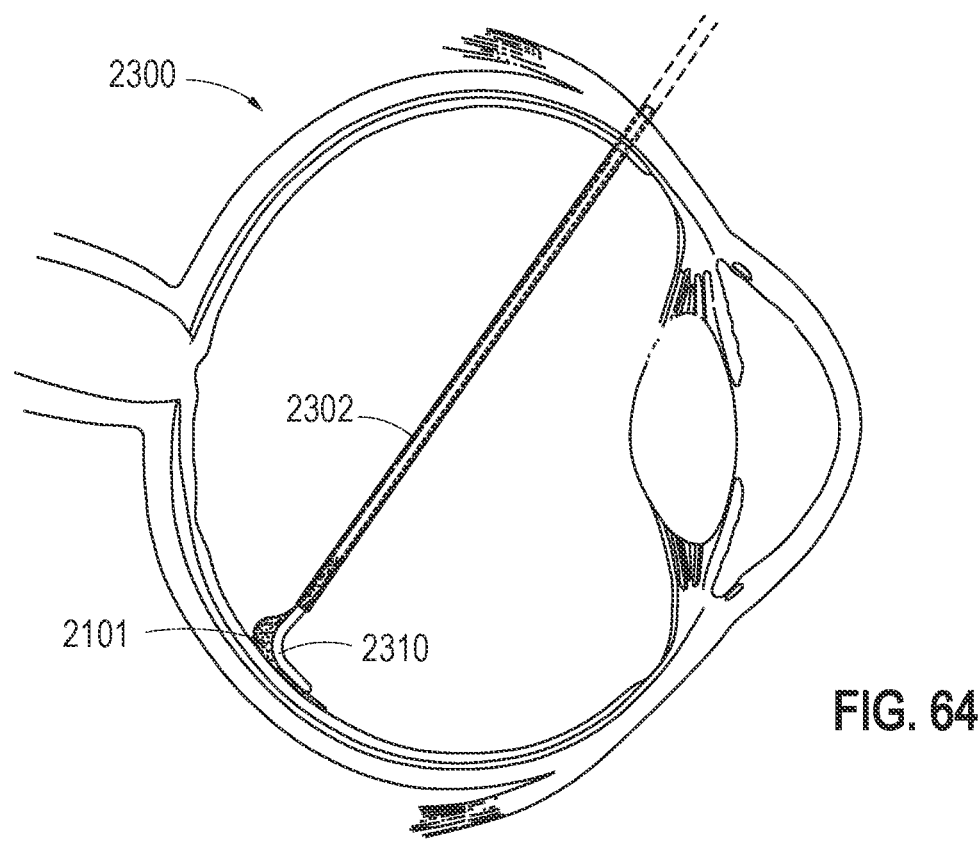
FIG. 64 is a side view of the embodiment of a device show in FIG. 61, showing the applicator portion transferring the substance to a tissue defect in the eye.

FIGS. 59-64 illustrate one optional method of using the embodiment of the device 2300. With reference to FIG. 59, a cannula 2302 can be advanced into the eye. An applicator portion 2310 can be positioned within or withdrawn within the cannula 2302 as the cannula is advanced into the eye, as shown in FIG. 59. In some embodiments, the applicator portion 2310 can have a substance on the applicator portion 2310 when the applicator portion is positioned within the cannula 2302. In some embodiments, as discussed below, the substance can be applied to the applicator portion 2310 after the applicator portion 2310 is advanced distally past a distal end of the cannula 2302. Thereafter, as shown in FIG. 60, the applicator portion 2310 can be extended from the distal end of the cannula 2302 and permitted to expand to the second or expanded state. The cannula 2338 (also referred to herein as a supply cannula) can be extended through the outer cannula 2302. FIG. 61 shows the cannula 2338 extended so that a distal end of the cannula 2338 is approximately aligned with a distal end of the outer cannula 2302. The cannula 2338 can be extended past the distal end of the outer cannula 2302 toward a distal end 2310a of the applicator portion 2310 of the applicator tip, as shown in FIG. 62. Thereafter, as shown in FIG. 63, a substance 2101 can be advanced through the passageway 2340 of the cannula 2338 and ejected onto the applicator portion 2101. Thereafter, the outer cannula 2302 and the applicator portion 2310 can be moved and manipulated by the user to apply the substance 2101 to the target tissue, as shown in FIG. 64.

Some embodiments of the system and/or device further include an internal material supply chamber within the handpiece or cannula, for cooling or heating fluids, or other fluids or gases that can be used with the device 2100. The internal material supply chamber can optionally include an elongate body comprising a proximal end and a distal end comprising a material supply tip and/or exit port. The internal material supply chamber can optionally be internal to or adjacent to at least a portion of the passageway 2105.

In some embodiments of the system and/or device, the internal material supply chamber, elongate body of the internal material supply chamber, material supply tip and/or material supply exit port comprises a 0.1-0.5 mm, 0.5-1 mm, 1-2 mm, 2-3 mm, 3-4 mm, 4-5 mm, 5-6 mm, 6-7 mm, 7-8 mm, 8-9 mm, 9-10 mm, 10-20 mm, 20-30 mm, 30-40 mm or 40-50 mm cross-sectional diameter. In some embodiments of the system or device, the internal material supply chamber, elongate body of the internal material supply chamber, material supply tip and/or material supply exit port comprises a length of 0.1-0.5 mm, 0.5-1 mm, 1-2 mm, 2-3 mm, 3-4 mm, 4-5 mm, 5-6 mm, 6-7 mm, 7-8 mm, 8-9 mm, 9-10 mm, 10-20 mm, 20-30 mm, 30-40 mm, 40-50 mm, 50-60 mm, 60-70 mm, 70-80 mm, 80-90 mm, 90-100 mm, 100-150 mm or 150-200 mm.

Some embodiments of the system and/or device further comprise a second internal material supply chamber. In some embodiments of the system or device, the internal material supply chamber and the second internal material supply chamber each comprises a separate bioadhesive material, for example a polyethylene glycol solution and a trilysine amine solution, hydrogel, double layer hydrogel, or polymeric hydrogel.

Figure 67A:
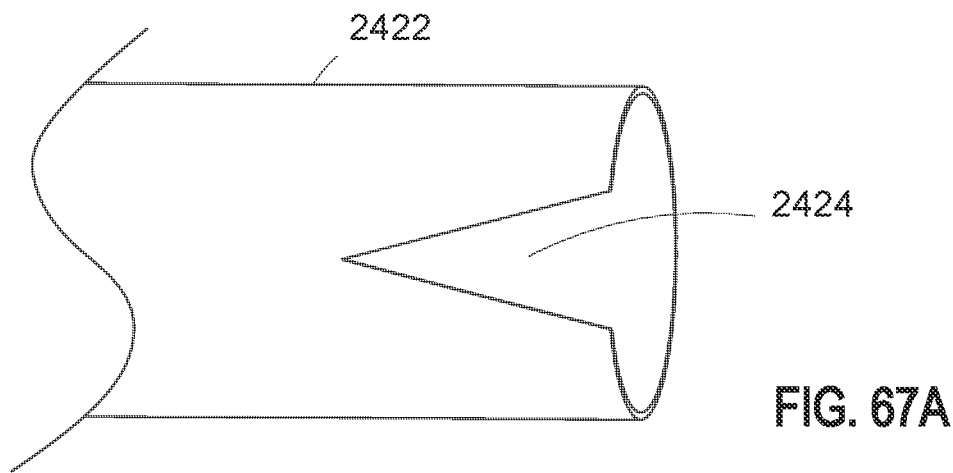
FIG. 67A is a top view of an end portion of another embodiment of a cannula that can be used with any embodiments of the devices disclosed herein.
Figure 67B:
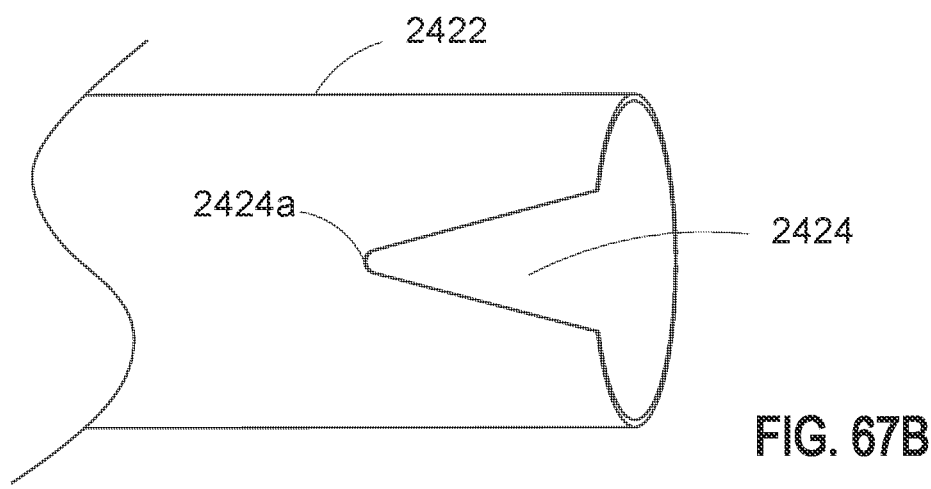
FIG. 67B is a top view of an end portion of another embodiment of a cannula that can be used with any embodiments of the devices disclosed herein.
Figure 67C:
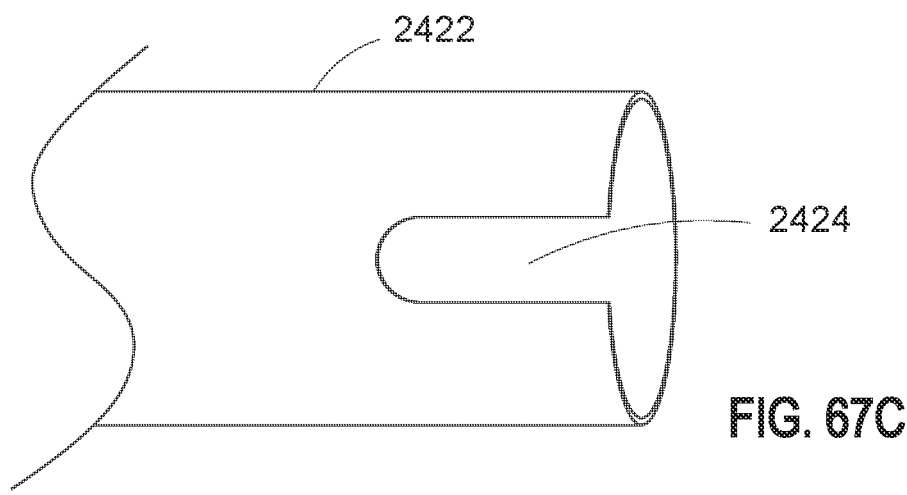
FIG. 67C is a top view of an end portion of another embodiment of a cannula that can be used with any embodiments of the devices disclosed herein.

FIG. 65A is a perspective view of an end portion of an embodiment of a cannula 2402 that can be used with any embodiments of the devices disclosed herein. FIG. 65B is a section view of the embodiment of the cannula 2402 shown in FIG. 65A, taken through line 65B-65B of FIG. 65A. FIG. 65C is a top view of the embodiment of the cannula 2402 shown in FIG. 65A. As shown, the cannula 2402 can have a notch or cutout 2404 formed in an end portion of the cannula 2402 which can assist in the retraction or reduction in size (e.g., the constriction or collapse) of any of the applicator portion embodiments disclosed herein as the applicator portion is retracted into the distal end of the outer sleeve or cannula. With reference to FIG. 65C, in some embodiments, the cutout 2404 can have an asymmetric shape about a plane extending through an axial centerline C of the cannula 2402—for example and without limitation, through an plane that is through the axial centerline C and is perpendicular to the plane of the figure (e.g., perpendicular to the plane of the paper). In some embodiments, the notch 2404 can terminate in a curved end portion 2406. In other embodiments, the notch 2404 can have a triangular shape wherein one side of the notch is parallel to the axial centerline of the cannula. In other embodiments, the notch can have a triangular shape wherein both sides of the notch are tapered or angled or are otherwise in a "v" shape, such as in the notch 2424 of the cannula 2422 shown in FIGS. 67A and 67B. In some embodiments, as shown in FIG. 67B, the apex or proximal end portion 2424a of the v shaped notch can be rounded or have a radius. In other embodiments, the notch can have a rounded end portion and parallel side portions, or otherwise have a generally "u" shape, as in FIG. 67C.

Additionally, with reference to FIG. 65C, the notch in any embodiments disclosed herein (including without limitation the notches 2404, 2414, and 2424) can have a length L and a width W adjacent to the end of the cannula 2402, and the embodiments of the cannulas disclosed herein can have a diameter D. For example and without limitation, the width W of the notch (or width W1 for the notch 2414) can be 30% (or approximately 30%) of the diameter D of the cannula, or from 20% (or approximately 20%, or less than 20%) to 100% (or approximately 100%, or more than 100%) of the diameter D of the cannula, or from 30% (or from approximately 30%) to 50% (or approximately 50%) of the diameter D of the cannula, or of any value or from and to any values within these ranges. In some embodiments, the width W of the notch (or width W1 for the notch 2414) can be 0.25 mm (or approximately 0.25 mm), or from 0.1 mm (or, in some embodiments, approximately 0.1 mm or less than 0.1 mm) to 1.5 mm (or, in some embodiments, approximately 1.5 mm or more than 1.5 mm), or from 0.25 mm (or, in some embodiments, approximately 0.25 mm) to 0.75 mm (or, in some embodiments, approximately 0.75 mm), or of any value or from and to any values within these ranges.

In any embodiments, the length L of the notch of any embodiments disclosed herein can be approximately 30% of a length of the applicator portion, or from 20% (or approximately 20% or less than 20%) to 100% (or approximately 100% or more than 100%) of the length of the applicator portion, or from 30% (or approximately 30%) to 60% (or approximately 60%) of the length of the applicator portion, or from 30% (or approximately 30%) to 50% (or approximately 50%) of the length of the applicator portion, or of any value or from and to any values within these ranges. In some embodiments, the length of the notch can be approximately 1 mm, or from 0.5 mm (or, in some embodiments, approximately 0.5 mm or less than 0.5 mm) to 2 mm (or, in some embodiments, approximately 2 mm or more than 2 mm), or from 0.75 mm (or, in some embodiments, approximately 0.75 mm) to 1 mm (or, in some embodiments, approximately 1 mm), or of any value or from and to any values within these ranges.

FIGS. 66A and 66C are a perspective view and a top view of an end portion of another embodiment of a cannula 2412 that can be used with any embodiments of the devices disclosed herein. FIG. 66B is a section view of the embodiment of the cannula 2412 shown in FIG. 66A, taken through line 66B-66B of FIG. 66A. As shown, the cannula 2412 can have a notch or cutout 2414 formed in an end portion of the cannula 2412 which can assist in the deployment and/or retraction or collapse of any of the applicator portion embodiments disclosed herein. With reference to FIG. 65C, in some embodiments, the cutout 2414 can have an asymmetric shape about a plane extending through an axial centerline C of the cannula 2412—for example and without limitation, through an plane that is through the axial centerline C and is perpendicular to the plane of the figure (e.g., perpendicular to the plane of the paper).

Additionally, in any embodiments, the notch 2414 can be a double notch having a first portion 2414a and a second portion 2414b that is narrower than the first portion 2414a. For example and without limitation, the first portion 2414a can have a width W1 that can be approximately double the width W2 of the second portion 2414b, or can be from 50% greater (or approximately 50% greater) to 100% greater (or approximately 100% greater) than the width W2 of the second portion 414b. In any embodiments, the first portion 2414a of the notch 2414 can have a length L1 that is 50% (or approximately 50%) of the overall length L of the notch 2414, or a length L1 that is from 30% (or approximately 30% or less than 30%) to 80% (or approximately 80% or less than 80%) of the overall length L of the notch 2414, or a length L1 that is from 40% (or approximately 40%) to 60% (or approximately 60% or less than 60%) of the overall length L of the notch 2414. In some embodiments, the notch 2414 can terminate in a curved end portion 2416.

Figure 68:
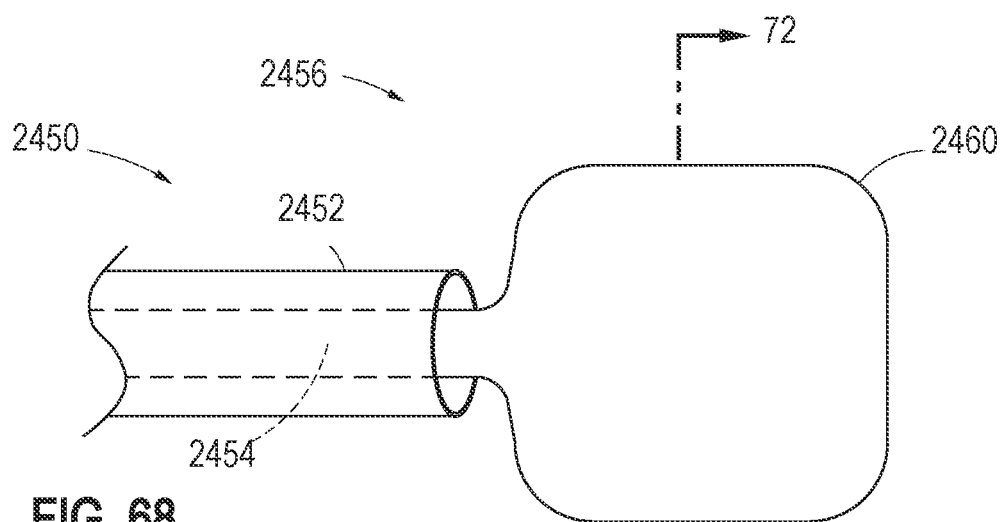
FIG. 68 is a top view of an embodiment of an applicator that can be used with any device embodiments disclosed herein.

FIG. 68 is a top view of another embodiment of a device 2450 having an applicator 2456 that can be used with any device embodiments disclosed herein. The device 2450 and/or applicator 2456 can include any of the components, features, materials, and/or other details of any of the other device or applicator embodiments disclosed herein, including without limitation device 2100 and/or applicator 2106 described above, in combination with or in place of any of the features described below to form new embodiments. With reference to FIG. 68, the applicator 2456 can have an applicator portion 2460 that is coupled with a core member or elongate body 2454 that extends through at least part (or all) of the device 2450.

Figure 72:
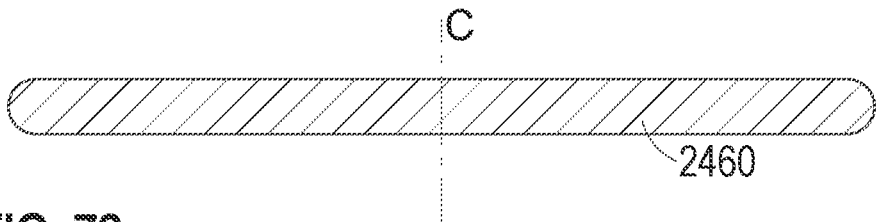
FIG. 72 is a section view of an embodiment of an applicator portion that can be used with any device embodiments disclosed herein, taken through line 72-72 of FIG. 68 so that the section view is perpendicular to the axial centerline of the applicator.

With reference to FIG. 72, which is a section view of the embodiment of the applicator portion 2460 that can be used with any device embodiments disclosed herein, taken through line 72-72 of FIG. 68 so that the section view is perpendicular to the axial centerline of the applicator 2456. As shown, some embodiments of the applicator portion 2460 can have a symmetrical shape about center plane C and can have a generally uniform thickness about the entire width of the applicator portion 2460.

Figure 73:
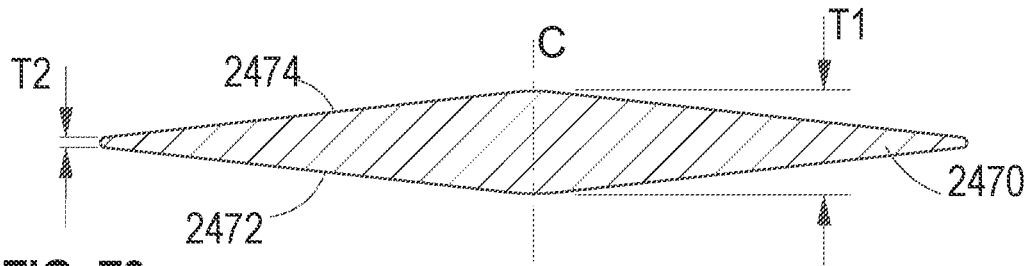
FIG. 73 is a section view of another embodiment of an applicator portion that can be used with any device embodiments disclosed herein, wherein the section view is perpendicular to the axial centerline of applicator.
Figure 74:
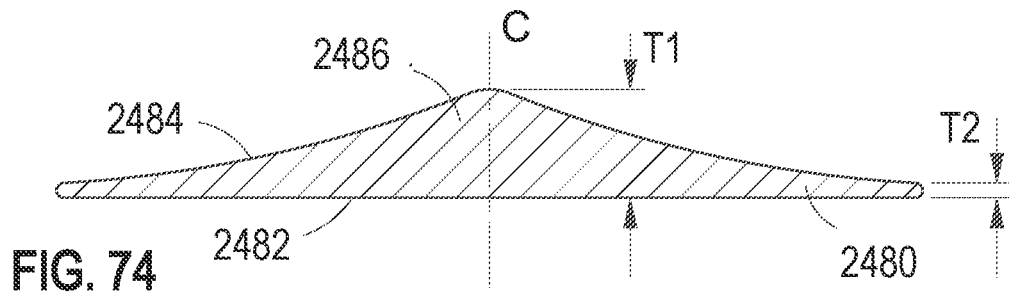
FIG. 74 is a section view of another embodiment of an applicator portion that can be used with any device embodiments disclosed herein, wherein the section view is perpendicular to the axial centerline of applicator.
Figure 75:
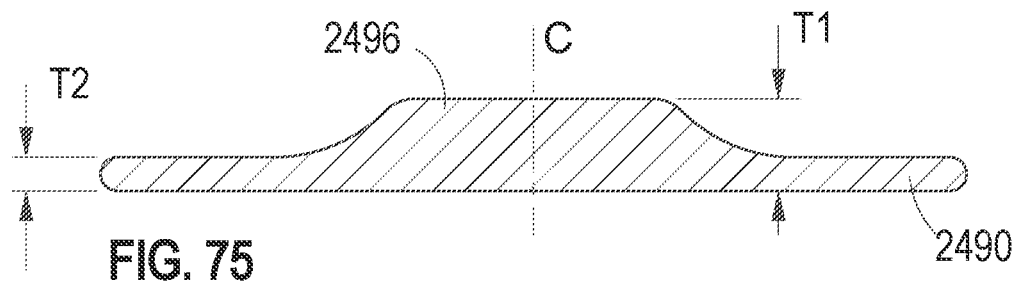
FIG. 75 is a section view of another embodiment of an applicator portion that can be used with any device embodiments disclosed herein, wherein the section view is perpendicular to the axial centerline of applicator.

FIG. 73 is a section view of another embodiment of an applicator portion 2470 that can be used with any device embodiments disclosed herein, wherein the section view is perpendicular to the axial centerline of applicator. As shown, some embodiments of the applicator portion 2470 can have a symmetrical shape about center plane C and can have a tapering thickness wherein the applicator portion 2470 tapers from a first thickness T1 in a middle portion of the applicator portion 2470 to a second, lesser thickness T2 at one or both of the lateral sides of the applicator portion 2470. In some embodiments, as shown in FIG. 73, a bottom surface 2472 and/or a top surface 2474 of the applicator portion 2470 can be angled from the center portion of the applicator portion 2470 toward the lateral edges of the applicator portion 2470. In other embodiments, as shown in FIGS. 74 and 75, the bottom surface 2472 and/or the top surface 2474 of the applicator portion 2470 can be generally planar from the center portion of the applicator portion 2470 toward the lateral edges of the applicator portion 2470.

In any embodiments disclosed herein, a bottom surface and/or a top surface of the applicator portion can be concave or curved from the center portion of the applicator portion 2470 toward the lateral edges of the applicator portion 2470. For example and without limitation, as shown in FIG. 74, a top surface 2484 of the applicator portion 2480 can be curved from the center portion of the applicator portion 2470 toward the lateral edges of the applicator portion. In any embodiments disclosed herein, the center portion, having an increased thickness (such as thickness T1), can be narrow, as with center portion 2486 of the embodiment of the applicator portion 2480 shown in FIG. 74, or can be wider, as with center portion 2496 of the embodiment of the applicator portion 2490 shown in FIG. 75 or the center portion 2664 of the embodiment of the applicator portion 2650 shown in FIG. 71. For example and without limitation, the center portion can have a width that is 30% (or approximately 30%) of the width of the entire applicator portion, or from 10% (or approximately 10% or less than 10%) to 60% (or approximately 60% or more than 60%), or from 20% (or approximately 20%) to 40% (or approximately 40%) of the width of the entire applicator portion.

In some embodiments, the first thickness T1 can be 0.2 mm (or approximately 0.2 mm), or from 0.1 mm (or approximately 0.1 mm or less than 0.1 mm) to approximately 1 mm (or approximately 1 mm or greater than 1 mm), or from 0.15 mm (or approximately 0.15 mm) to approximately 0.5 mm (or approximately 0.5 mm), or of any value or from and to any values within these ranges. In any embodiments, the second thickness T2 can be 0.1 mm (or approximately 0.1 mm), or from 0.05 mm (or approximately 0.05 mm or less than 0.05 mm) to approximately 0.5 mm (or approximately 0.5 mm or greater than 0.5 mm), or from 0.075 mm (or approximately 0.075 mm) to approximately 0.25 mm (or approximately 0.25 mm), or of any value or from and to any values within these ranges.

In some embodiments, the first thickness T1 can be 50% (or approximately 50%), or from 10% (or approximately 10% or less than 10%) to approximately 80% (or approximately 80% or greater than 80%), or from 20% (or approximately 20%) to approximately 60% (or approximately 60%), or from 30% (or approximately 30%) to approximately 40% (or approximately 40%), or of any value or from and to any values within these ranges.

Figure 76:
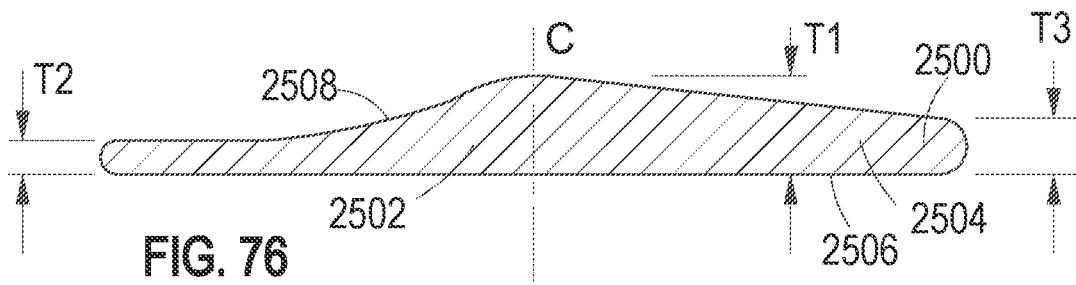
FIG. 76 is a section view of another embodiment of an applicator portion that can be used with any device embodiments disclosed herein, wherein the section view is perpendicular to the axial centerline of applicator.

Further, in any embodiments disclosed herein, the applicator portion 2470 can have an asymmetrical cross section such that a first side of the applicator portion 2470 has a different shape and/or thickness as compared to a shape and/or thickness of a second side portion 2470, wherein the first and second side portions can be defined as being divided by the centerline axis C. For example, as shown in FIG. 76, which is a section view of another embodiment of an applicator portion 2500 that can be used with any device embodiments disclosed herein, a first side portion 2502 can have a first shape and thickness profile that is different than a second shape and thickness profile of a second side portion 2504 of the applicator portion 2500. The thickness T1 at a center portion can be greater than a thickness T2 at a lateral edge or side portion of the first side portion 2502, and a thickness T3 at a lateral edge or side portion of the second side portion 2504 can be greater than the thickness T2 at the lateral edge or side portion of the first side portion 2502. Additionally, in any embodiments disclosed herein, the shape of the bottom surface 2506 can be different than the shape of the top surface 2508, and the shape of the bottom surface 2506 on the first side portion 2502 can be the same or different than the shape of the bottom surface 2506 on the second side portion 2504, and/or the shape of the top surface 2508 on the first side portion 2502 can be the same or different than the shape of the top surface 2508 on the second side portion 2504.

Figure 69:
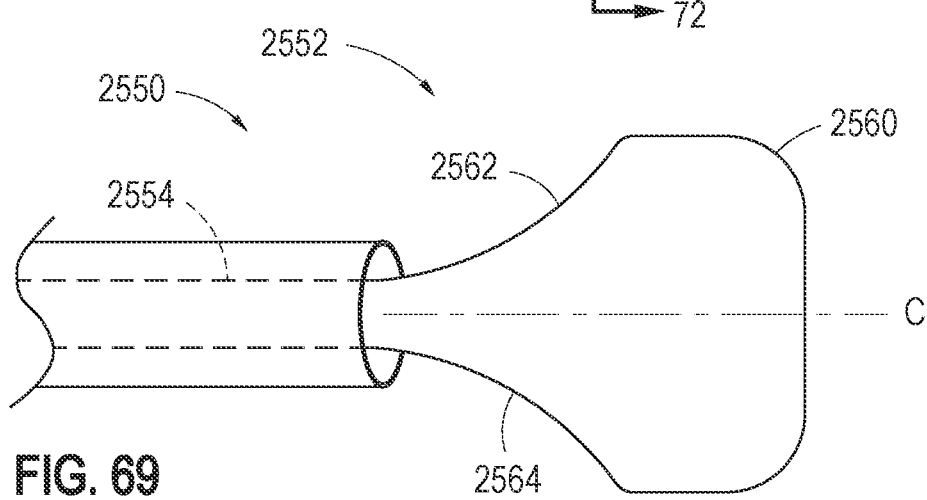
FIG. 69 is a top view of another embodiment of an applicator that can be used with any device embodiments disclosed herein.
Figure 70:
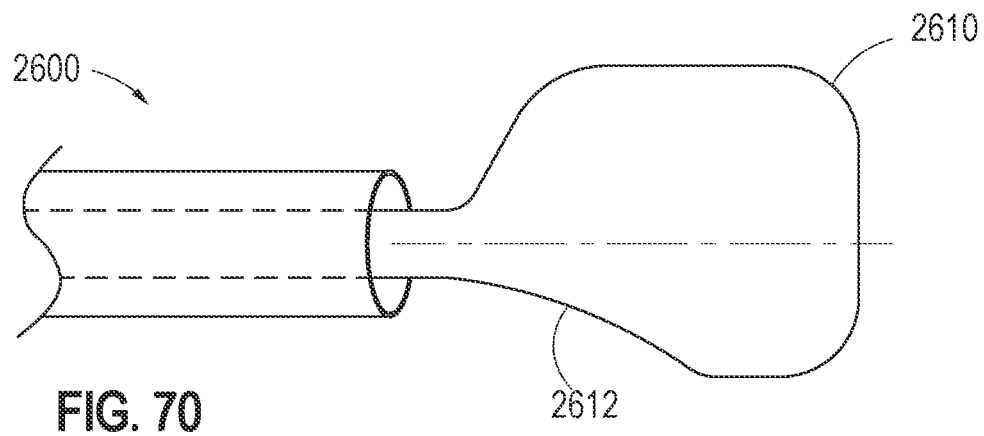
FIG. 70 is a top view of another embodiment of an applicator that can be used with any device embodiments disclosed herein.

FIG. 69 is a top view of another embodiment of a device 2550 having an applicator 2552 that can be used with any device embodiments disclosed herein. The device 2550 and/or applicator 2556 can include any of the components, features, materials, and/or other details of any of the other device or applicator embodiments disclosed herein, including without limitation devices 2100, 2450 and/or applicators 2106, 2456 described above, in combination with or in place of any of the features described below to form new embodiments. With reference to FIG. 69, the applicator 2552 can have an applicator portion 2560 that is coupled with a core member or elongate body 2554 that extends through at least part (or all) of the device 2550. With reference to FIG. 69, the applicator portion 2560 can have a first tapering transition portion 2562 and a second tapering transition portion 2564. The first and second tapering transition portions can assist in collapsing, folding, rolling, furling, or otherwise contracting the applicator portion upon retraction of the applicator portion into the cannula. In some embodiments, the first and second tapering transition portions 2562, 2564 can be symmetrical about the centerline C of the applicator portion 2460. In other embodiments, the applicator portion can have tapering transition portions on both sides of the applicator portion, but which are sized and/or shaped differently, such as with the first and second tapering transition portions 2656, 2658 of the embodiment of the applicator portion 2650 shown in FIG. 71. For example and without limitation, a first tapering transition portion can be longer than a second tapering transition portion. In other embodiments, the applicator portion can have just one tapering transition portion, such as with the applicator portion 2610 of the embodiment of the device 2600 illustrated in FIG. 70.

Figure 71:
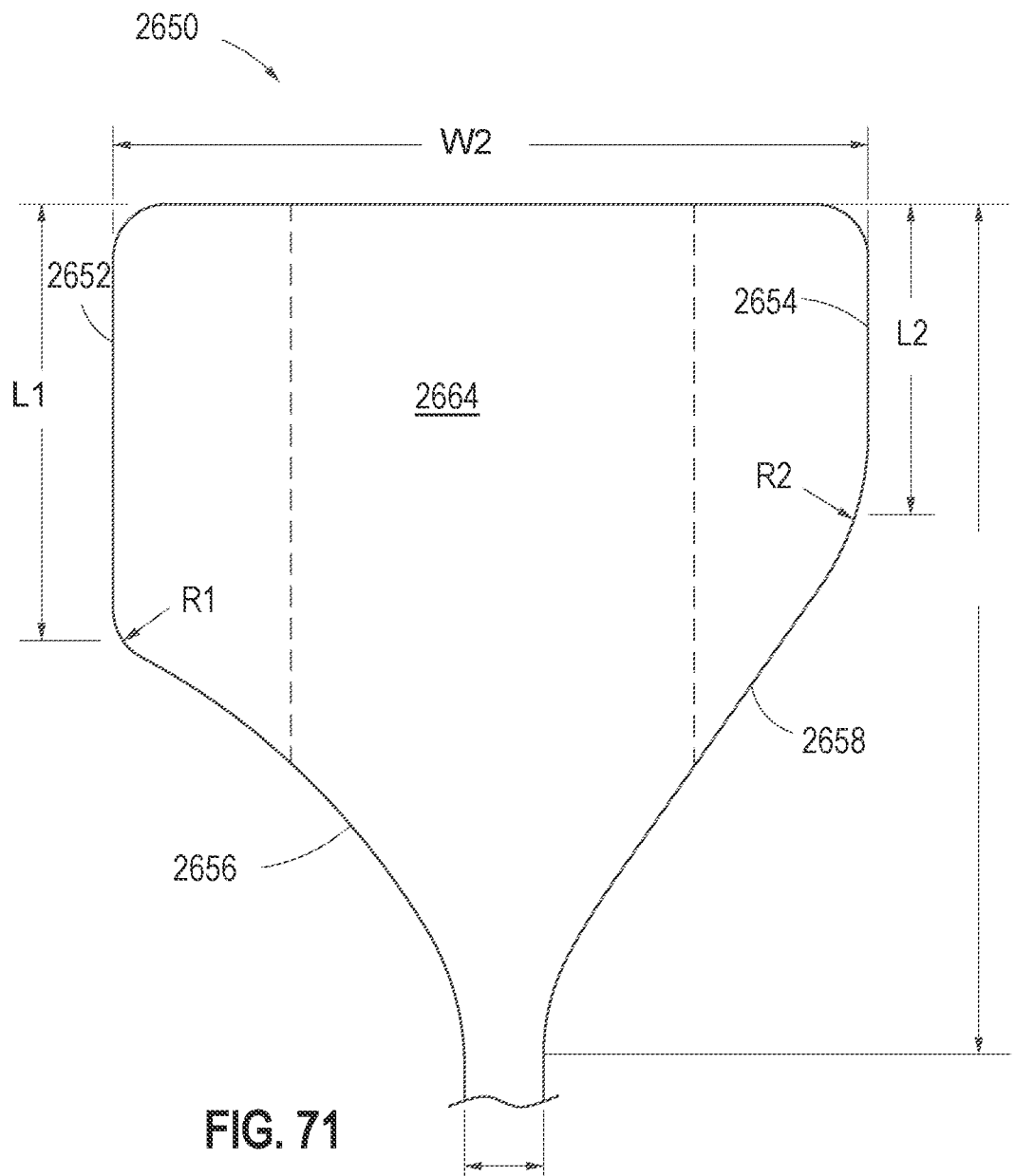
FIG. 71 is a top view of another embodiment of an applicator that can be used with any device embodiments disclosed herein.

With reference to FIG. 71, in any embodiments, the applicator portion (such as applicator portion 2650) can be configured such that a length L1 of a first side wall portion (such as side wall portion 2652, which is also referred to herein as a first side portion) can be shorter than an overall length L of the applicator portion due to the presences of a first tapering transition portion (such as first tapering transition portion 2656). For example, the length L1 of the first side wall portion can be approximately 40% of the overall length L of the applicator portion, or from or from approximately 30% to approximately 50% of the overall length of the applicator portion.

Further, a length L2 of the second side wall (such as side wall portion 2654, which is also referred to herein as a second side portion) can be shorter than the length L1 of the first side wall. This can be due to a different length, angle, and/or other shape of the second tapering side wall portion (such as second tapering side wall portion 2658) and/or a larger radius at the intersection of the second wall portion and the second tapering side wall portion. The radius at the intersection of the second wall portion and the second tapering side wall portion (such as radius R2 in FIG. 71) can be significantly greater (for example, from 2 to 20 times or more greater, or from 5 to 10 times greater, or any values or ranges of values within the foregoing ranges) than a radius at the intersection of the first wall portion and the first tapering side wall portion (such as radius R1 in FIG. 71). In any embodiments, the second side transition portion 2658 can be more gradual than the first side transition portion 2656, to facilitate the collapse or contraction of the applicator portion.

In some embodiments, the first side portion 2652 can have a first transition portion that has a first length in the axial direction and the second side portion 2654 can have a second transition portion that has a second length in the axial direction that is greater than the first length of the first transition portion. In some embodiments, the shorter length of the first transition portion can cause the first side portion 2652 of the applicator tip 2650 to collapse when the applicator portion 2650 is withdrawn into the outer sleeve of the device before the second side portion 2654 of the applicator portion 2650 collapses. This can, in some embodiments, allow the applicator portion 2650 to collapse to a more compact size compared with a symmetrical applicator portion.

FIG. 77 is a perspective view of an end portion of another embodiment of a delivery device 2700, showing an applicator 2702 that is coupled with an inner cannula 2704 in a retracted and collapsed state within the outer cannula body or sleeve 2706 and a substance delivery cannula 2710 in a retracted state within the outer cannula body 2706. FIG. 78 is a perspective view of the end portion of the embodiment of a delivery device 2700 shown in FIG. 77, showing the applicator 2702 in a partially advanced position and expanded state. FIG. 78 also shows that the delivery cannula 2710 is, in some embodiments, axially extendable so as to extend to a distal end portion of the applicator portion 2702 and retractable while the substance is being exuded from the substance delivery cannula 2710. The device 2700 can be configured to limit a range of extension of the substance delivery cannula 2710 so that the substance delivery cannula does not extend beyond a distal end of the applicator portion 2702. The device 2700 can also be configured so that the substance delivery cannula 2710 is in a fixed position at or near the end of the sleeve 2706, allowing delivery of substance onto applicator 2702 surface as applicator 2702 is advanced beyond an end of outer cannula or sleeve 2706. In some embodiments, the only movable or extendable component of the device or a distal end portion of the device can be the applicator and applicator portion, which can be integrally connected.

Figure 79:
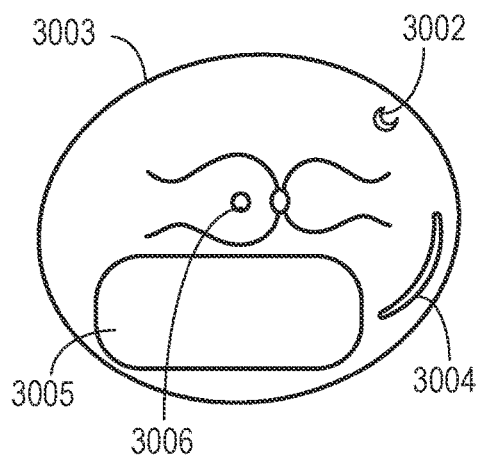
FIG. 79 is an illustration of the eye with various shaped retinal defects.

Retinal breaks, i.e., discontinuities, defects, holes and tears, present in a variety of shapes and sizes. Referring to FIG. 79, the breaks can present, for example, as crescent shaped 3002, oblong 3004, or circular 3006. The breaks can range in size from about 1 mm or smaller to half the area of the retina 3003 or larger, for example, an oblong shaped break 3005 takes up about one-third of the area of the retina 3003.

Figure 80A:
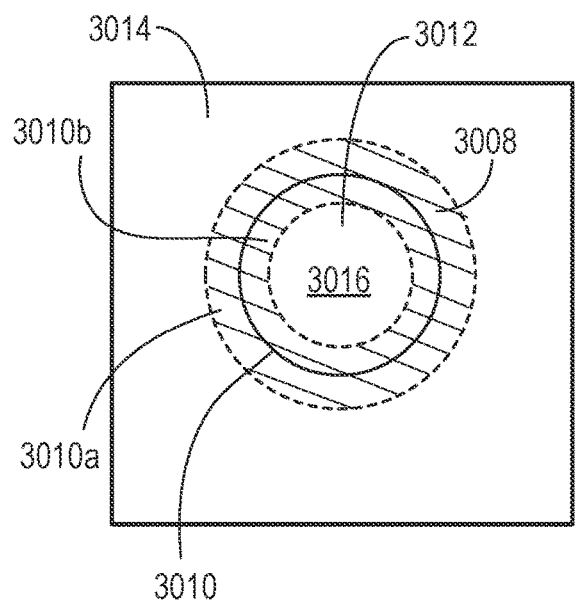
FIG. 80A is an illustration of a retinal defect repair.

As illustrated in FIG. 80A, to adhere the retina to the adjacent exposed cells, a bioadhesive 3008 can be applied to the border 3010 of the defect/retinal junction of a circular retinal defect 3012 (or other shaped defect) so that the bioadhesive 3008 covers the margins 3010a, 3010b of the border 3010 overlapping intact retinal tissue 3014 in the margin 3010a adjacent the border 3010, and some, but not all, of the tissue 3016 that remains within the base of the retinal defect 3012, e.g., tissue 3016 in the margin 3010b that is adjacent the border 3010. This remaining tissue 3016 left behind by the retinal defect may be any number of layers of retinal tissue, including but not limited to retinal pigment epithelium (RPE), may have no layers of retinal tissue leaving behind only bare scleral tissue (the white outer eye wall), or may be a combination of retinal and scleral tissue.

Figure 80B:
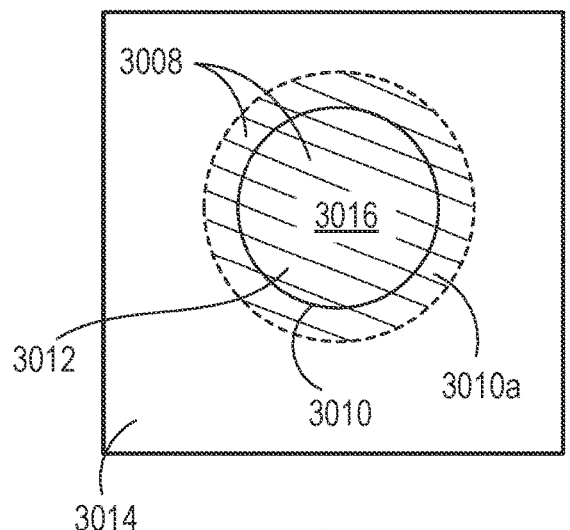
FIG. 80B is an illustration of an alternative retinal defect repair.

Alternatively, as illustrated in FIG. 80B, the bioadhesive 3008 can be applied to cover the entire retinal defect 3012, including the entirety of the tissue 3016 within the defect as well as overlapping the intact retinal tissue 3014 in the margin 3010a adjacent the border 3010. The bioadhesive can be applied to the entire retinal tissue within the defect, to the entirety of the internal aspect of the bare intact sclera tissue, or to an entirety of a combination of retinal tissue and bare intact scleral tissue within the defect.

Covering the entire defect 3012 is designed to reduce the likelihood of cells from within the retinal defect traveling from their normal anatomical location to a different location within the vitreous cavity or to other retinal and ocular tissues within the eye. Maintaining the RPE cells in their normal monolayer configuration, with normal cellular polarity, prevents or reduces the liberation of RPE cells from the base of the retinal defect, which in turn reduces the likelihood of epithelial-mesenchymal transition and subsequent development of proliferative vitreoretinopathy. In the retina, the process of epithelial-mesenchymal transition results in the differentiation of RPE cells into fibroblasts and myofibroblasts that can migrate and proliferate to form contractile epiretinal membranes formation that are damaging to ocular tissues.

In addition, applying the bioadhesive to cover the entire retinal defect 3012 is designed to reduce the risk of hypotony, i.e., low intraocular pressure, by limiting fluid movement across the RPE. Normal intraocular pressure is achieved by an equilibrium between aqueous fluid inflow produced by the ciliary body and outflow through the trabecular meshwork as well as a combination of active and passive flow across the retinal pigment epithelium to the choroid, which uses choroidal osmotic pressure to draw fluid into the choroidal vasculature. The intact retina provides significant resistance to this pathway of fluid flow across the RPE. Large areas of retinal breaks provide the potential for substantial fluid movement across the RPE, which can lead to hypotony and associated pathological changes such as corneal folds, corneal edema, choroidal folds, and choroidal detachment.

80b preferably do not include the application of a patch to the retinal tissue and are therefore "patch-less" techniques.

While certain embodiments of the inventions have been described, these embodiments have been presented by way of example only, and are not intended to limit the scope of the disclosure. Indeed, the novel methods and systems described herein may be embodied in a variety of other forms. Furthermore, various omissions, substitutions and changes in the systems and methods described herein may be made without departing from the spirit of the disclosure. The accompanying claims and their equivalents are intended to cover such forms or modifications as would fall within the scope and spirit of the disclosure. Accordingly, the scope of the present inventions is defined only by reference to the appended claims.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a sub combination or variation of a sub combination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A device for applying a bioadhesive substance within an eye, the device comprising:
   a sleeve defining a passageway extending therethrough, the sleeve having a longitudinal axis;
   an applicator received within the sleeve passageway and movable relative to the sleeve along the sleeve longitudinal axis, the applicator defining a lumen;
   the applicator including an applicator portion at a distal end of the applicator, the applicator defining an opening facing laterally relative to the longitudinal axis, the opening being in fluid communication with the lumen and a surface of the applicator portion, the applicator portion being deformable between a first shape receivable within the sleeve passageway and
   a second shape larger than the sleeve passageway, in the second shape the surface of the applicator portion being generally broad in width and length dimensons having a width and a length greater than a thickness of the applicator portion; and
   a source comprising the bioadhesive substance in fluid communication with at least the lumen.

2. The device of claim 1, wherein the lumen comprises a substance supply lumen extending along a length of the device through which the bioadhesive substance can pass so that the bioadhesive substance can be applied to the applicator portion.

3. The device of claim 1, wherein the laterally facing opening passes through the surface of the applicator portion.

4. The device of claim 3, wherein the laterally facing opening comprises a plurality of openings passing through the surface of the applicator portion.

5. The device of claim 1, wherein the lumen comprises the laterally facing opening.

6. The device of claim 5, wherein the lumen terminates at the laterally facing opening located at a juncture to the applicator portion.

7. The device of claim 1, wherein the applicator portion is biased such that a first side portion rolls or folds toward a second side portion of the applicator portion when the applicator portion is withdrawn into the sleeve.

8. The device of claim 1, wherein the applicator portion has an asymmetric shape such that a first side portion on one side of an axial centerline of the applicator portion has a different shape than a second side portion on an opposite side of the applicator portion, the first and second side portions being divided by the axial centerline of the applicator portion.

9. The device of claim 1, wherein the applicator portion has an asymmetric shape having a first side portion on one side of an axial centerline of the applicator portion that has a first length that is longer than a second length of a second side portion on a second side of the axial centerline of the applicator portion.

10. The device of claim 9, wherein the first side portion has a first transition portion that has a first length in the axial direction and the second side portion has a second transition portion that has a second length in the axial direction, and wherein the first length of the first transition portion is less than the second length of the second transition portion.

11. The device of claim 1, wherein the applicator portion has an asymmetric width.

12. The device of claim 1, wherein the applicator portion has an asymmetric thickness in a widthwise direction, such that a thickness profile of the applicator portion on a first side of the applicator portion is different than a thickness profile of the application portion on a second side of the applicator portion.

13. The device of claim 12, wherein the applicator portion on the first side is more flexible than the applicator portion on the second side.

14. The device of claim 1, wherein the applicator portion is configured such that a first side portion contracts before a second side portion contracts when the applicator portion is withdrawn into the sleeve.

15. The device of claim 1, wherein the applicator portion has an asymmetric width and the thickness of the applicator portion is asymmetric.

16. The device of claim 1, wherein the sleeve has a notch in a distal end thereof.

17. The device of claim 1, wherein the applicator portion is flexible such that in the second shape the applicator portion is configured to bend to brush up against a surface within the eye.

18. A device for applying a bioadhesive substance within an eye, the device comprising:
   a sleeve defining a passageway extending therethrough, the sleeve having a longitudinal axis;
   an applicator received within the sleeve passageway and movable relative to the sleeve along the sleeve longitudinal axis;
   an applicator portion at a distal end of the applicator, the applicator portion defining an opening passing through a surface of the applicator portion, the applicator portion being deformable between a first shape receivable within the sleeve passageway and
   a second shape larger than the sleeve passageway, in the second shape the surface of the applicator portion being generally broad in width and length dimenions having a width and a length greater than a thickness of the applicator portion; and
   a source comprising the bioadhesive substance in fluid communication with the opening.

19. The device of claim 18, wherein the applicator portion defines a plurality of openings passing through the surface of the applicator portion.

20. The device of claim 18, wherein the applicator portion is biased such that a first side portion rolls or folds toward a second side portion of the applicator portion when the applicator portion is withdrawn into the sleeve.

21. The device of claim 18, wherein the applicator portion has an asymmetric shape such that a first side portion on one side of an axial centerline of the applicator portion has a different shape than a second side portion on an opposite side of the applicator portion, the first and second side portions being divided by the axial centerline of the applicator portion.

22. The device of claim 18, wherein the applicator portion has an asymmetric shape having a first side portion on one side of an axial centerline of the applicator portion that has a first length that is longer than a second length of a second side portion on a second side of the axial centerline of the applicator portion.

23. The device of claim 22 wherein the first side portion has a first transition portion that has a first length in the axial direction and the second side portion has a second transition portion that has a second length in the axial direction, and wherein the first length of the first transition portion is less than the second length of the second transition portion.

24. The device of claim 18, wherein the applicator portion has an asymmetric width.

25. The device of claim 18, wherein the applicator portion has an asymmetric thickness in a widthwise direction, such that a thickness profile of the applicator portion on a first side of the applicator portion is different than a thickness profile of the application portion on a second side of the applicator portion.

26. The device of claim 24, wherein the applicator portion on the first side is more flexible than the applicator portion on the second side.

27. The device of claim 18, wherein the applicator portion is configured such that a first side portion contracts before a second side portion contracts when the applicator portion is withdrawn into the sleeve.

28. The device of claim 18, wherein the applicator portion has an asymmetric width and the thickness of the applicator portion is asymmetric.

29. The device of claim 18, wherein the sleeve has a notch in a distal end thereof.

30. The device of claim 18, wherein the applicator portion is flexible such that in the second shape the applicator portion is configured to bend to brush up against a surface within the eye.

31. A device for applying a bioadhesive substance within an eye, the device comprising:
   a sleeve defining a passageway extending therethrough, the sleeve having a longitudinal axis;

an applicator received within the sleeve passageway and movable relative to the sleeve along the sleeve longitudinal axis, the applicator defining a substance supply lumen;

an applicator portion at a distal end of the applicator, the substance supply lumen having a laterally facing, distal opening for supplying a substance to a surface of the applicator portion from a proximal region of the applicator portion, the applicator portion being deformable between a first shape receivable within the sleeve passageway and a second shape larger than the sleeve passageway, in the second shape the surface of the applicator portion being generally broad in width and length dimensions having a width and a length greater than a thickness of the applicator portion; and a source comprising the bioadhesive substance in fluid communication with at least the substance supply lumen.

32. The device of claim 31, wherein the applicator portion is biased such that a first side portion rolls or folds toward a second side portion of the applicator portion when the applicator portion is withdrawn into the sleeve.

33. The device of claim 31, wherein the applicator portion has an asymmetric shape such that a first side portion on one side of an axial centerline of the applicator portion has a different shape than a second side portion on an opposite side of the applicator portion, the first and second side portions being divided by the axial centerline of the applicator portion.

34. The device of claim 31, wherein the applicator portion has an asymmetric shape having a first side portion on one side of an axial centerline of the applicator portion that has a first length that is longer than a second length of a second side portion on a second side of the axial centerline of the applicator portion.

35. The device of claim 34, wherein the first side portion has a first transition portion that has a first length in the axial direction and the second side portion has a second transition portion that has a second length in the axial direction, and wherein the first length of the first transition portion is less than the second length of the second transition portion.

36. The device of claim 31, wherein the applicator portion has an asymmetric width.

37. The device of claim 31, wherein the applicator portion has an asymmetric thickness in a widthwise direction, such that a thickness profile of the applicator portion on a first side of the applicator portion is different than a thickness profile of the application portion on a second side of the applicator portion.

38. The device of claim 37, wherein the applicator portion on the first side is more flexible than the applicator portion on the second side.

39. The device of claim 31, wherein the applicator portion is configured such that a first side portion contracts before a second side portion contracts when the applicator portion is withdrawn into the sleeve.

40. The device of claim 31, wherein the applicator portion has an asymmetric width and the thickness of the applicator portion is asymmetric.

41. The device of claim 31, wherein the sleeve has a notch in a distal end thereof.

42. The device of claim 31, wherein the applicator portion is flexible such that in the second shape the applicator portion is configured to bend to brush up against a surface within the eye.

* * * * *